(12) United States Patent
Eggers et al.

(10) Patent No.: US 7,920,926 B2
(45) Date of Patent: Apr. 5, 2011

(54) METHOD AND APPARATUS FOR CARRYING OUT THE CONTROLLED HEATING OF TISSUE IN THE REGION OF DERMIS

(75) Inventors: Philip E. Eggers, Dublin, OH (US); Andrew R. Eggers, Ostrander, OH (US); Eric A. Eggers, Portland, OR (US)

(73) Assignee: Apsara Medical Corporation, Santa Clara, CA (US)

( * ) Notice: Subject to any disclaimer, the term of this patent is extended or adjusted under 35 U.S.C. 154(b) by 1146 days.

(21) Appl. No.: 11/583,555

(22) Filed: Oct. 19, 2006

(65) Prior Publication Data

US 2007/0135880 A1 Jun. 14, 2007

Related U.S. Application Data

(63) Continuation-in-part of application No. 11/298,420, filed on Dec. 9, 2005, now Pat. No. 7,613,523.

(51) Int. Cl.
*A61F 2/00* (2006.01)
(52) U.S. Cl. .......................................... 607/103; 607/96
(58) Field of Classification Search ............ 607/96–103, 607/113
See application file for complete search history.

(56) References Cited

U.S. PATENT DOCUMENTS

| | | |
|---|---|---|
| 4,144,327 A | 3/1979 | Davies et al. |
| 4,976,709 A | 12/1990 | Sand |
| 5,304,169 A | 4/1994 | Sand |
| 5,484,432 A | 1/1996 | Sand |
| 5,569,242 A | 10/1996 | Lax et al. |
| 5,755,753 A | 5/1998 | Knowlton |
| 5,853,755 A | 12/1998 | Foldvari |
| 5,925,078 A | 7/1999 | Anderson |
| 6,169,926 B1 | 1/2001 | Baker |
| 6,193,963 B1 | 2/2001 | Stern et al. |
| 6,203,540 B1 | 3/2001 | Weber |
| 6,241,753 B1 | 6/2001 | Knowlton |

(Continued)

OTHER PUBLICATIONS

NC Samaranayake, et al., "Antifungal effects of lysozyme and lactoferrin against genetically similar, sequential Candida albicans isolates from a human immunodeficiency virus-infected southern Cinese cohort." J. Clin. Microbiol. 39: 3296-3302 (2001). This publication discusses antifungal effects of lysozyme and lactoferrin.

(Continued)

*Primary Examiner* — Roy D Gibson
(74) *Attorney, Agent, or Firm* — Mueller Smith & Okuley, LLC

(57) ABSTRACT

Implant apparatus and method for effecting a controlled heating of tissue within the region of dermis of skin. The heater implants are configured with a thermally insulative generally flat support functioning as a thermal barrier. One surface of this thermal barrier carries one or more polymerically encapsulated heater resistor segments with a lead assemblage exhibiting a 4-point topology. Each of the encapsulated heater segments may be thermally associated with a metal thermal spreader dimensioned in correspondence with and aligned with the heater segments. The implants are located within heating channels at the interface between skin dermis and the next adjacent subcutaneous tissue layer such that the heat spreaders are contactable with the lower region of dermis. During therapy a conformal heat sink is positioned against the skin above the implants and a slight tamponade is applied through the heat sink to assure a proper form of conduction heat transfer. An adjuvant may be employed to infiltrate dermis to significantly lower the thermal threshold transition temperature for dermis or dermis component shrinkage. The method and apparatus also may be employed in the treatment of capillary malformation (port wine stain).

59 Claims, 48 Drawing Sheets

U.S. PATENT DOCUMENTS

| | | |
|---|---|---|
| 6,277,116 B1 | 8/2001 | Utely et al. |
| 6,306,119 B1 | 10/2001 | Weber et al. |
| 6,311,090 B1 | 10/2001 | Knowlton |
| 6,375,672 B1 | 4/2002 | Aksan et al. |
| 6,381,498 B1 | 4/2002 | Knowlton |
| 6,391,023 B1 | 5/2002 | Weber et al. |
| 6,405,090 B1 | 6/2002 | Knowlton |
| 6,432,101 B1 | 8/2002 | Weber et al. |
| 6,440,121 B1 | 8/2002 | Weber et al. |
| 6,524,250 B1 | 2/2003 | Weber et al. |
| 6,663,618 B2 | 12/2003 | Weber et al. |
| 6,699,237 B2 | 3/2004 | Weber et al. |
| 6,726,693 B2 | 4/2004 | Weber et al. |
| 6,764,493 B1 | 7/2004 | Weber et al. |
| 6,787,152 B2 | 9/2004 | Kirby et al. |
| 6,920,883 B2 | 7/2005 | Bessette et al. |
| 6,974,450 B2 | 12/2005 | Weber et al. |
| 2005/0059940 A1 | 3/2005 | Weber et al. |
| 2005/0222565 A1 | 10/2005 | Manstein |

OTHER PUBLICATIONS

Scherbel, et al., "Further observations on the effect of dimethyl sulfoxide in patients with generalized scleroderma (Progressive Systemic Sclerosis)." Ann. NY Acad. Sci., 613-629 (1968).

Sulamanidze, et al., "Removal of Facial Soft Tissue Ptosis With Special Threads", Dermatol Surg. 28:367-371 (2002).

NC Tsai, et al., "Metabolic approaches to enhance transdermal drug delivery: Effect of lipid synthesis inhibitors." J. Pharm. Sciences, 85: 643-648 (2000) (Abstract Only).

Abraham, et al., "Current Concepts in Nonablative Radiofrequency Rejuvenation of the Lower Face and Neck" Facial Plastic Surgery. vol. 21 No. 1 (2005).

Baca-Estrada, et al., "Effects of IL-12 on immune responses induced by transcutaneous immunization with antigens formulated in a novel lipid-based biphasic delivery system." Vaccine, 18: 1847-1854 (2000).

Bincheng, et al., Accurate Measurement of Blood Vessel Depth in Port Wine Stain Human Skin in vivo Using "Photothermal Radiometry", J. Biomed. Opt. (5), 961-966 (Sep./Oct. 2004).

Brown, et al., "Observations on the shrink temperature of collagen and its variations with age and disease." Ann. Rhuem. Dis., 17: 196 (1958).

Clark, L.E., and Mellette, J.R. "The Use of Hyaluronidase as an Adjunct to Surgical Procedures", J. Dermaton. Surg. Oncol., 20:842-844 (1994).

El-Domyati, et al., "Trichloroacetic acid peeling versus dermabrasion: a histometric, immunohistochemical, and ultrastructural comparison." J. Dermatol. Surg., 30: 179-188 (2004).

Fiskerstrand, et al., "Laser Treatment of Port Wine Stains: Therapeutic Outcome in Relation to Morphological Parameters" Brit. J. of Derm., 134, 1039-1043, (1996).

Fitzpatrick, et al., "Collagen Tightening Induced by Carbon Dioxide Laser Versus Erbium: YAG Laser" Lasers in Surgery and Medicine 27: 395-403 (2000).

Fitzpatrick, et al., "Multicenter Study of Noninvasive Radiofrequency for Periorbital Tissue Tightening", Lasers in Surgery in Medicine 33:232-242 (2003).

NC Kirby, K., "Liquid transdermal drug delivery: the state of the TDS® art." Drug Delivery Report, Autumn/Winter 1005: 58-62 (2005).

Lawrence, et al., "History of Dermabrasion" Dermatol Surg 2000; 26:95-101.

Lewis-Smith, P.A., "Adjunctive use of hyaluronidase in local anesthesia" Brit. J. Plastic Surgery, 39: 554-558 (1986).

Lycka, et al. "The Emerging Technique of the Antiptosis Subdermal Suspension Thread", Dermatol Surg. 30:41-44 (2004).

Manstein, et al., "Fractional Photothermolysis: A New Concept for Cutaneous Remodeling Using Microscopic Patterns of Thermal Injury"; Lasers in Surgery and Medicine 34:426-438 (2004).

Mihm, Jr., et al, "Science, Math and Medicine—Working Together to Understand the Diagnosis, Classification and Treatment of Port-Wine Stains", a paper presented in Mt. Tremblant, Quebec, Canada, 2004, Controversies and Conversations in Cutaneous Laser Surgery—An Advanced Symposium.

Moy, et al., "Comparison of the Effect of Various Chemical Peeling Agents in a Mini-Pig Model" Dermatol Surg 1996; 22:429-432.

Muravev, et al., "The efficacy of long-term application of dimethyl sulfoxide in a complex therapy of patients with systemic scleroderma." Ter Arkh. 57(8):125-7. PMID: 3906994 (1985) (Original in Russian, translation only attached.).

Palmieri, et al., "Topical treatment of some dystrophic and phlogistic lesions of skin and soft tissues." Arch. Sc. Med., 134:481-485 (1977). (English summary at conclusion of paper).

Pankhurst, "Incipient shrinkage of collagen and gelatin." Nature, 159: 538.

Rasmussen, et al., "Isotonic and Isometric Thermal Contraction of Human Dermis I. Technic and Controlled Study", J. Invest. Derm. 1964; 43:333-9.

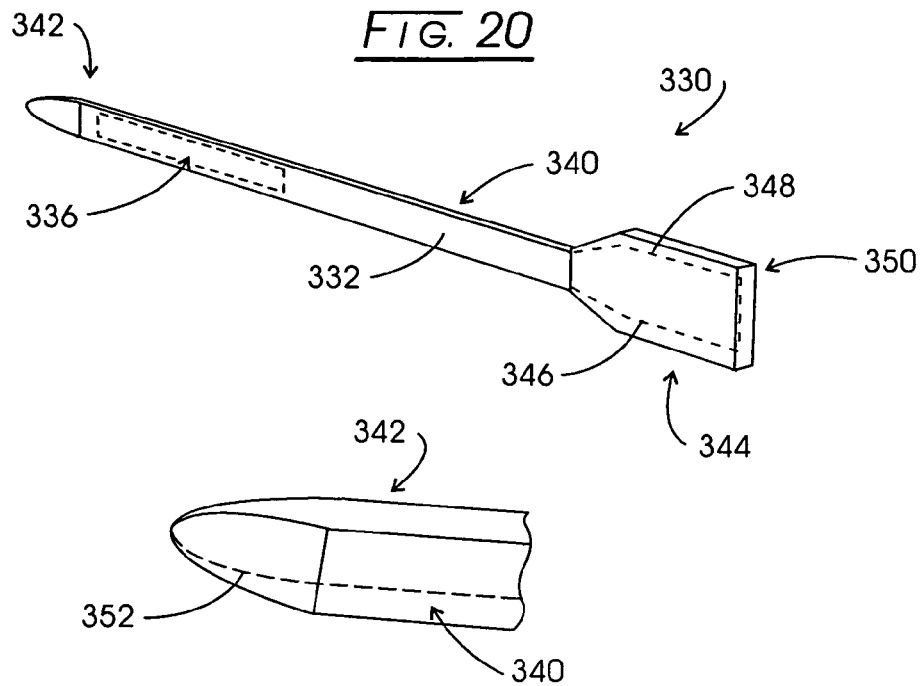
FIG. 20
FIG. 21
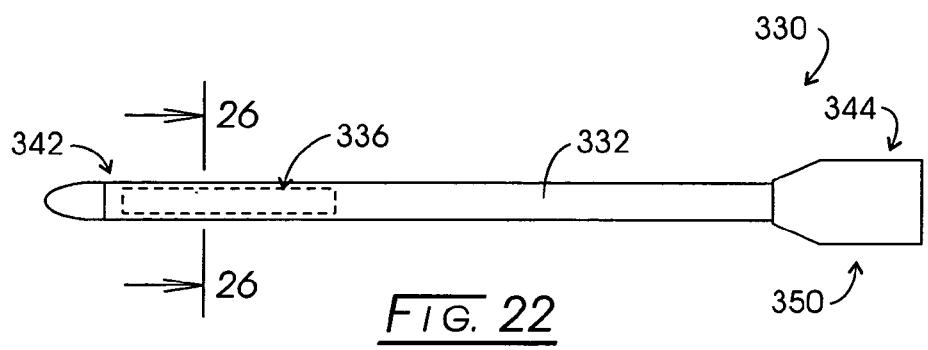
FIG. 22
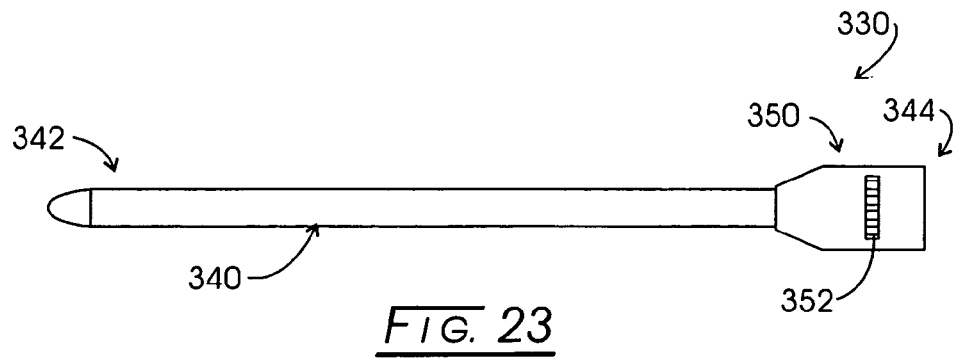
FIG. 23

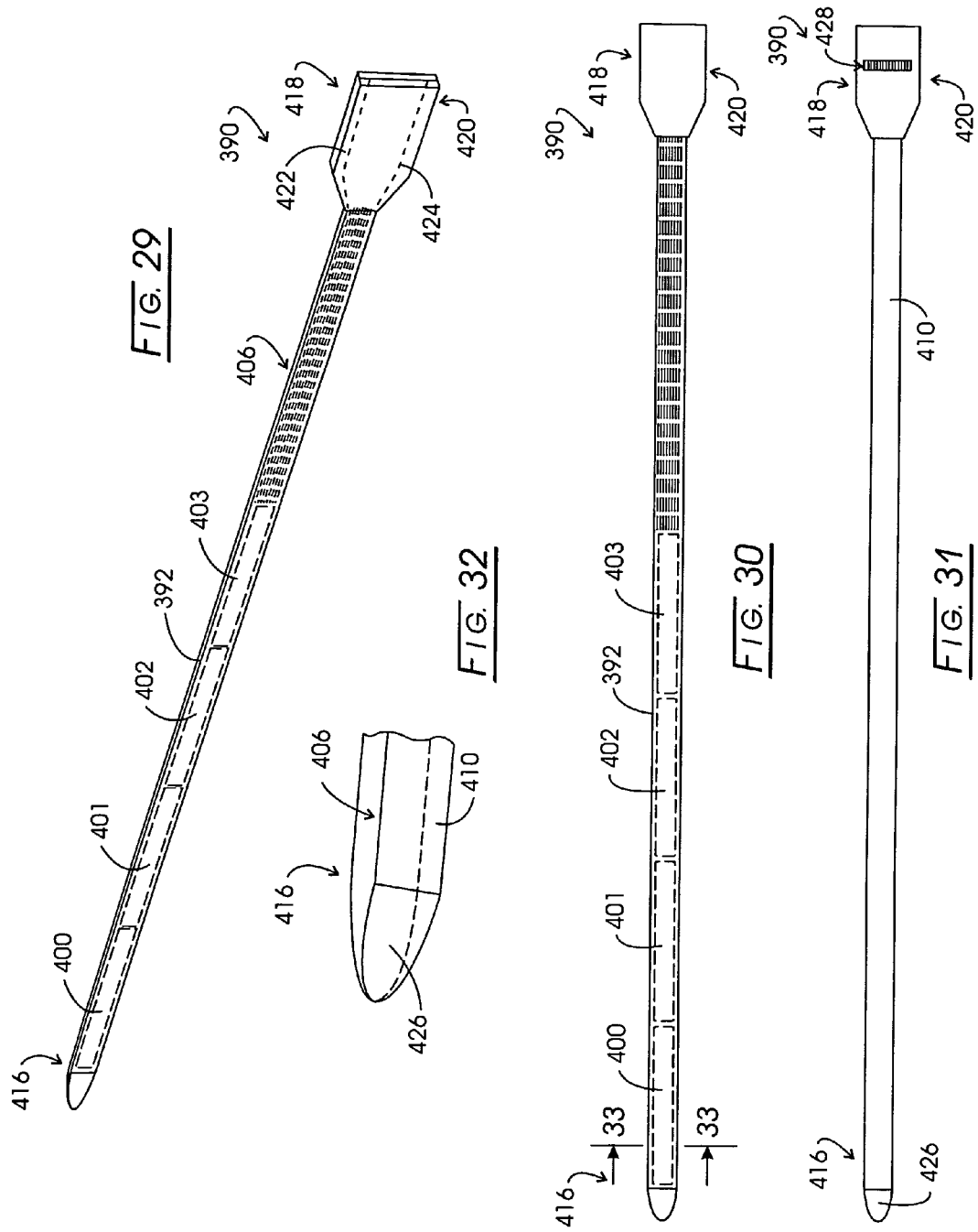

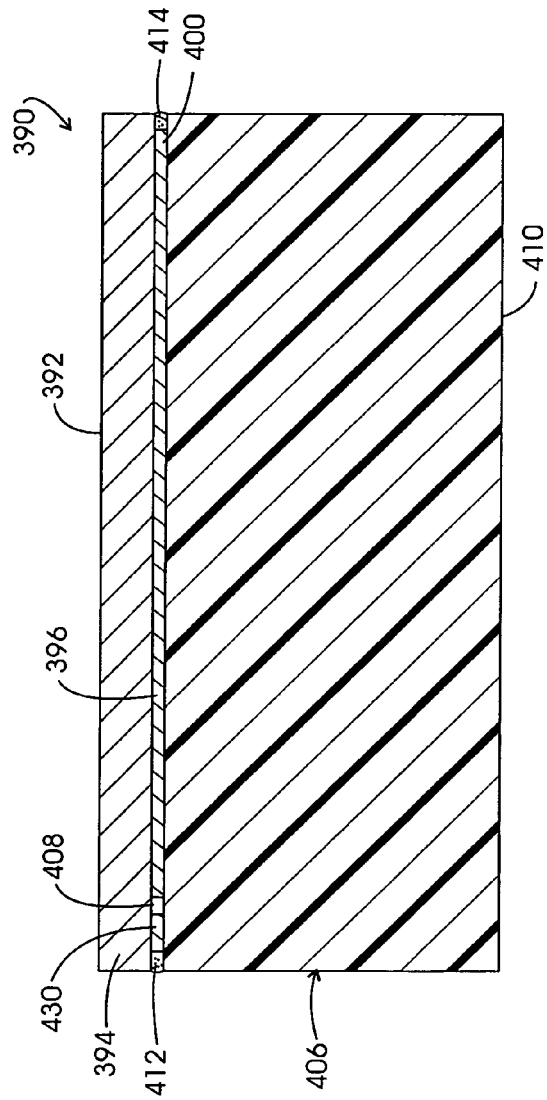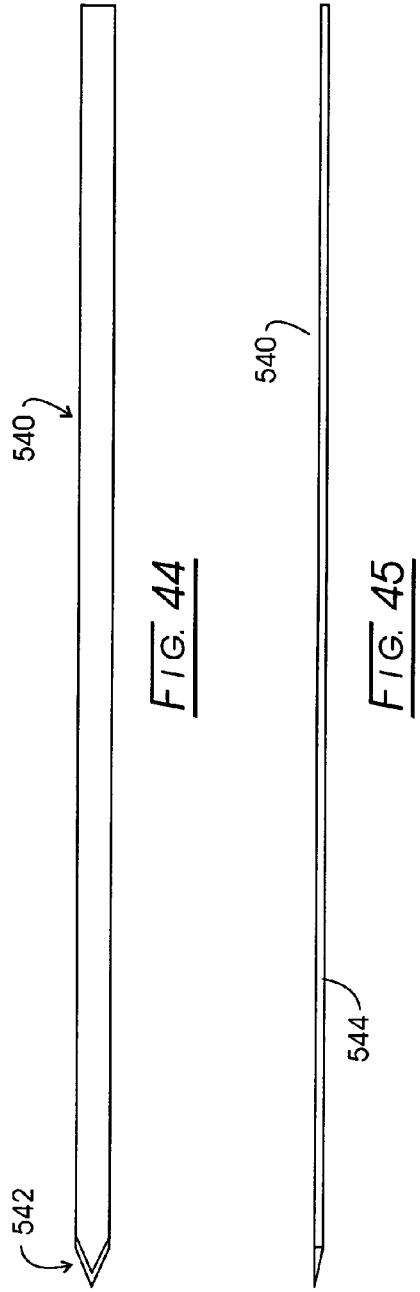

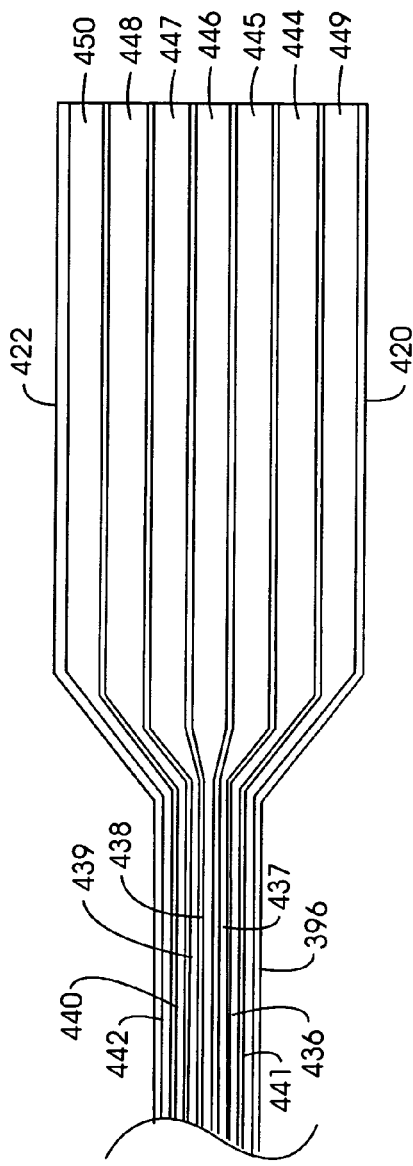
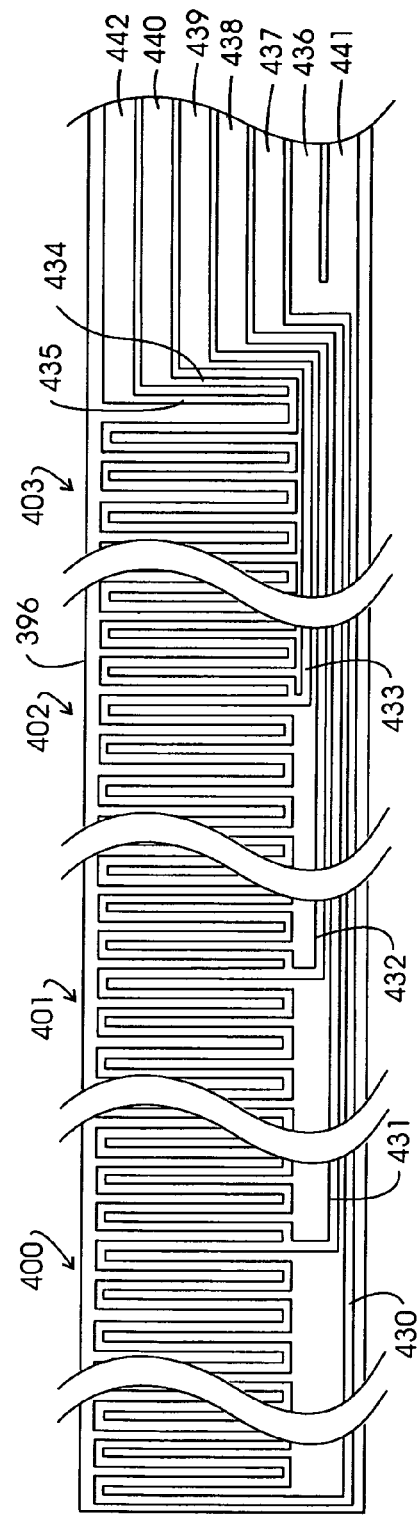
FIG. 35
FIG. 34

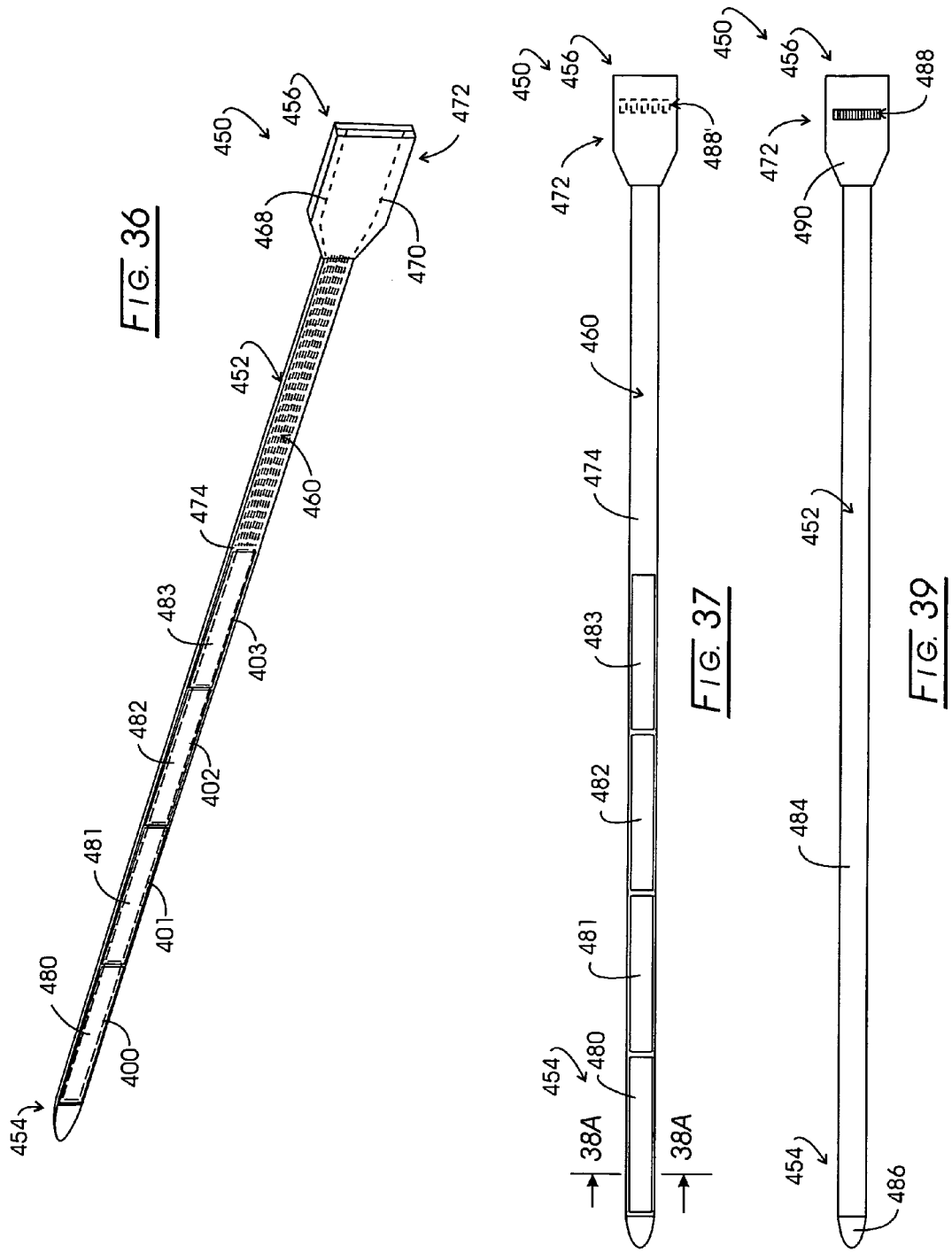

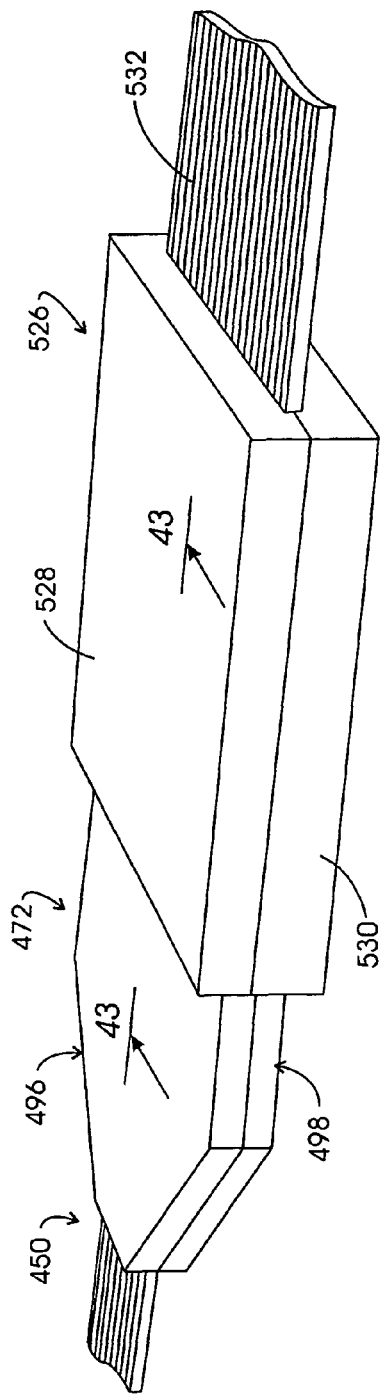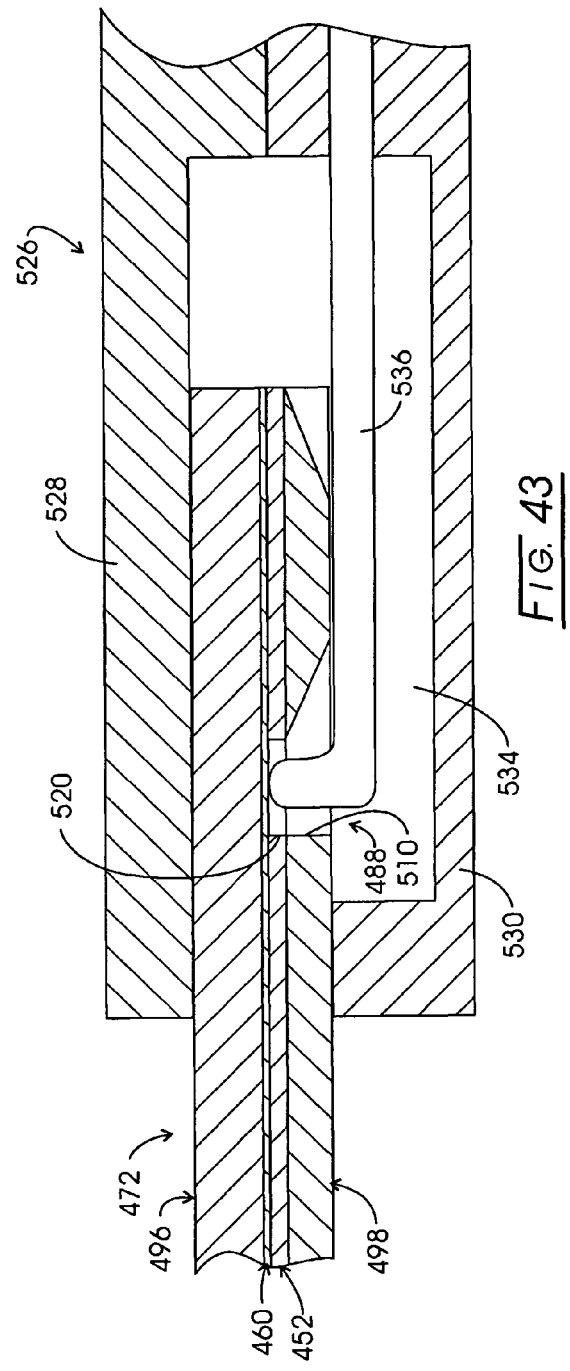

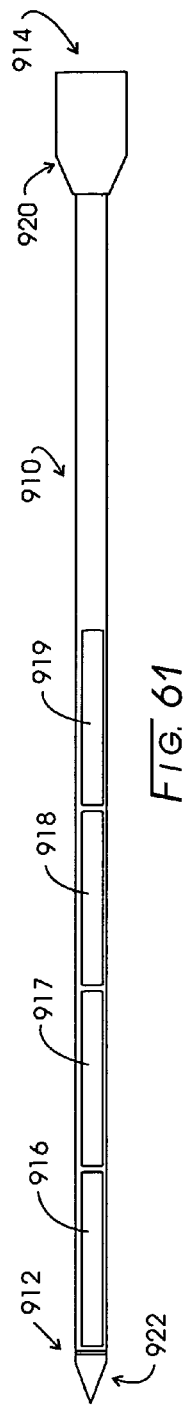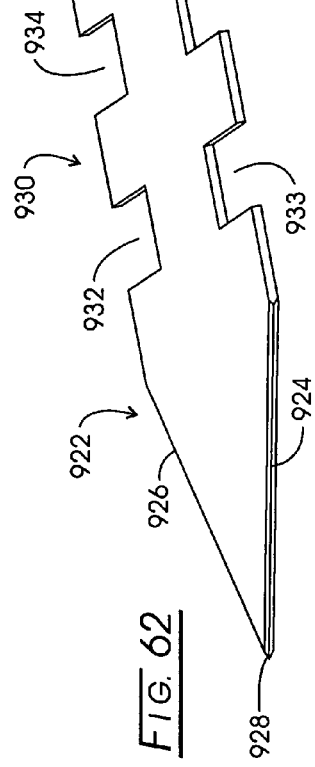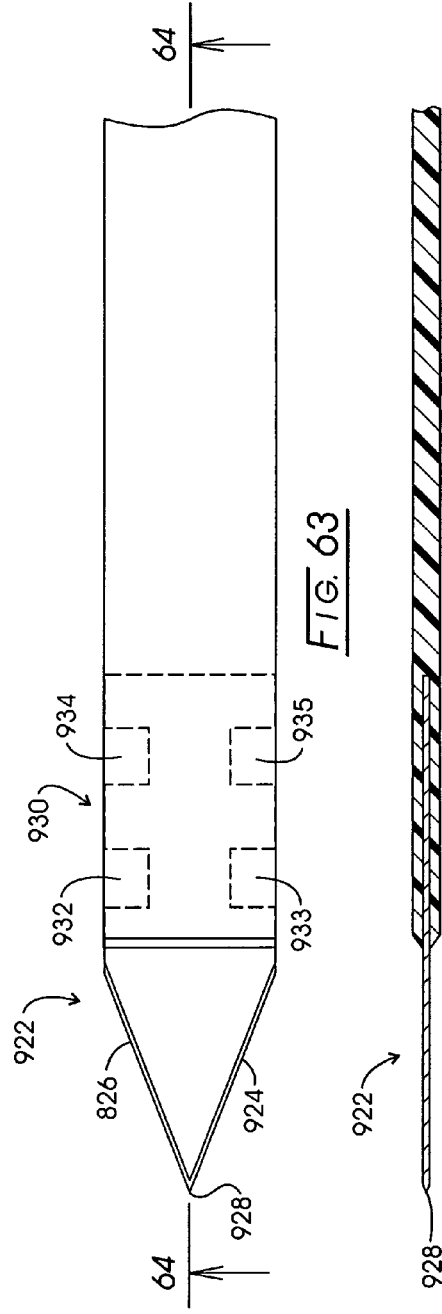

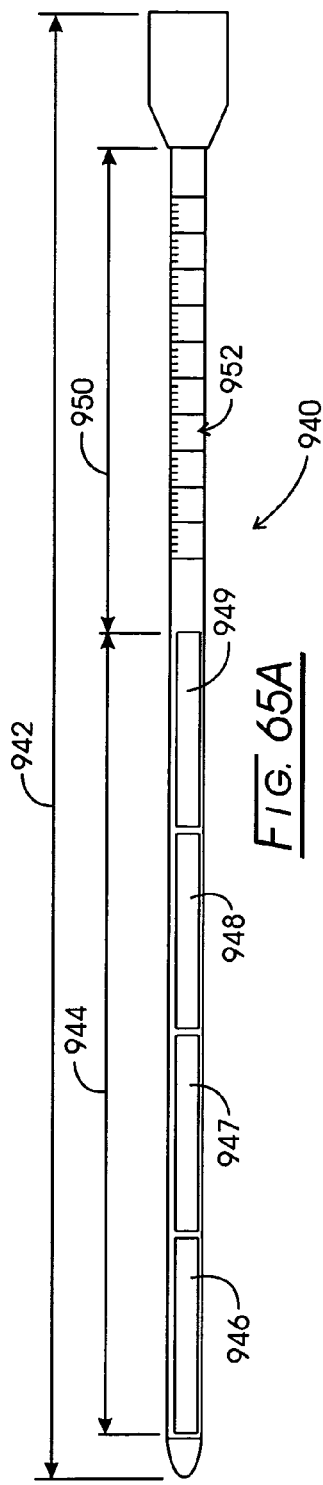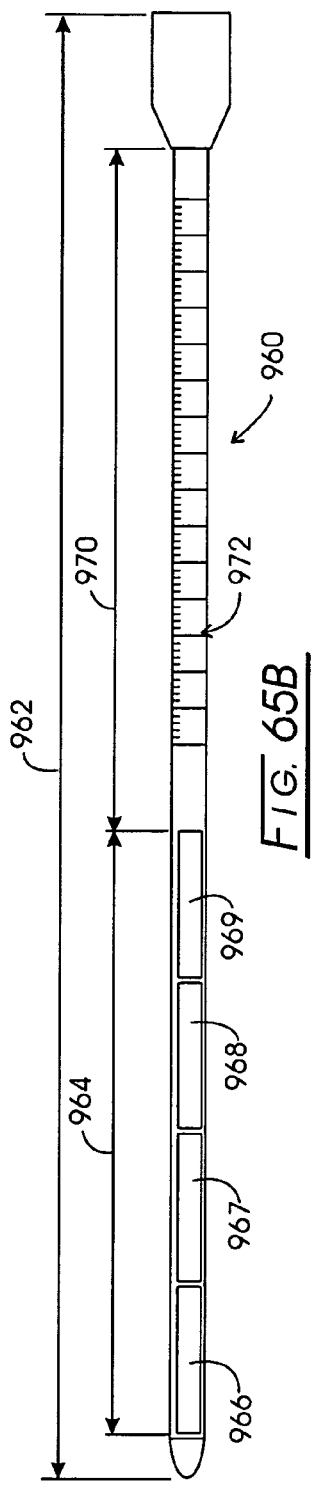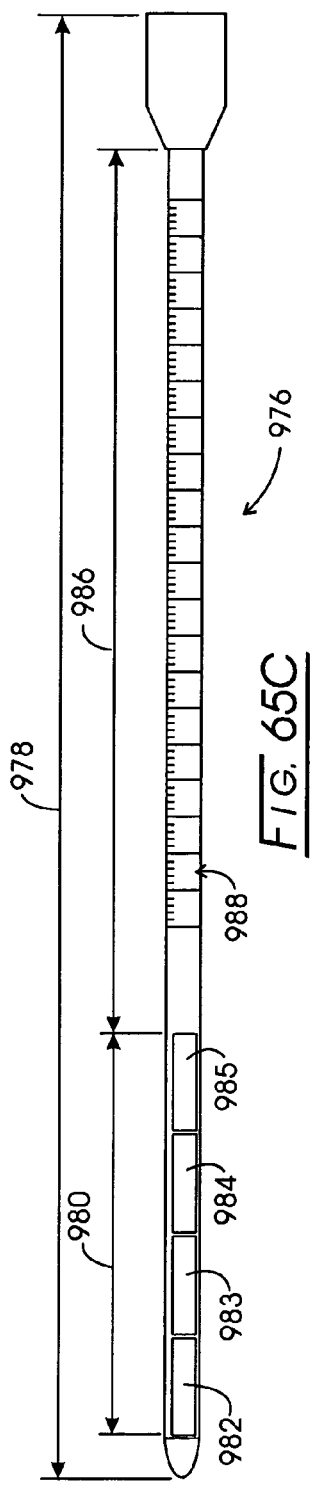

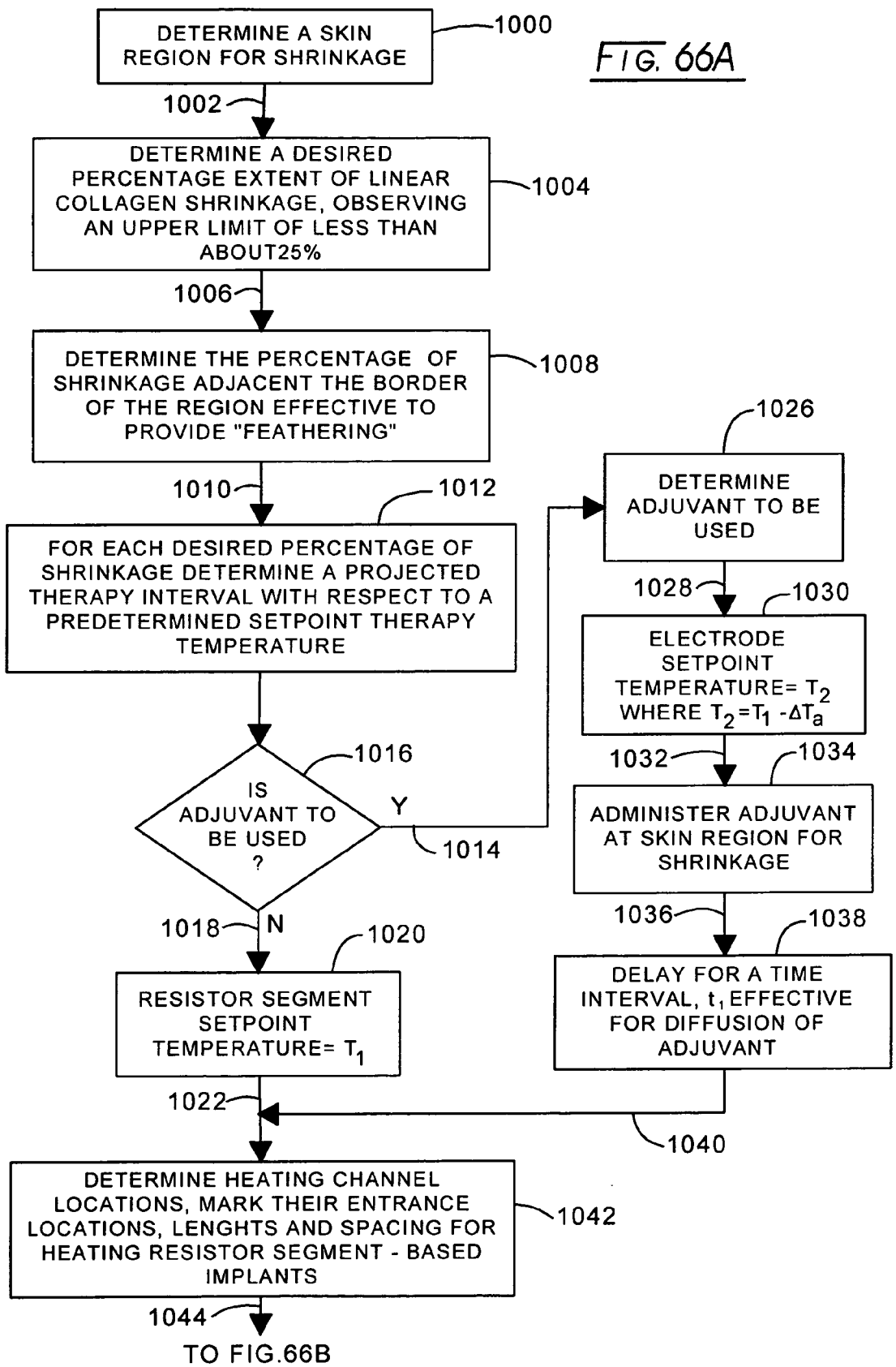

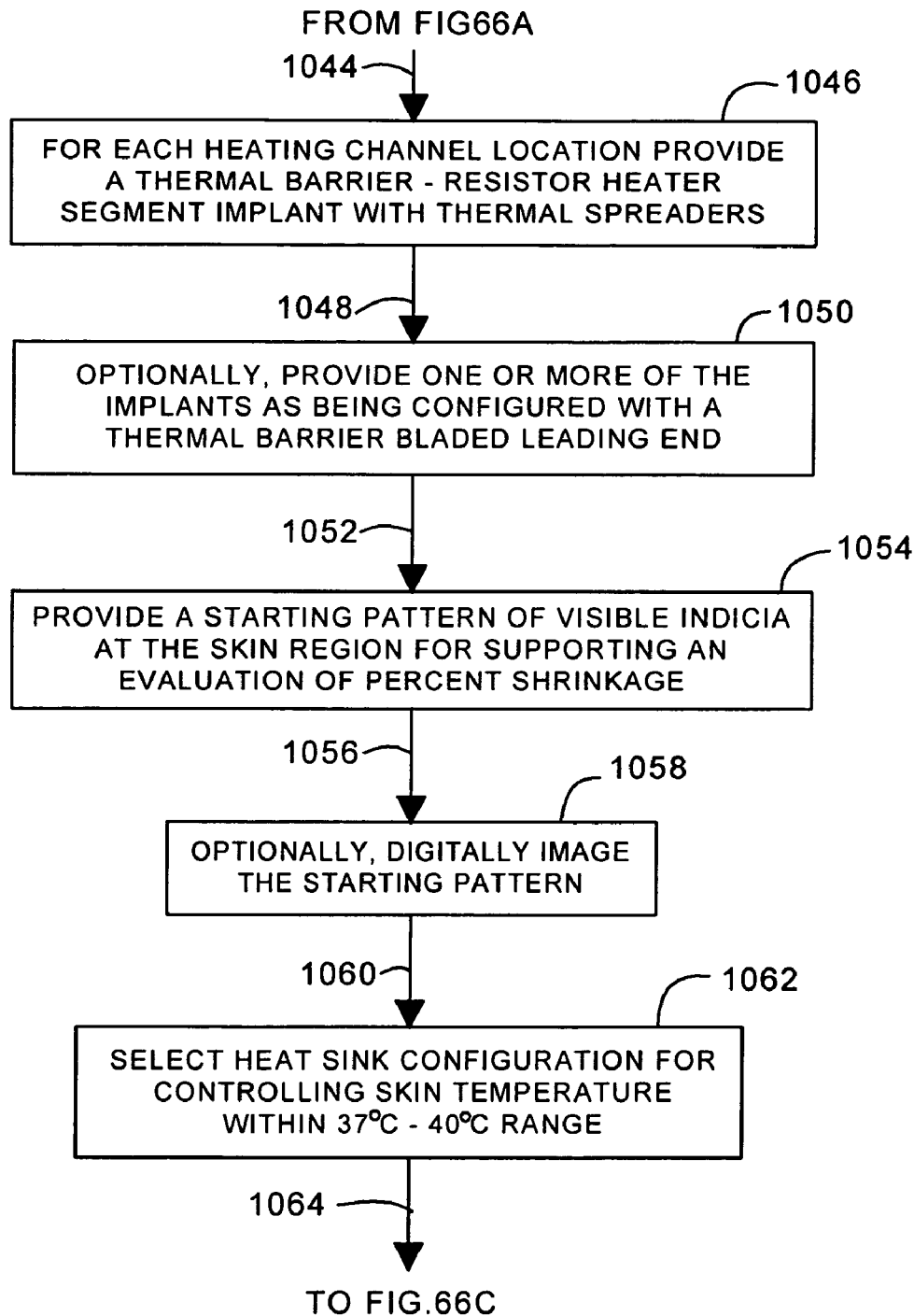

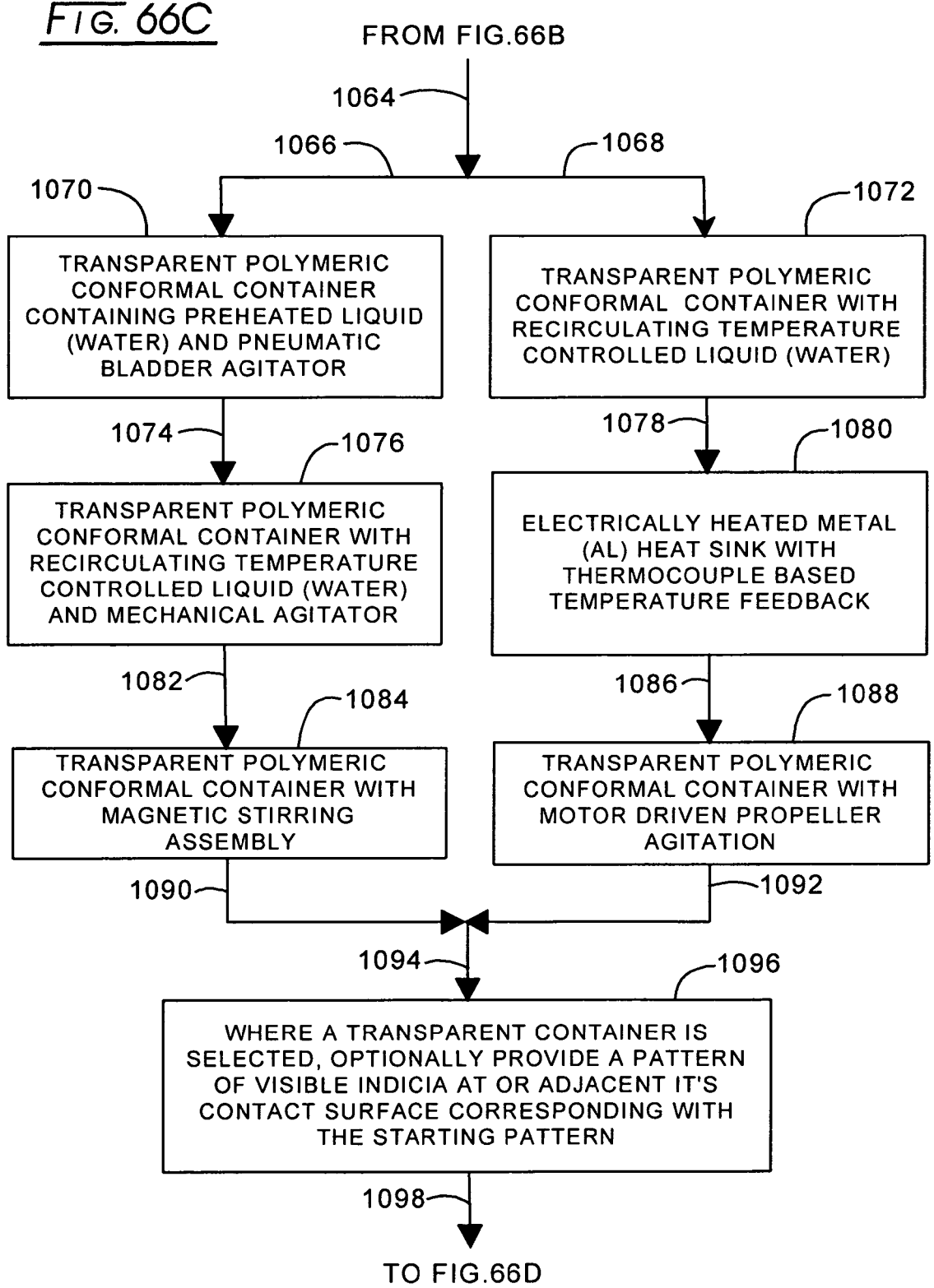

*FIG. 66D*

FROM FIG.66C
1098

1100: WHERE A TRANSPARENT CONTAINER IS SELECTED, OPTIONALLY PROVIDE A THIN, TRANSPARENT LAYER OF THERMOCHROMIC MATERIAL HAVING A VISUALLY PERCEPTIBLE COLOR CUE AT EPIDERMIS TEMPERATURES ABOVE MAXIMUM. LAYER IS LOCATED AT "SKIN" SIDE OF CONTAINER CONTACT SURFACE

1102 ↓

1104: OPTIONALLY PROVIDE ONE OR MORE TEMPERATURE SENSOR(S) ON THE CONTAINER SURFACE DISPLACED FROM THE CONTACT SURFACE EFFECTIVE TO REPORT TEMPERATURE OF LIQUID, e.g. WATER INSIDE THE CONTAINER WHILE IT IS BEING STIRRED

1106 ↓

1108: DETERMINE APPROPRIATE HEAT SINK TEMPERATURE (22°C - 30°C) TAKING INTO ACCOUNT THE TEMPERATURE DROP AT THE INTERFACE BETWEEN EPIDERMIS SURFACE AND HEAT SINK CONTACT SURFACE WITH RESPECT TO PREDETERMINED SKIN (EPIDERMIS) SURFACE TEMPERATURE

1110 ↓

1112: PRE-COOL SUBCUTANEOUS FAT LAYER FROM SKIN SURFACE FOR A PRE-COOL INTERVAL

FROM FIG. 66D

1114 ↓

1116 — OPTIONALLY, PROVIDE DISSECTING INSTRUMENT WITH OUTWARDLY BIASING "SLED" TIP CONFIGURED FOR BLUNT DISSECTION, WHERE BLADED IMPLANT HAS NOT BEEN SELECTED

1118 ↓

1124 — DELAY t2 FOR ANESTHETIC EFFECTIVENESS WHERE t2 > t1

1126 ↓

1128 — ATTACH RESISTOR SEGMENT LEADS TO CONTROLLER

1130 ↓

1132 — FOR EACH HEATING CHANNEL ENTRANCE LOCATION, USING A SCALPEL, FORM AN ENTRANCE INCISION TO THE DERMIS-SUBCUTANEOUS FAT LAYER INTERFACE

1134 ↓

1136 — USING DISSECTING INSTRUMENT, FORM HEATING CHANNELS AT MARKED HEATING CHANNEL LOCATIONS

1138 ↓

1140 — INSERT AN IMPLANT WITHIN EACH HEATING CHANNEL IN AN ORIENTATION WHEREIN ALL RESISTOR HEATER SEGMENTS ARE LOCATED FOR THERMAL EXCHANGE WITH DERMIS

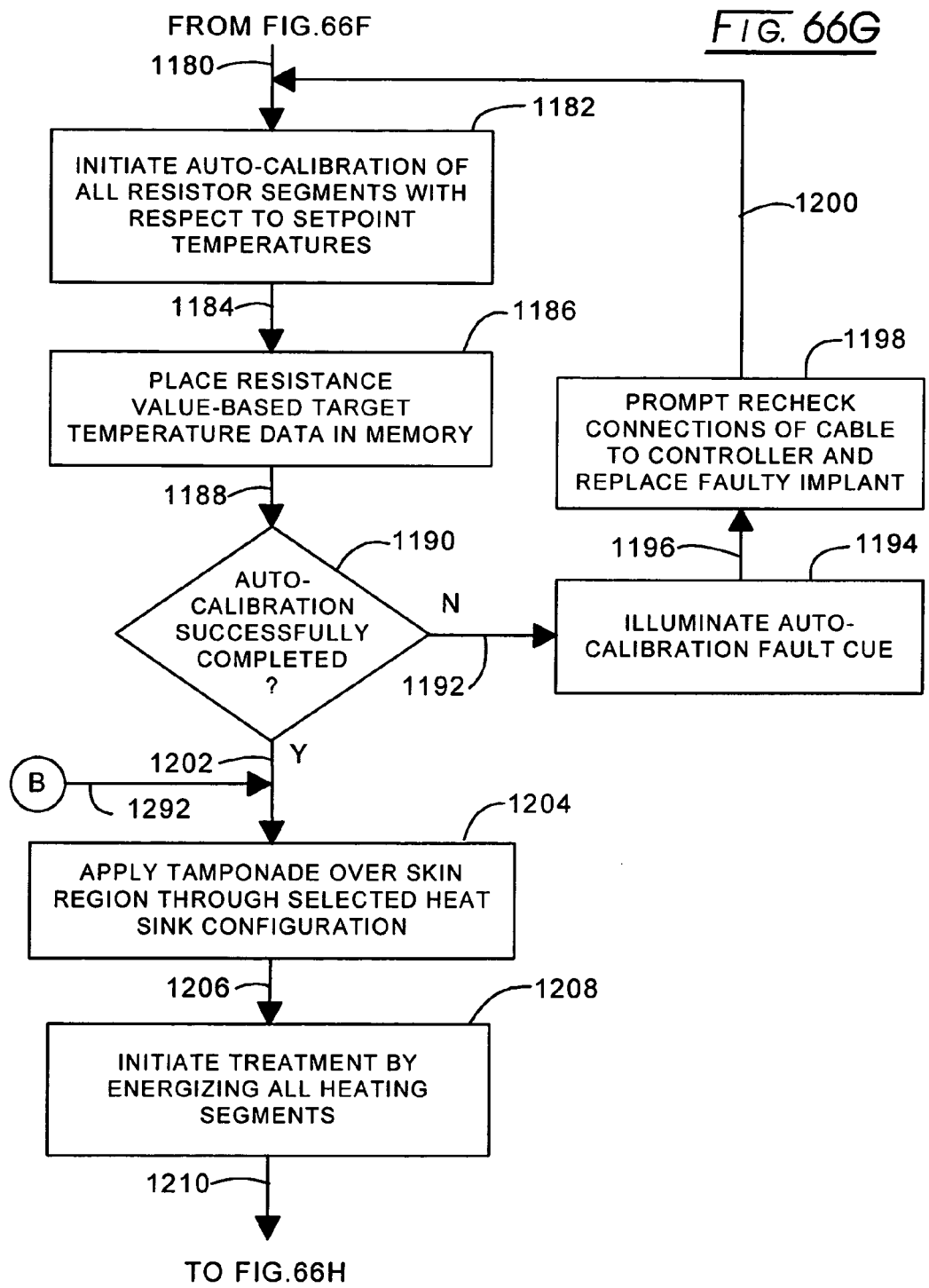

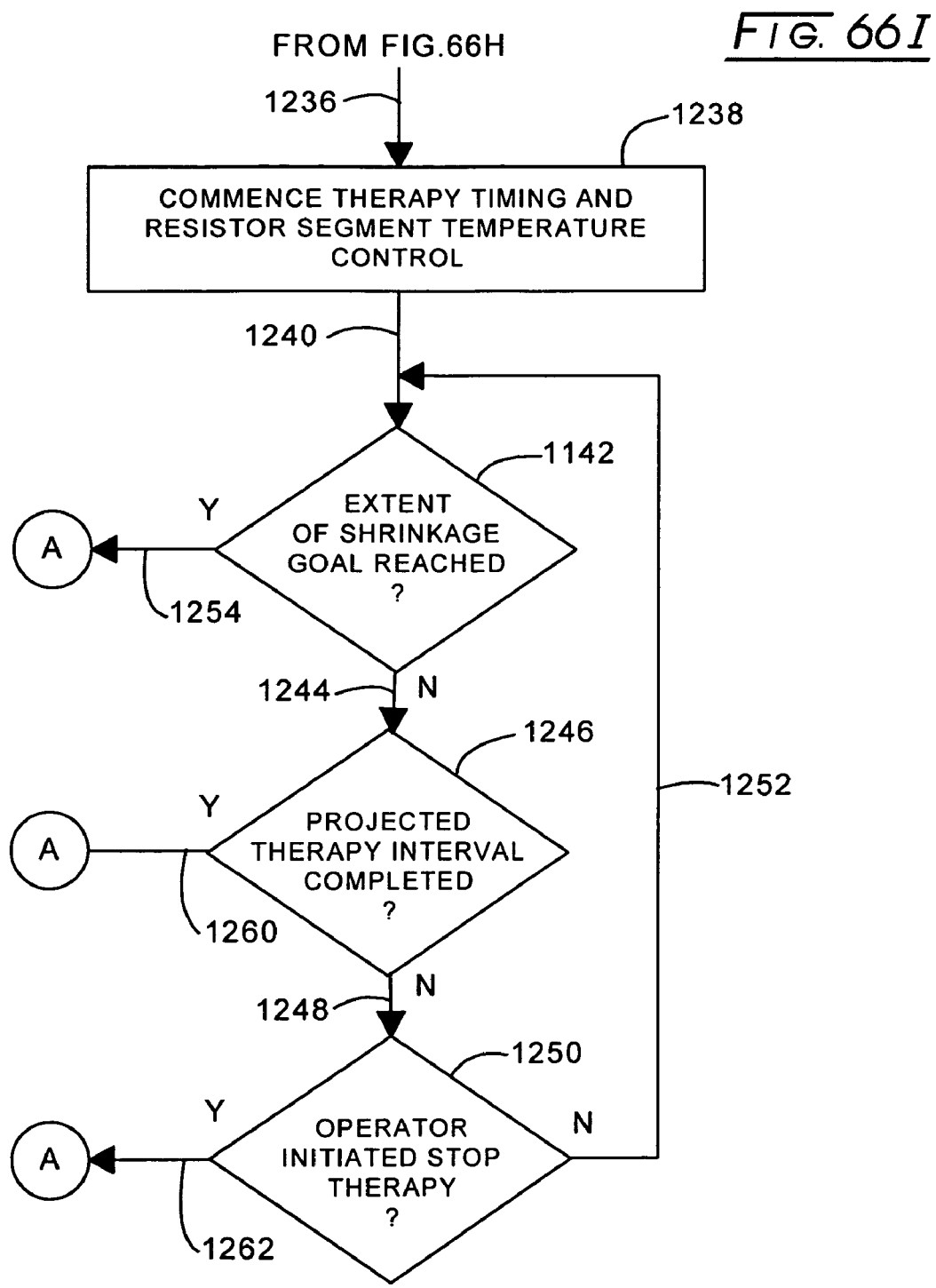

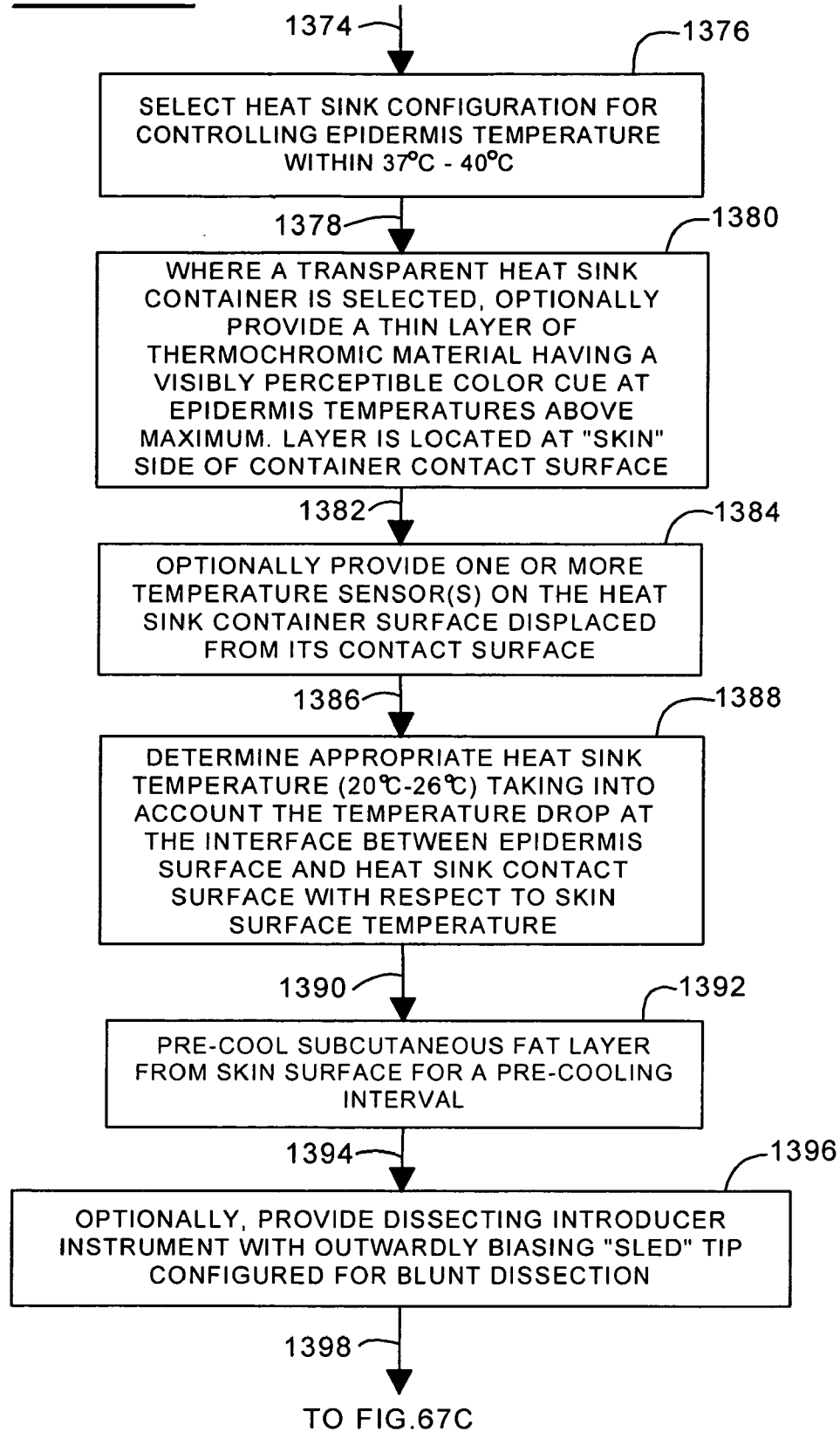

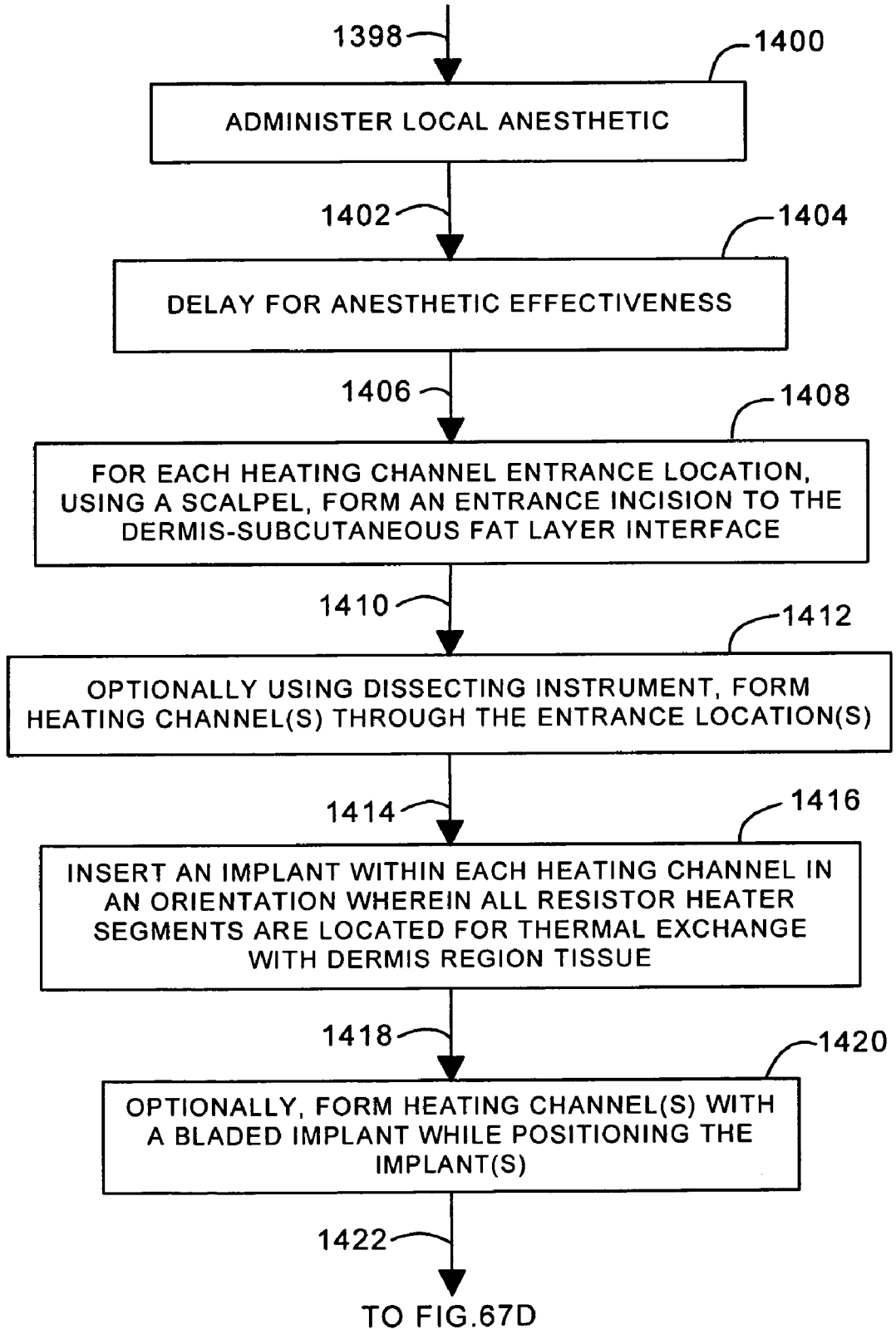

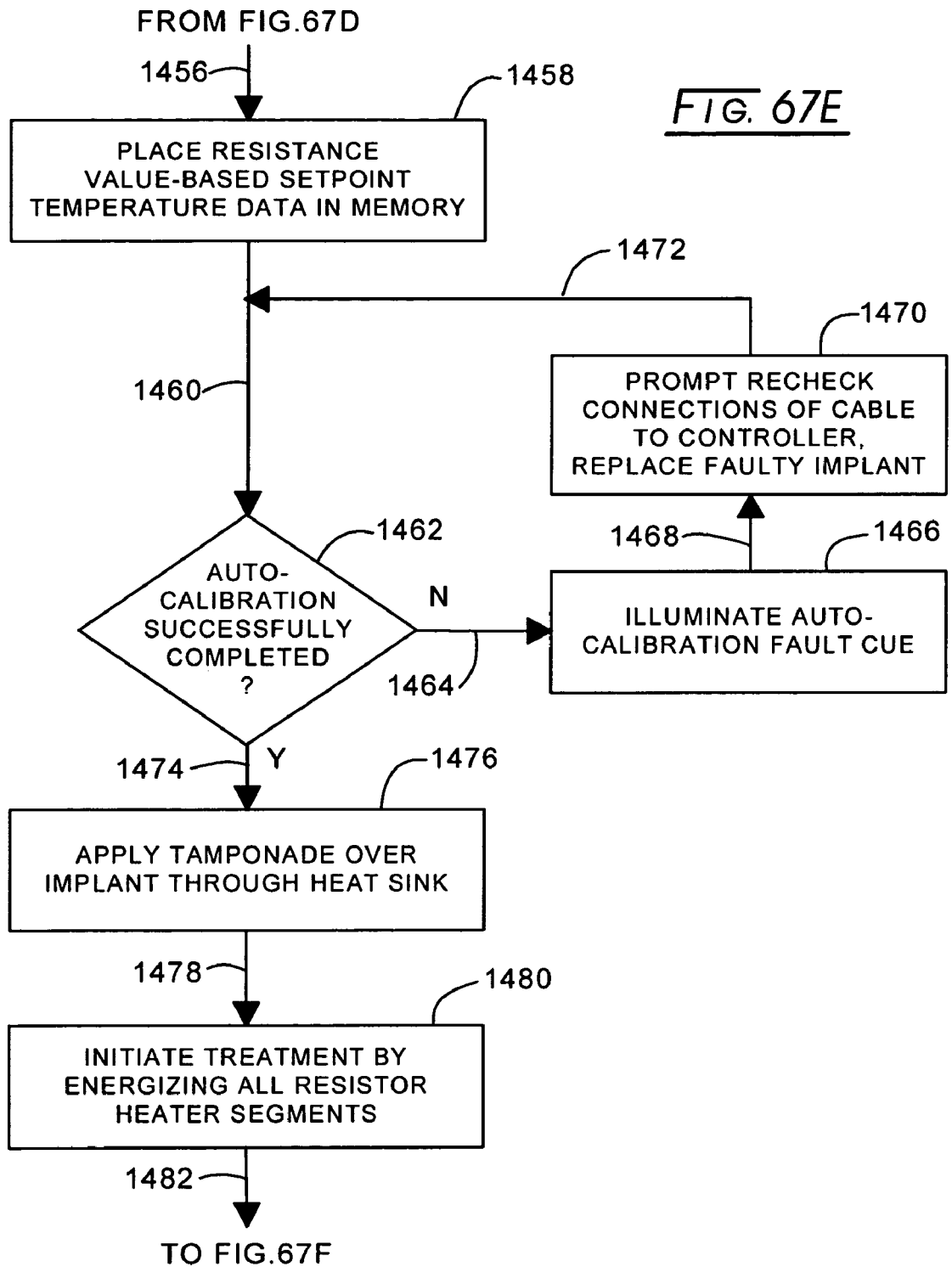

METHOD AND APPARATUS FOR CARRYING OUT THE CONTROLLED HEATING OF TISSUE IN THE REGION OF DERMIS

CROSS-REFERENCE TO RELATED APPLICATIONS

Continuation-in-part of application for U.S. patent Ser. No. 11/298,420 filed Dec. 9, 2005, now U.S. Pat. No. 7,613,523.

STATEMENT REGARDING FEDERALLY SPONSORED RESEARCH

Not applicable.

BACKGROUND

The skin or integument is a major organ of the body present as a specialized boundary lamina, covering essentially the entire external surface of the body, except for the mucosal surfaces. It forms about 8% of the body mass with a thickness ranging from about 1.5 to about 4 mm. Structurally, the skin organ is complex and highly specialized as is evidenced by its ability to provide a barrier against microbial invasion and dehydration, regulate thermal exchange, act as a complex sensory surface, and provide for wound healing wherein the epidermis responds by regeneration and the underlying dermis responds by repair (inflammation, proliferation, and remodeling), among a variety of other essential functions.

Medical specialties have evolved with respect to the skin, classically in connection with restorative and aesthetic (plastic) surgery. Such latter endeavors typically involve human aging. The major features of the skin are essentially formed before birth and within the initial two to three decades of life are observed to not only expand in surface area but also in thickness. From about the third decade of life onward there is a gradual change in appearance and mechanical properties of the skin reflective of anatomical and biological changes related to natural aging processes of the body. Such changes include a thinning of the adipose tissue underlying the dermis, a decrease in the collagen content of the dermis, changes in the molecular collagen composition of the dermis, increases in the number of wrinkles, along with additional changes in skin composition. The dermis itself decreases in bulk, and wrinkling of senescent skin is almost entirely related to changes in the dermis. Importantly, age related changes in the number, diameter, and arrangement of collagen fibers are correlated with a decrease in the tensile strength of aging skin in the human body, and the extensibility and elasticity of skin decrease with age. Evidence indicates that intrinsically aged skin shows morphological changes that are similar in a number of features to skin aged by environmental factors, including photoaging.

See generally:
1. Gray's Anatomy, 39th Edition, Churchill Livingstone, N.Y. (2005)
2. Rook's Textbook of Dermatology, 7th Edition, Blackwell Science, Malden, Mass. (2004)

A substantial population of individuals seeking to ameliorate this aging process has evolved over the decades. For instance, beginning in the late 1980s researchers who had focused primarily on treating or curing disease began studying healthy skin and ways to improve it and as a consequence, a substantial industry has evolved. By reducing and inhibiting wrinkles and minimizing the effects of ptosis (skin laxity and sagging skin) caused by the natural aging of collagen fibrils within the dermis, facial improvements have been realized with the evolution of a broad variety of corrective approaches.

Considering its structure from a microscopic standpoint, the skin is composed of two primary layers, an outer epidermis which is a keratinized stratified squamous epithelium, and the supporting dermis which is highly vascularized and provides supporting functions. In the epidermis tissue there is a continuous and progressive replacement of cells, with a mitotic layer at the base replacing cells shed at the surface. Beneath the epidermis is the dermis, a moderately dense connective tissue. The epidermis and dermis are connected by a basement membrane or basal lamina with greater thickness formed as a collagen fiber which is considered a Type I collagen having an attribute of shrinking under certain chemical or heat influences. Lastly, the dermis resides generally over a layer of contour defining subcutaneous fat. Early and some current approaches to the rejuvenation have looked to treatments directed principally to the epidermis, an approach generally referred to ablative resurfacing of the skin. Ablative resurfacing of the skin has been carried out with a variety of techniques. One approach, referred to as "dermabrasion" in effect mechanically grinds off components of the epidermis.

Mechanical dermabrasion activities reach far back in history. It is reported that about 1500 B.C. Egyptian physicians used sandpaper to smooth scars. In 1905 a motorized dermabrasion was introduced. In 1953 powered dental equipment was modified to carry out dermabrasion practices. See generally:
  3. Lawrence, et al., "History of Dermabrasion" Dermatol Surg 2000; 26:95-101

A corresponding chemical approach is referred to by dermatologists as "chemical peel". See generally:
  4. Moy, et al., "Comparison of the Effect of Various Chemical Peeling Agents in a Mini-Pig Model" Dermatol Surg 1996; 22:429-432

Another approach, referred to as "laser ablative resurfacing of skin" initially employed a pulsed $CO_2$ laser to repair photo-damaged tissue which removed the epidermis and caused residual thermal damage within the dermis. It is reported that patients typically experienced significant side effects following this ablative skin resurfacing treatment. Avoiding side effects, non-ablative dermal remodeling was developed wherein laser treatment was combined with timed superficial skin cooling to repair tissue defects related to photo-aging. Epidermal removal or damage thus was avoided, however, the techniques have been described as having limited efficacy. More recently, fractional photothermolysis has been introduced wherein a laser is employed to fire short, low energy bursts in a matrix pattern of non-continuous points to form a rastor-like pattern. This pattern is a formation of isolated non-continuous micro-thermal wounds creating necrotic zones surrounded by zones of viable tissue. See generally:
  5. Manstein, et al., "Fractional Photothermolysis: A New Concept for Cutaneous Remodeling Using Microscopic Patterns of Thermal Injury"; Lasers in Surgery and Medicine 34:426-438 (2004)

These ablative techniques (some investigators consider fractional photothermolysis as a separate approach) are associated with drawbacks. For instance, the resultant insult to the skin may require 4-6 months or more of healing to evolve newer looking skin. That newer looking skin will not necessarily exhibit the same shade or coloration as its original counterpart. In general, there is no modification of the dermis in terms of a treatment for ptosis or skin laxity through collagen shrinkage.

To treat patients for skin laxity, some investigators have looked to procedures other than plastic surgery. Techniques for induced collagen shrinkage at the dermis have been developed. Such shrinkage qualities of collagen have been known and used for hundreds of years, the most classic example being the shrinking of heads by South American headhunters. Commencing in the early 1900s shrinking of collagen has been used as a quantitative measure of tanning with respect to leather and in the evaluation of glues See:

6. Rasmussen, et al., "Isotonic and Isometric Thermal Contraction of Human Dermis I. Technic and Controlled Study", J. Invest. Derm. 1964; 43:333-9

Dermis has been heated through the epidermis utilizing laser technology as well as intense pulsed light exhibiting various light spectra or single wavelength. The procedure involves spraying a burst of coolant upon the skin such as refrigerated air, whereupon a burst of photons penetrates the epidermis and delivers energy into the dermis.

Treatment for skin laxity by causing a shrinkage of collagen within the dermis generally involves a heating of the dermis to a temperature of about 60° C. to 70° C. over a designed treatment interval. Heat induced shrinkage has been observed in a course of laser dermabrasion procedures. However, the resultant energy deposition within the epidermis has caused the surface of the skin to be ablated (i.e., burned off the surface of the underlying dermis) exposing the patient to painful recovery and extended healing periods which can be as long as 6-12 months. See the following publication:

7. Fitzpatrick, et al., "Collagen Tightening Induced by Carbon Dioxide Laser Versus Erbium: YAG Laser" Lasers in Surgery and Medicine 27: 395-403 (2000)

Dermal heating in consequence of the controlled application of energy in the form of light or radiofrequency electrical current through the epidermis and into the dermis has been introduced. To avoid injury to the epidermis, cooling methods have been employed to simultaneously cool the epidermis while transmitting energy through it. In general, these approaches have resulted in uncontrolled, non-uniform and often inadequate heating of the dermis layer resulting in either under-heating (insufficient collagen shrinkage) or over-heating (thermal injury) to the subcutaneous fat layer and/or weakening of collagen fibrils due to over-shrinkage. See the following publication:

8. Fitzpatrick, et al., "Multicenter Study of Noninvasive Radiofrequency for Periorbital Tissue Tightening", Lasers in Surgery in Medicine 33:232-242 (2003)

The RF approach described in publication 8 above is further described in U.S. Pat. Nos. 6,241,753; 6,311,090; 6,381,498; and 6,405,090. Such procedure involves the use of an electrode capacitively coupled to the skin surface which causes radiofrequency current to flow through the skin to a much larger return electrode located remotely upon the skin surface of the patient. Note that the electrodes are positioned against skin surface and not beneath it. The radiofrequency current density caused to flow through the skin is selected to be sufficiently high to cause resistance heating within the tissue and reach temperatures sufficiently high to cause collagen shrinkage and thermal injury, the latter result stimulating beneficial growth of new collagen, a reaction generally referred to as "neocollagenasis".

To minimize thermal energy to the underlying subcutaneous fat layer these heating methods also attempt to apply energy periods with pulse durations on the order of several nanoseconds to several thousand microseconds for laser based methods and several seconds for radiofrequency electrical current based methods. This highly transient approach to heating the collagen within the dermis also leads to a wide range of temperature variations due to natural patient-to-patient differences in the optical and electrical properties of their skin including localized variations in electrical properties of skin layers. It may be observed that the electrical properties of the dermis are not necessarily homogenous and may vary somewhat within the treatment zone, for example, because of regions of concentrated vascularity. This may jeopardize the integrity of the underlying fat layer and damage it resulting in a loss of desired facial contour. Such unfortunate result at present appears to be uncorrectable. Accordingly, uniform heating of the dermal layer is called for in the presence of an assurance that the underlying fat layer is not affected while minimal injury to the epidermis is achieved. A discussion of the outcome and complications of the noted non-ablative mono-polar radiofrequency treatment is provided in the following publication:

9. Abraham, et al., "Current Concepts in Nonablative Radiofrequency Rejuvenation of the Lower Face and Neck" Facial Plastic Surgery, Vol. 21 No. 1 (2005)

In the late 1990s, Sulamanidze developed a mechanical technique for correcting skin laxity. With this approach one or more barbed non-resorbable sutures are threaded under the skin with an elongate needle. The result is retention of the skin in a contracted state and, over an interval of time, the adjacent tissue will ingrow around the suture to stabilize the facial correction. See the following publications:

10. Sulamanidze, et al., "Removal of Facial Soft Tissue Ptosis With Special Threads", Dermatol Surg; 28:367-371 (2002)

11. Lycka, et al., "The Emerging Technique of the Antiptosis Subdermal Suspension Thread", Dermatol Surg; 30:41-44 (2004)

Eggers, et al., in application for U.S. patent Ser. No. 11/298,420 entitled "Aesthetic Thermal Sculpting of Skin", filed Dec. 9, 2005 describes a technique for directly applying heat energy to dermis with one or more elevated temperature implants providing controlled shrinkage thereof. Importantly, while this heating procedure is underway, the subcutaneous fat layer is protected by a polymeric thermal barrier. In a preferred arrangement this barrier implant is thin and elongate and supports a flexible resistive heating circuit, the metal heating components of which are in direct contact with dermis. Temperature output of this resistive heating circuit is intermittently monitored and controlled by measurement of a monitor value of resistance. For instance, resistive heating is carried out for about a one hundred millisecond interval interspersed with one millisecond resistance measurement intervals. Treatment intervals experienced with this system and technique will appear to obtain significant collagen shrinkage within about ten minutes to about fifteen minutes. During the procedure, the epidermis is cooled by blown air.

Dermis also is the situs of congenital birthmarks generally deemed to be capillary malformations historically referred to as "Port-Wine Stains" (PWS). Ranging in coloration from pink to purple, these non-proliferative lesions are characterized histologically by ecstatic vessels of capillary or venular type within the papillary and reticular dermis and are considered as a type of vascular malformation. The macular lesions are relatively rare, occurring in about 0.3% of newborns and generally appear on the skin of the head and neck within the distribution of the trigeminal (fifth cranial) nerve. They persist throughout life and may become raised, nodular, or darken with age. Their depth has been measured utilizing pulsed photothermal radiometry (PPTR) and ranges from about 200 μm to greater than 1,000 μm.

See the following publication:

12. Bincheng, et al., Accurate Measurement of Blood Vessel Depth in Port Wine Stain Human Skin in vivo Using "Photothermal Radiometry", J. Biomed. Opt. (5), 961-966 (September/October 2004).

Fading or lightening the PWS lesions has been carried out with lasers with somewhat mixed results. For instance, they have been treated with pulsed dye lasers (PDL) at 585 nm wavelength with a 0.45 ms pulse length and 5 mm diameter spot size. Cryogenic bursts have been used with the pulsing for epidermal protection. Generally, the extent of lightening achieved is evaluated six to eight weeks following laser treatment. Such evaluation assigns the color of adjacent normal skin as 100% lightening and a post clearance, evaluation of lesions will consider more than 75% lightening as good.

See the following publication:
13. Fiskerstrand, et al., "Laser Treatment of Port Wine Stains:
Thereaupetic Outcome in Relation to Morphological Parameters", Brit. J. of Derm., 134, 1039-1043, (1996).

Lesions have been classified, for instance, utilizing video microscopy, three patterns of vascular ectasia being established; type 1, ectasia of the vertical loops of the papillary plexus; type 2, ectasia of the deeper, horizontal vessels in the papillary plexus; and type 3, mixed pattern with varying degrees of vertical and horizontal vascular ectasia. In general, due to the limited depth of laser therapy, only type 1 lesions are apt to respond to such therapy.

Port wine stains also are classified in accordance with their degree of vascular ectasia, four grades thereof being recognized, Grades I to IV.

Grade 1 lesions are the earliest lesions and thus have the smallest vessels (50-80 um in diameter). Using ×6 magnification and transillumination, individual vessels can only just be discerned and appear like grains of sand. Clinically, these lesions are light or dark pink macules. Grade II lesions are more advanced (vessel diameter=80-120 um). Individual vessels are clearly visible to the naked eye, especially in less dense areas. They are thus clearly distinguishable macules. Grade III lesions are more ecstatic (120-150 um). By this stage, the space between the vessels has been replaced by the dilated vessels. Individual vessels may still be visible on the edges of the lesion or in a less dense lesion, but by and large individual vessels are no longer visible. The lesion is usually thick, purple, and palpable. Eventually dilated vessels will coalesce to form nodules, otherwise known as cobblestones. Grade IV represents the largest vessels. The main purpose of these classifications has been to assign a grade for ease in communication and determination of the appropriate laser treatment settings.

See the following publication:
14. Mihm, Jr., et al, "Science, Math and Medicine—Working Together to Understand the Diagnosis, Classification and Treatment of Port-Wine Stains", a paper presented in Mt. Tremblant, Quebec, Canada, 2004, Controversies and Conversations in Cutaneous Laser Surgery—An Advanced Symposium.

BRIEF SUMMARY

The embodiments at hand are addressed to apparatus and methods for effecting a controlled heating of tissue within the region of the dermis of skin using heater implants that are configured with a thermally insulative generally flat support functioning as a thermal barrier. One surface of this thermal barrier carries one or more heater resistor segments which are encapsulated against body fluids by adhesively mounted polymeric supports and overlays. Mounted with electrical lead assemblages exhibiting a 4-point topology, the resistor segments are intermittently poled for instantaneous resistance values which are compared with corresponding values representing setpoint temperature.

When in use, the implants are located within heating channels at the interface between skin dermis and the next adjacent subcutaneous tissue layer sometimes referred to as a contour defining fat layer. With such positioning the heater resistor segments are in an outwardly directed thermal exchange relationship with the lower region of dermis while the flat polymeric support functions as a thermal barrier importantly enhancing the protection of the next adjacent subcutaneous tissue layer from thermal vantage. Research is described showing that by applying slight pressure or tamponade to the skin surface over the implants, substantially improved conduction heat transfer from the polymerically encapsulated heater resistor segments is realized. For instance, where the implants are used for skin remodeling calling for temperature generation at or above the thermal threshold for dermis or dermis component-based skin shrinkage, the therapy interval may be of more practical duration. Control of skin surface temperature during therapy is carried out with heat sinks preferably having a conformal contact surface performing in concert with an interposed thermal energy transfer medium which typically is a liquid such as water. A preferred heat sink configuration includes a flexible, bag-like transparent polymeric container which carries a heat sinking fluid such as water. Other energy transfer mediums include water-based solutions such as isotonic saline, antimicrobial solutions as well as alcohols (isopropyl alcohol) or oils (e.g., mineral oils). Heat transfer performance of the devices is improved by agitating the liquid within the container, and a variety of techniques for such liquid action are described. The heat sinks may be employed to assert the noted tamponade and, when transparent, permit visual monitoring of the extent of remodeling skin shrinkage. Conduction heat transfer from each polymerically encapsulated resistor segment is enhanced with metal heat spreaders located upon a polymeric support immediately above each resistor segment. These spreaders may be formed with copper having a thickness within a range from about 0.005 inch to about 0.020 inch.

In general, skin remodeling is carried out with setpoint temperatures at or above the thermal threshold temperature for carrying out the shrinkage of dermis or components of dermis. Advantageously, that thermal threshold transition temperature may be reduced, for example, to the extent of about 10° C. to about 12° C. by pre-administering an adjuvant to infuse into dermis. Such adjuvant may be one or more of a salt, an enzyme, a detergent, a lipophile, a denaturing solvent, an organic denaturant, an acid solution, or a basic solution.

The implants and associated method of the invention also may be employed for the treatment of a capillary malformation sometimes referred to as "port wine stain" (PWS). For this application, the implant based heating is carried out to effect an irreversible vascular coagulation at a setpoint temperature which is atraumatic to the dermis and dpidermis.

Other features will, in part, be obvious and will, in part, appear hereinafter.

The discourse, accordingly, looks to and comprises the apparatus and method possessing the construction, combination of elements, arrangement of parts and steps which are exemplified in the following detailed disclosure.

For a fuller understanding of the nature and objects hereof, reference should be made to the following detailed description taken in connection with the accompanying drawings.

BRIEF DESCRIPTION OF THE DRAWINGS

FIG. 20 is a perspective view of a single heater resistor segment implant;

FIG. 21 is a partial perspective view of the leading end of the implant of FIG. 20;

FIG. 22 is a top view of the implant of FIG. 20;

FIG. 23 is a bottom view of the implant of FIG. 20;

FIG. 29 is a perspective view of an implant supporting four heater resistor segments;

FIG. 30 is a top view of the implant of FIG. 29;

FIG. 31 is a bottom view of the implant of FIG. 29; FIG. 32 is a partial perspective view of the leading end of the implant of FIG. 29;

FIG. 33 is a sectional view taken through the plane 33-33 shown in FIG. 30;

FIG. 34 is an enlarged broken away bottom view of the resistor segments of the implant of FIG. 29 additionally showing a 4-point lead assemblage;

FIG. 35 is a still further enlarged bottom view of the resistor segment and lead assemblage of the implant of FIG. 29 showing the lead components located at the trailing end of the implant;

FIG. 36 is a perspective view of another implant according to the invention which incorporates thermal spreaders;

FIG. 37 is a top view of the implant of FIG. 36;

FIG. 39 is a bottom view of the implant of FIG. 36;

FIG. 42 is a partial perspective view of the connector guide shown in FIG. 40 and further showing its connection with a cable connector;

FIG. 43 is a sectional view taken through the plane 43-43 shown in FIG. 42;

FIG. 44 is a top view of a blunt dissector introducer;

FIG. 45 is a side view of the introducer of FIG. 44;

FIG. 61 is a top view of a bladed implant;

FIG. 62 is a perspective view of a blunt dissection blade employed with implants as at FIG. 61;

FIG. 63 is a partial top view of a thermal barrier within which a blade component as shown in FIG. 62 has been embedded;

FIG. 64 is a sectional view taken through the plane 64-64 shown in FIG. 63;

FIG. 65A is a schematic top view of an implant of predetermined length supporting four heater resistor segments of about 15 mm length;

FIG. 65B is a schematic top view of another implant having the same predetermined length but supporting four heater resistor segments of length of about 12 mm;

FIG. 65C is a schematic top view of an implant having the same length as the implant shown in FIGS. 65A and 65B but showing four heater resistor segments having a length of about 8 mm;

FIGS. 66A-66J combine as labeled thereon to provide a flowchart of procedure according to the invention for carrying out shrinkage of collagen at dermis; and FIGS. 67A-67H combine as labeled thereon to provide a flowchart illustrating procedures for carrying out thermal treatment of a capillary malformation lesion.

DETAILED DESCRIPTION

The discourse to follow will reveal that the implants and method described were evolved over a sequence of animal (pig) experiments, both ex vivo and in vivo. This work involved the utilization of radiofrequency excited bipolar electrodes combined with an electrically and thermally insulative support and shield as well as with resistor segment-based implants also provided with a noted thermal and electrically insulative shield and support. Certain of the experiments and their results are described to, in effect, set forth a form of development history giving an insight into the reasoning under which the instant method and apparatus developed.

The arrangement of the physical structure of the dermis is derived in large part from the structure of the extra cellular matrix surrounding the cells of the dermis. The term extra cellular matrix refers collectively to those components of a tissue such as the dermis that lie outside the plasma membranes of living cells, and it comprises an interconnected system of insoluble protein fibers, cross-linking adhesive glycoproteins and soluble complexes of carbohydrates and carbohydrates covalently linked to proteins (e.g. proteoglycans). A basement membrane lies at the boundary of the dermis and epidermis, and is structurally linked to the extracellular matrix of the dermis and underlying hypodermis. Thus the extracellular matrix of the dermis distributes mechanical forces from the epidermis and dermis to the underlying tissue.

Figure 1:
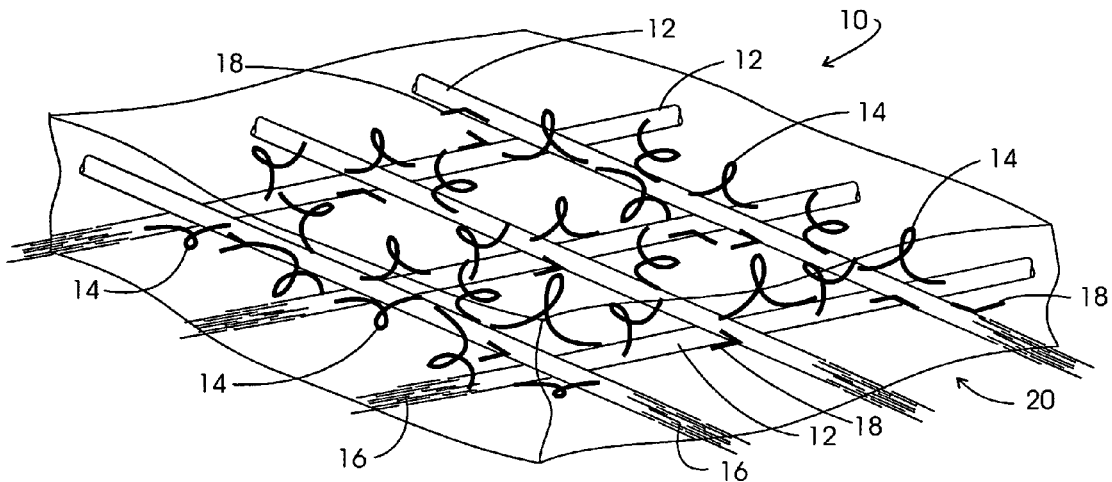
FIG. 1 is a diagram of the structure of the extra cellular matrix of dermis tissue.

Looking to FIG. 1, a schematic representation of a region of the extracellular matrix of the dermis is represented generally at 10. The insoluble fibers include collagen fibers at 12, most commonly collagen Type I, and elastin at 14. The fundamental structural unit of collagen is a long, thin protein (300 nm×15 nm) composed of three subunits coiled around one another to form the characteristic right-handed collagen triple helix. Collagen is formed within the cell as procollagen, wherein the three subunits are covalently cross linked to one another by disulphide bonds, and upon secretion are further processed into tropocollagen. The basic tropocollagen structure consists of three polypeptide chains coiled around each other in which the individual collagen molecules are held in an extended conformation. The extended conformation of a tropocollagen molecule is maintained by molecular forces including hydrogen bonds, ionic interactions, hydrophobicity, salt links and covalent cross-links. Tropocollagen molecules are assembled in a parallel staggered orientation into collagen fibrils at 16, each containing a large number of tropocollagens, held in relative position by the above listed molecular forces and by cross-links between hydrolysine residues of overlapping tropocollagen molecules. Certain aspects of collagen stabilization are enzyme mediated, for example by Cu-dependent lysyl oxidase. Collagen fibrils are typically of about 50 nm in diameter. Type I collagen fibrils have substantial tensile strength, greater on a weight basis than that of steel, such that the collagen fibril can be stretched without breaking. Collagen fibrils are further aggregated into more massive collagen fibers, as previously shown at 12. The aggregation of collagen fibers involves a variety of molecular interactions, such that it appears that collagen fibers may vary in density based on the particular interactions present when formed. Elastin, in contrast to collagen, does not form such massive aggregated fibers, may be thought of as adopting a looping conformation (as shown at 14) and stretch more easily with nearly perfect recoil after stretching.

The extracellular matrix (ECM) as at 10 lies outside the plasma membrane, between the cells forming skin tissue. The components of the ECM including tropocollagen, are primarily synthesized inside the cells and then secreted into the ECM through the plasma membrane. The overall structure and anatomy of the skin, and in particular the dermis, are determined by the close interaction between the cells and ECM. Referring again to FIG. 1, only a few of the many and diverse components of the ECM are shown. In addition to collagen fibers 12 and elastin 14 are a large number of other components that serve to crosslink or cement these named components to themselves and to other components of the ECM. Such crosslinking components are represented generally as at 18, and may be of protein, glycoprotein and or carbohydrate composition, for example. The cross linked collagen fibers shown in FIG. 1 are embedded in a layer of highly hydrated material, including a diverse variety of modified carbohydrates, including particularly the large carbohydrate hyaluronic acid (hyaluronan) and chondroitin sulphate. Hyaluronan is a very large, hydrated, non-sulphated mucopolysaccharide that forms highly viscous fluids. Chondroitin sulphate is a glycosaminoglycan component of the ECM. Thus the volume of the ECM as represented generally at 20 is filled with a flexible gel with a hydrated hyaluronan component that surrounds and supports the other structural components such as collagen and elastin. Thus the structural form of the dermis may be thought to be composed of collagen, providing tensile strength, with the collagen being held in place within a matrix of hyaluronan, which resists compression. Underlying this structure are the living cells of the dermis, which in response to stimuli (such as wounds or stress, for instance) can be induced to secrete additional components, synthesize new collagen (i.e. neocollagenesis), and otherwise alter the structural form of the ECM and the skin itself. The structure of the collagen reinforced connective tissues should not be considered entirely static, but rather that the net accumulation of collagen connective tissues is an equilibrium between synthesis and degradation of the components of the collagen reinforced connective tissues. Similarly, the other components of the ECM are modulated in response to environmental stimuli.

Figure 2:
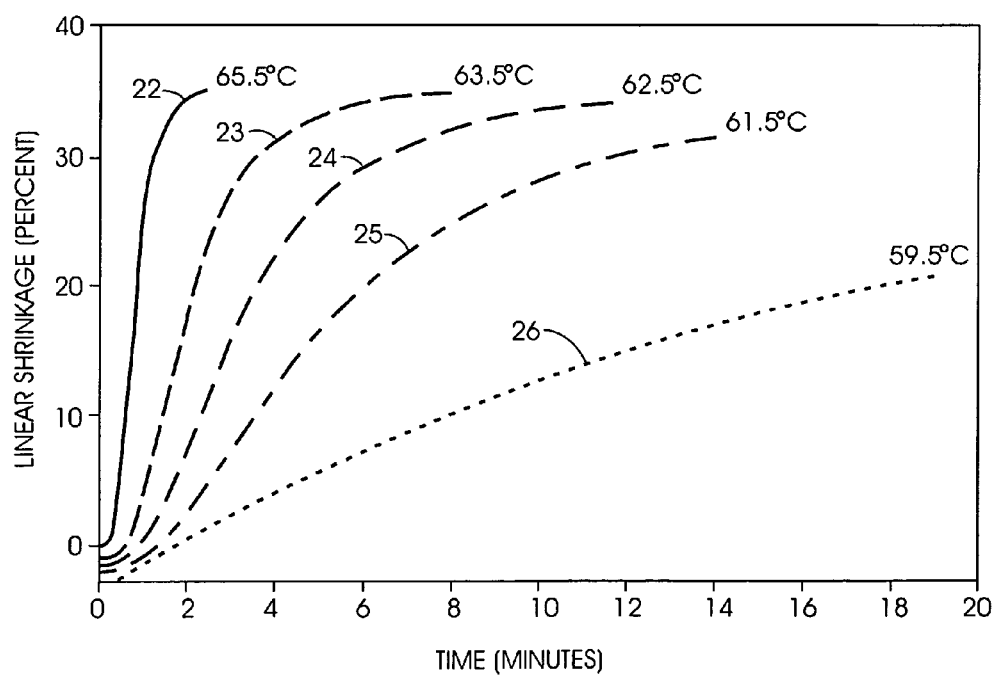
FIG. 2 is a family of curves relating linear shrinkage of dermis with time and temperature.

As noted earlier previous researchers have shown that collagen fibers can be induced to shrink in overall length by application of heat. Experimental studies have reported that collagen shrinkage is, in fact, dependent upon the thermal dose (i.e., combination of time and temperature) in a quantifiable manner. (See publication 15, infra). Looking to FIG. 2, a plot of linear collagen shrinkage versus time for various constant temperatures is revealed in association with plots or lines 22-26. For instance, at line 24, linear shrinkage is seen to be about 30% for a temperature of 62.5° C. held for a ten minute duration. Curve 24 may be compared with curve 22 where shrinkage of about 36% is achieved in very short order where the temperature is retained at 65.5° C. Correspondingly, curve 26 shows a temperature of 59.5° C. and a very slow rate of shrinkage, higher levels thereof not being reached. Clinicians generally would prefer a shrinkage level on the order of 10% to 20% in dealing with skin laxity.

Figure 3:
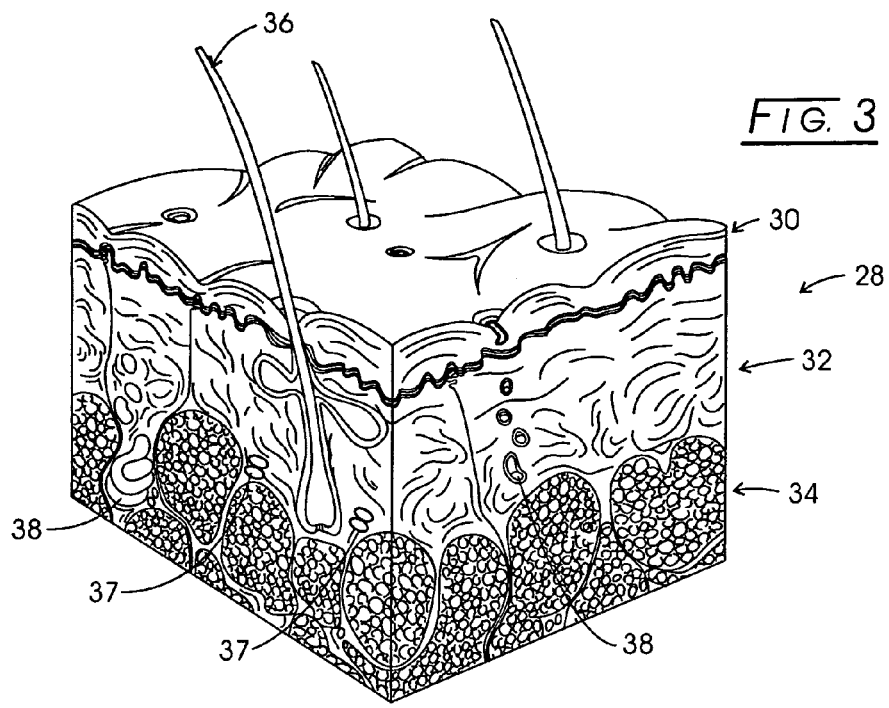
FIG. 3 is a schema representing the organization of skin.

FIG. 3 reveals a schema representing the organization of skin. Shown generally at 28, the illustrated skin structure is one of two major skin classes of structure and functional properties representing thin, hairy (hirsute) skin which constitutes the great majority of the body's covering. This is as opposed to thick hairless (glabrous) skin from the surfaces of palms of hands, soles of feet and the like. In the figure, the outer epidermis layer 30 is shown generally extending over the dermis layer represented generally at 32. Dermis 32, in turn, completes the integument and is situated over an adjacent subcutaneous tissue layer (or hypodermis) represented generally at 34. Those involved in the instant subject matter typically refer to this adjacent subcutaneous tissue layer 34 which typically has a substantial adipose tissue component as a "fat layer" or "fatty layer," and this next adjacent subcutaneous tissue layer is also called the "hypodermis" by some artisans. The figure also reveals a hair follicle and an associated shaft of hair 36, vascular structures 37 feeding the dermis 32 and sweat glands 38. Not shown in FIG. 3 are a number of other components, including the cellular structure of the dermis, and the vascular tissues supplying the vascularized dermis and its overlying epidermis.

Epidermis 30 in general comprises an outer or surface layer, stratum corneum composed of flattened, cornified non-nucleated cells. This surface layer overlays a granular layer, stratum granulosum composed of flattened granular cells which, in turn, overlays a spinous layer, stratum spinosum composed of flattened polyhedral cells with short processes or spines and, finally, a basal layer, stratum basale, composed columnar cells arranged perpendicularly. For the type skin 28, the epidermis will exhibit a thickness from 0.07 to 0.15 mm. Heating implants according to the invention will be seen to be contactable with the dermis 32 at a location representing the interface between dermis 32 and next adjacent subcutaneous tissue or fat layer 34. The dermis in general comprises a papillary layer, subadjacent to the epidermis, and supplying mechanical support and metabolic maintenance of the overlying epidermis. The papillary layer of the dermis is shaped into a number of papillae that interdigitate with the basal layer of the epidermis, with the cells being densely interwoven with collagen fibers. The reticular layer of the dermis merges from the papillary layer, and possesses bundles of interlacing collagen fibers (as shown in FIG. 1) that are typically thicker than those in the papillary layer, forming a strong, deformable three dimensional lattice around the cells of the reticular dermis. Generally, the dermis is highly vascularized, especially as compared to the avascular epidermis. The dermis layer 32 will exhibit a thickness of from about 1.0 mm to about 4.0 mm.

For the purposes of the discourse, "intradermal" is defined as within the dermis layer of the skin itself. "Subcutaneous" has the common definition of being below the skin, i.e. near, but below the epidermis and dermis layers. "Subdermal" is defined as a location immediately interior to, or below the dermis, at the interface between the dermis and the next adjacent subcutaneous layer sometimes referred to as hypodermis. "Hypodermal" is defined literally as under the skin, and refers to an area of the body below the dermis, within the hypodermis, and is usually not considered to include the subadjacent muscle tissue. "Peridermal" is defined as in the general area of the dermis, whether intradermal, subdermal or hypodermal. Transdermal is defined in the art as "entering through the dermis or skin, as in administration of a drug applied to the skin in ointment or patch form," i.e. transcutaneous. A topical administration as used herein is given its typical meaning of application at skin surface.

As noted, the thickness of the epidermis and dermis vary within a range of only a few millimeters. Thus subcutaneous adipose tissue is responsible in large part for the overall contours of the skin surface, and the appearance of the individual patient's facial features, for instance. The size of the adipose cells may vary substantially, depending on the amount of fat stored within the cells, and the volume of the adipose tissue of the hypodermis is a function of cell size rather than the number of cells. The cells of the subcutaneous adipose tissue, however, have only limited regenerative capability, such that once killed or removed, these cells are not typically replaced. Any treatment modality seeking to employ heat to shrink the collagen of the ECM of the skin, must account for the risk associated with damaging or destroying the subcutaneous adipose layer, with any such damage representing a large risk of negative aesthetic effects on the facial features of a patient.

In general, the structural features of the dermis are determined by a matrix of collagen fibers forming what is sometimes referred to as a "scaffold." This scaffold, or matrix plays an important role in the treatment of skin laxity in that once shrunk, it must retain it's position or tensile strength long enough for new collagen evolved in the healing process to infiltrate the matrix. That process is referred to as "neocollagenesis." Immediately after the collagen scaffold is heated and shrunk it is no longer vital because it has been exposed to a temperature evoking an irreversible denaturation. Where the scaffold retains adequate structural integrity in opposition to forces that would tend to pull it back to its original shape, a healing process requiring about four months will advantageously occur. During this period of time, neocollagenesis is occurring, along with the deposition and cross linking of a variety of other components of the ECM. In certain situations, collagen is susceptible to degradation by collagenase, whether native or exogenous.

Studies have been carried out wherein the mechanical properties of collagen as heated were measured as a function of the amount of shrinkage induced. The results of one study indicated that when the amount of linear shrinkage exceeds about 20%, the tensile strength of the collagen matrix or scaffold is reduced to a level that the contraction may not be maintained in the presence of other natural restorative forces present in tissue. Hence, with excessive shrinkage, the weakened collagen fibrils return from their now temporary contracted state to their original extended state, thereby eliminating any aesthetic benefit of attempted collagen shrinkage. The current opinion of some investigators is that shrinkage should not exceed about 25%.

One publication reporting upon such studies describes a seven-parameter logistic equation (sigmoidal function) modeling experimental data for shrinkage, S, in percent as a function of time, t, in minutes and temperature, T, in degrees centigrade. That equation may be expressed as follows:

$$S(t, T) = \frac{[a_0(T-62) + a_1] - a_2}{1 + \left(\frac{t}{a_3 e^{-a[T-62]}}\right)^{(a_4(T-62)+a_5)}} + a_2 \quad (1)$$

Equation (1) may, for instance, be utilized to carry out a parametric analysis relating treatment time and temperature with respect to preordained percentages of shrinkage. For example, where shrinkage cannot be observed by the clinician then a time interval of therapy may be computed on a preliminary basis. For further discourse with respect to collagen matrix shrinkage, temperature and treatment time, reference is made to the following publication:

15. Wall, et al., "Thermal Modification of Collagen" Journal of Shoulder and Elbow Surgery; 8:339-344 (1999)

In the course of studies leading to the instant embodiments, collateral experimentation had been undertaken exploring a system wherein dermis would be heated by radiofrequency current passing between bipolar arranged electrodes located at the interface between dermis and the next subcutaneous tissue or fat layer. That experimentation was accompanied by experimental studies utilizing similar positioning of resistively heated implants. To protect that subcutaneous layer, the electrodes, as well as resistor heaters, were supported upon a polymeric thermal barrier. That barrier support was formed of a polymeric resin such as polyetherimide available under the trade designation "Ultem" from the plastics division of General Electric Company of Pittsfield, Mass. Initially, testing with both the radiofrequency resistor-heater approaches was carried out ex vivo utilizing untreated pigskin harvested about 6-8 hours prior to experimentation. Such skin was available from a facility of the Bob Evans organization in Xenia, Ohio. To position the implant at the interface between dermis and fat layer, a blunt dissecting instrument was employed to form a heating channel, whereupon the implant was inserted over the instrument within that channel with its electrodes located for contact with dermis while the polymeric thermal barrier functioned to protect the mixed subcutaneous or fatty layer. It may be noted that such polymeric material is both thermally and electrically insulative. Following implant positioning, the instrument was removed.

Figure 4:
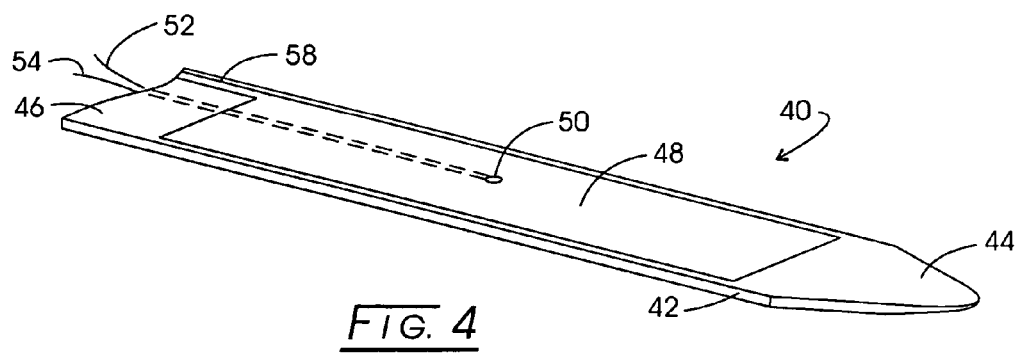
FIG. 4 is a perspective view of an experimental implant combining a thermal barrier, platinum electrode and thermocouple.
Figure 5:
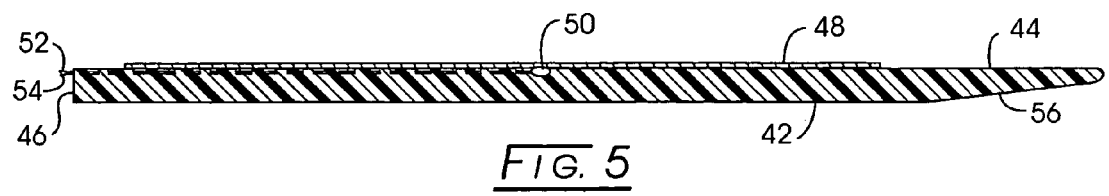
FIG. 5 is a sectional view taken through the plane 5-5 shown in FIG. 4.

Looking to FIG. 4, the initial, radiofrequency energized experimental implant is represented generally at 40. Implant 40 was configured with a polymeric electrically and thermally insulative support and barrier 42 having a tapering leading end represented generally at 44 and a trailing end represented generally at 46. Thermal barrier 42 had a thickness of 0.037 inch and a width of 0.150 inch. Adhesively bonded to the support surface of barrier 42 was a platinum foil electrode 48. Electrode 48 had a thickness of 0.001 inch, a width of 0.150 inch and was 1.0 inch long. Looking additionally to FIG. 5, a thermocouple 50 was located in electrically insulative but thermally responsive relationship with the electrode 48. Electrically insulated leads 52 and 54 extended from operable connection with thermocouple 50 outwardly from the trailing end 46 of thermal barrier 42. FIG. 5 further reveals that the leading end 44 of thermal barrier 42 is upwardly tapered as represented in general at 56. Taper 56 tended to mechanically bias the implant toward contact with the dermis when inserted within a heating channel. The integrally formed lead extending to electrode 48 at trailing end region 46 is seen at 58.

Figure 6:
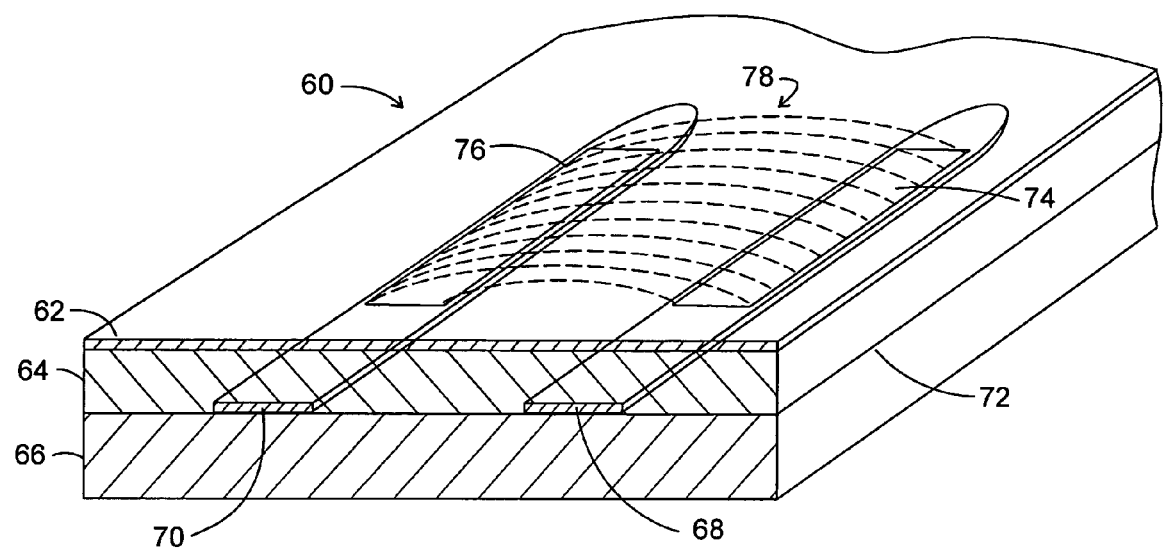
FIG. 6 is a schematic and perspective representation of ex vivo experimentation utilizing two implants as described in connection with FIGS. 4 and 5.
Figure 7:
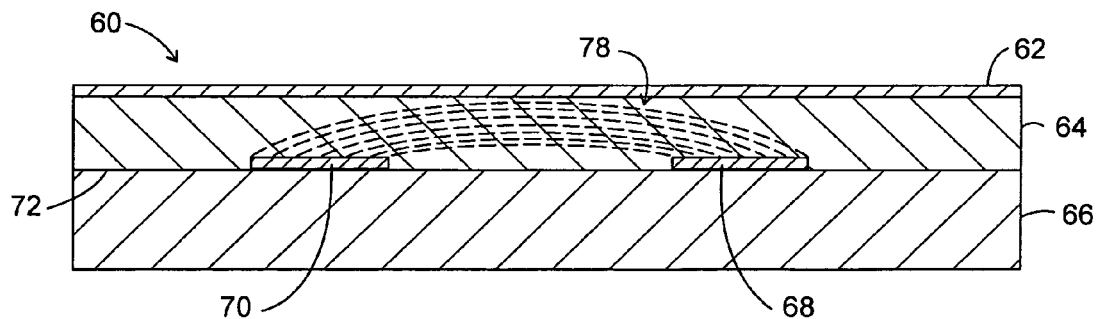
FIG. 7 is an end view of the schematic representation of FIG. 6.

Turning to FIGS. 6 and 7, a schematic portrayal is provided of the ex vivo experimental set-up utilizing implants as at 40. In the figures, harvested pigskin is represented generally at 60 having an outer epidermis layer 62; a dermis layer 64; and a next subcutaneous tissue layer or fat layer 66. Two spaced apart and parallel implants 68 and 70 are located within heating channels at the interface 72 between dermis layer 64 and fat layer 66. Thus positioned, the identically dimensioned platinum electrodes shown respectively at 74 and 76 with respect to implants 68 and 70 in FIG. 6 were located in parallel adjacency. The implants 68 and 70 were spaced apart a distance of 15 mm center-to-center. Note with the arrangement shown, the electrodes 74 and 76 are contactable with the bottom of dermis layer 64. Radiofrequency energy was applied in bipolar fashion to electrodes 74 and 76 to generate a current flux represented generally by dashed lines 78. Note that this current flux is represented as being confined to dermis layer 64. In this regard, it may be observed that the electrical conductivity exhibited at dermis layer 64 is about 5-10 times the electrical conductivity of the next adjacent fat layer 66. It was determined that to achieve significant collagen shrinkage the dermis should reach thermal transition temperatures of from about 62° C. to about 67° C. Those temperatures were found to be reachable in 50 to 60 seconds with the radiofrequency excited implants.

Figure 8:
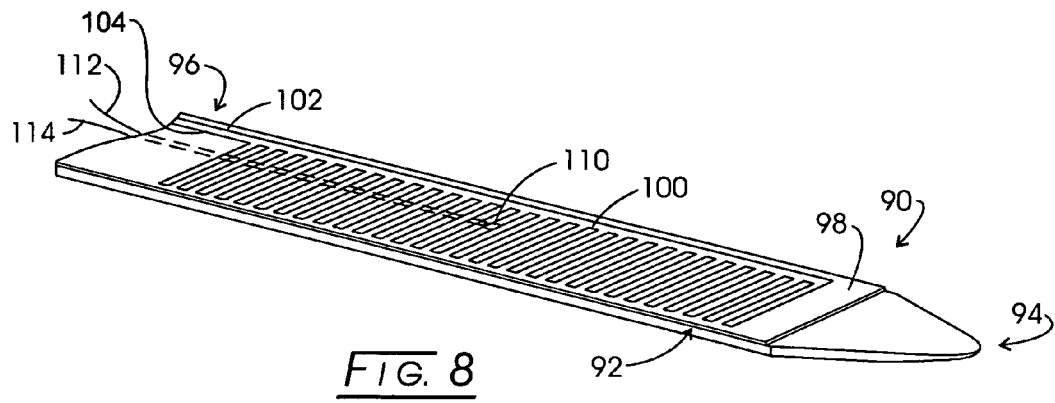
FIG. 8 is a perspective view of an experimental implant combining a thermal barrier, heater resistor and thermocouple.
Figure 9:
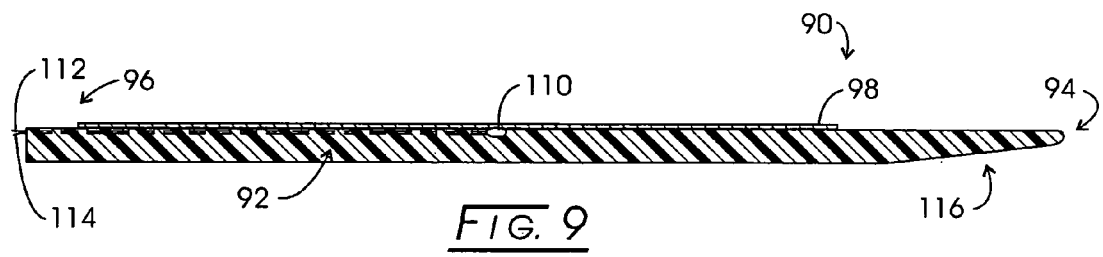
FIG. 9 is a sectional view taken through the plane 9-9 shown in FIG. 8.

Now turning to FIG. 8, another experimental implant is represented generally at 90. Implant 90 is configured with a polymeric electrically and thermally insulative support and barrier shown generally at 92 having a tapering leading end represented generally at 94 and a trailing end represented generally at 96. Thermal barrier and support 92 had a thickness of 0.037 inch and a width of 0.150 inch. Adhesively bonded to the support surface of the support or barrier 92 is a polyimide substrate 98. Substrate 98 was provided as a material sold under the trade designation "Kapton", while the support 92 may be provided as a polyetherimide under the trade designation "Ultem". Deposited upon the substrate 98 is a rectangular serpentine resistor 100 having energization leads 102 and 104 extending to trailing end 106. Formed of gold-plated copper, the resistor 100 generally was provided as a metal exhibiting a temperature coefficient of resistance greater than about 2000 ppm/° C. Device 100 had a width of about 3 mm and a length of about 29 mm. Looking additionally to FIG. 9, a thermocouple 110 was located in electrically insulative but thermally responsive relationship with the resistor 100. Electrically insulated leads 112 and 114 extended from operable connection with the thermocouple 110 outwardly from the trailing end 96 of thermal barrier or support 92. FIG. 9 further reveals that the leading end 94 of thermal barrier 92 is upwardly tapered as represented in general at 116.

Figure 10:
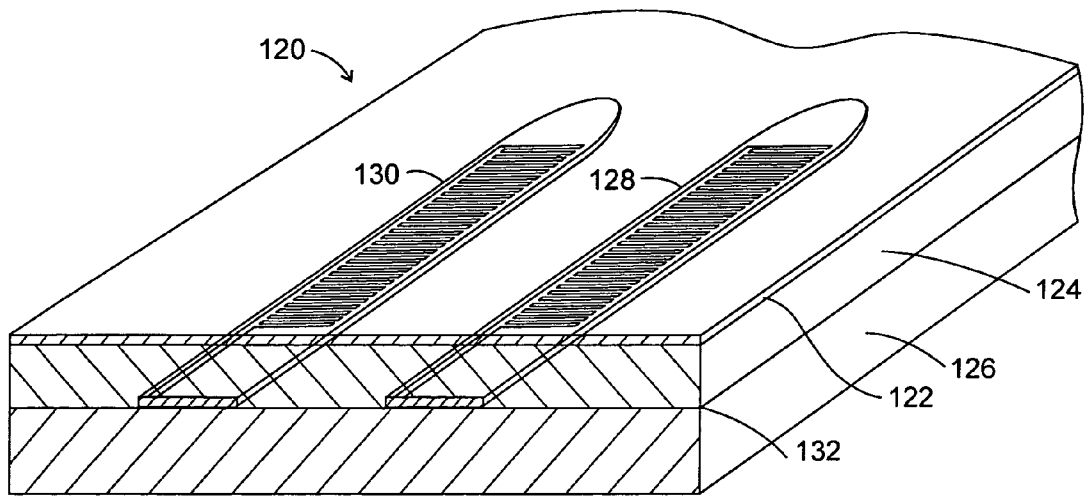
FIG. 10 is a schematic and perspective representation of ex vivo experimentation utilizing two implants as described in connection with FIGS. 8 and 9.
Figure 11:
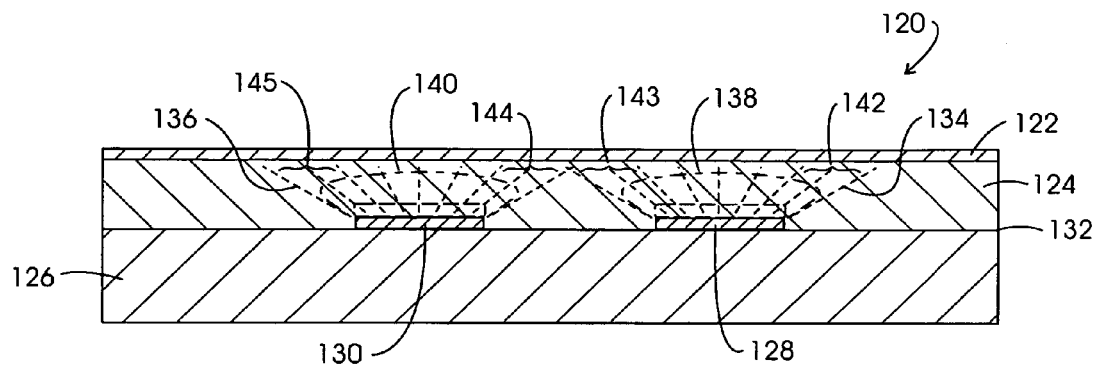
FIG. 11 is an end view of the schematic representation of FIG. 10.

Referring to FIGS. 10 and 11, a schematic portrayal is provided of the ex vivo experimental set-up utilizing resistor carrying implants as at 90. In the figures, harvested pig skin is represented generally at 120 having an outer epidermis layer 122; a dermis layer 124; and a next adjacent subcutaneous tissue layer or fat layer 126. Two spaced apart and parallel resistor carrying implants 128 and 130 are located within heating channels at the interface 132 between dermis layer 124 and next adjacent subcutaneous tissue layer 126.

Implants 128 and 130 are spaced apart edge-to-edge 5 mm and, having a width of about 3 mm are spaced apart center-to-center 8 mm. For example, d.c. current is used to energize the resistor components of implants 128 and 130, for example, toward a setpoint temperature of 75° C. Conduction heat transfer occurs into dermis from the resistors of implants 128 and 130 as shown by respective heat migration lines 134 and 136 in FIG. 11. For illustrative purposes, the conduction heat transfer from the resistor components may be designated as a zone A as represented by the somewhat elliptically-shaped dashed boundaries 138 and 140 with respective implants 128 and 130. Extending about 2 mm outboard of the edges of implants 128 and 130 is a zone B of conduction heat transfer as represented by brackets 142-145.

Initial trials with implants as at 90 were carried out with an air cooling arrangement for the epidermis surface 122. In general, about 15 minutes was required to obtain about a 10% shrinkage with a measured thermal power input to dermis in a range of about 1 to 1.3 watts per implant.

Experimentation carried out utilizing radiofrequency excited bipolar implants as at 40 led to process information resulting in improved performance for both radiofrequency excited electrodes and resistor carrying implants as at 90. Early experimental runs utilizing platinum electrodes as at 48 (FIG. 4) resulted in a significant collagen shrinkage within about a 60-90 second interval. For some of these experimental runs, the temperatures of the bipolar associated platinum electrodes were unusually separated in level. In this regard, for some runs one electrode (thermocouple) would exhibit a maximum temperature of 50° C. which is below the threshold or thermal transition temperatures for inducing shrinkage. It was observed that the thermal expansion coefficient of the polyetherimide thermal barrier 42 was $56 \times 10^{-6}$ in/in/° C. and the corresponding thermal expansion coefficient for platinum was $9 \times 10^{-6}$ in/in/° C. This meant that the thermal barrier would expand about 0.004 inch more than the platinum electrode at temperatures of about 70° C-80° C. This situation was born out by immersing the implants in water at about 80° C. to about 85° C. The implant was seen to immediately curve. Such curving will always be concavely away from the lower surface of dermis. By contrast, immersion of a resistor carrying heater implant formed with a very thin deposition of gold-plated copper on a substrate adhered to the polyetherimide material showed no warpage. This lead to an awareness that performance of the system would be affected by a loss of uniform contact between the radiofrequency excited electrodes and the surface of dermis.

Figure 12:
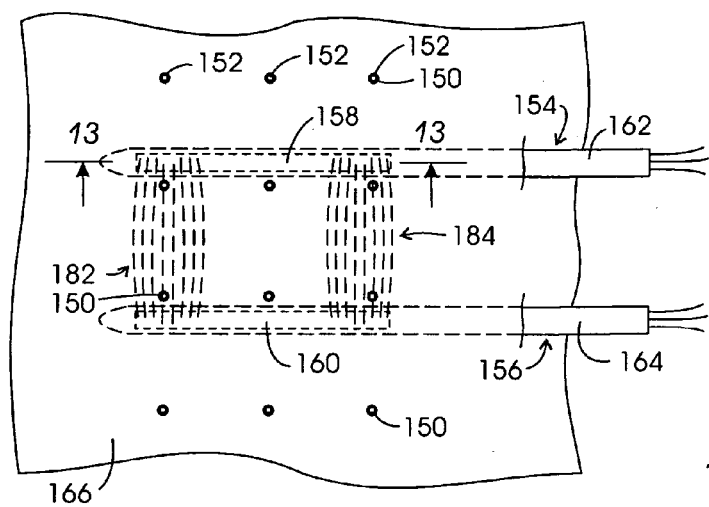
FIG. 12 is a top schematic view of an experimental procedure wherein current flux concentrations were determined to be present.

Referring to FIG. 12, a schematic representation of experimental runs is depicted. To quantify the extent of contraction or shrinkage during these trials, a matrix-like pattern of dots or visible indicia were positioned initially at the skin region of interest. In FIG. 12, the initial position of those dots are represented by black circles certain of which are identified at 150. Digital imaging of the dots 150 was carried out in this initial position at time zero. That imaging was digitally memorized as represented by the small white squares certain of which are identified at 152. In FIG. 12 those squares are centered within the dots 150. During an experimental run, the squares 152 will, as a digital image remain in position, however, as a consequence of heat induced dermis shrinkage, dots 150 will move with respect to square 152 to permit quantification of contraction or shrinkage.

Certain of the tests carried out during the collateral, R.F. activities revealed the presence of thermal injury to the epidermis such as erythema and/or edema at regions of the epidermis above forward and rearward regions of the platinum electrodes as at 48 described in connection with FIG. 4.

Looking to FIG. 12, paired implants as described at 40 are represented generally at 154 and 156. The electrodes for these implants are shown respectively in phantom at 158 and 160. Electrodes 158 and 160 are adhesively mounted upon respective thermal barriers or supports 162 and 164. Looking additionally to FIG. 13, the implant 154 reappears in sectional fashion as being located within a skin region incorporating epidermis 166, dermis 168 and next adjacent subcutaneous tissue or fat layer 170. Implant 154 is seen to be located at the interface 172 between dermis 168 and next adjacent subcutaneous tissue layer 170. Note that the implant 154 is concavely bowed away from the dermis at its central region represented generally at 176 defining a gap 178 spacing the central portion of the electrode from the dermis layer 168. Of particular importance to the instant subject matter, it was further observed that the dermis layer 168 itself contracted away from contact with the electrode as seen generally at 180. Returning to FIG. 12, this phenomena wherein the outward regions of the electrodes 158 and 160 were the only regions contacting dermis resulted in a concentration of current flux between the electrodes as illustrated at dashed current flux path representations shown generally at 182 and 184. This collateral R.F.-based effort lead to the utilization of slight compression or tamponade in conjunction with resistance heater-based implants as are described herein.

Figure 13:
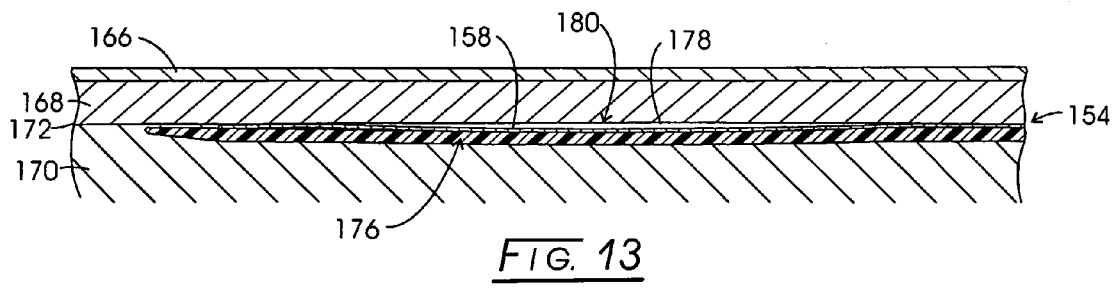
FIG. 13 is a sectional view taken through the plane 13-13 in FIG. 12.

The situation observed with respect to FIGS. 12 and 13 led to a consideration that tamponade or some form of slight pressure could be applied to the epidermis 166 to force a continuous contact between the upward surface of electrode 158 and dermis 168. To that time, the epidermis as at 166 was cooled by blown air or mist and it was consistently found that the airflow rate could not adjust fast enough nor provide cooling rates adequate for radiofrequency heating methods because of the higher heating rates per unit area and associated fast transient heat-up rate of the skin surface. Often, the surface temperature of the skin would be over-cooled resulting in insufficient shrinkage or under-cooled resulting in burns at the skin surface. This form of cooling of the skin surface in conjunction with the use of implants as at 90 also was determined to be inadequate.

Figure 14:
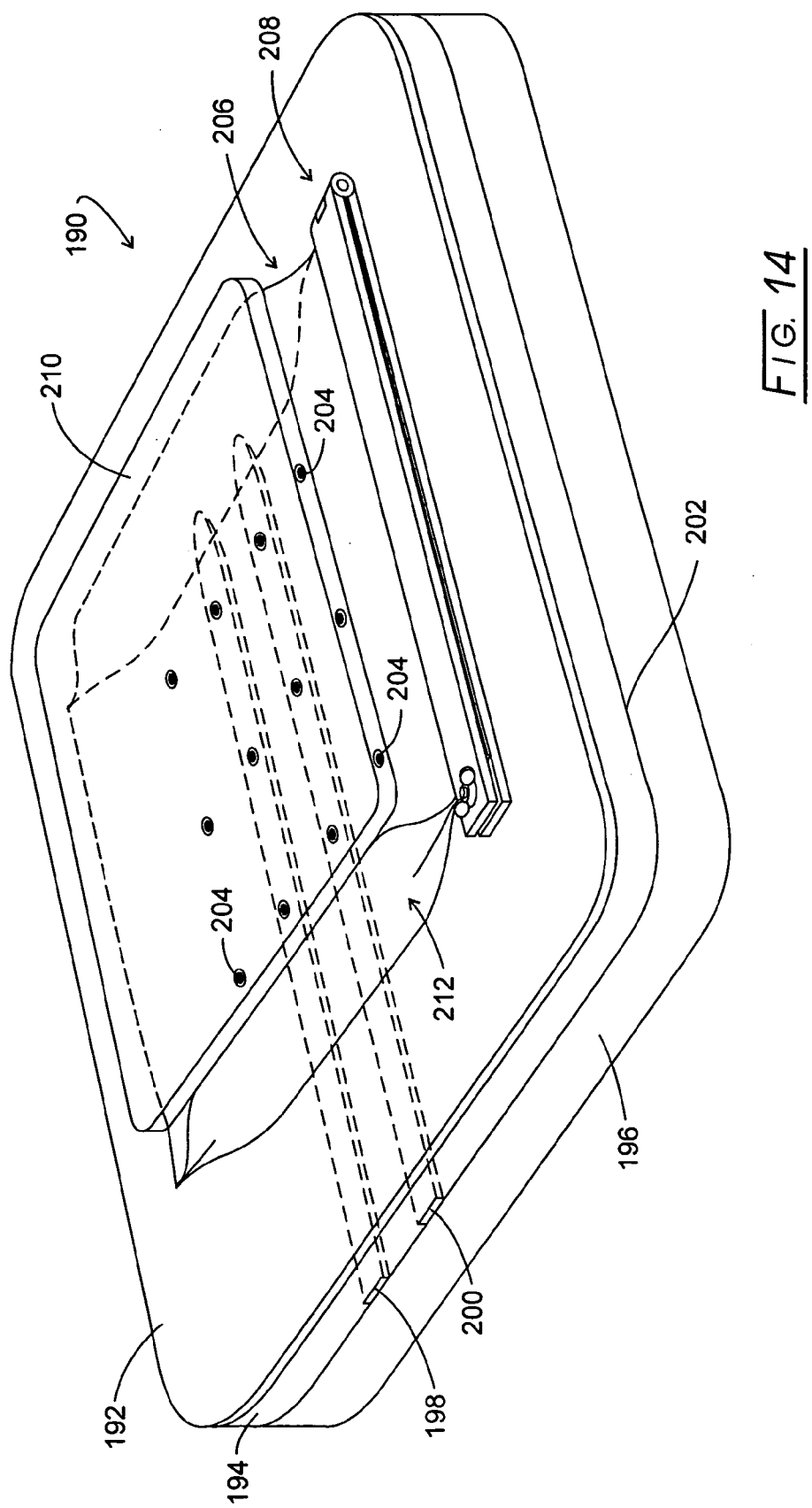
FIG. 14 is a perspective schematic representation of experimentation undertaken utilizing two implants as described in connection with FIGS. 8 and 9 in conjunction with a liquid-filled conformal heat sink and a glass plate for applying pressure.

In experiments, both ex vivo and in vivo (pig) next carried out, a transparent plastic bag was filled with water and used to both cool and apply tamponade or slight pressure against the upper surface of the epidermis during radiofrequency heating of the dermis between parallel implants as described in connection with FIGS. 4 and 5. This heat sink approach also was utilized in conjunction with experiments carried out in the manner of FIGS. 10 and 11. The latter arrangement is generally depicted in FIG. 14 at 190. In the figure, epidermis is schematically represented at 192; dermis at 194 and the next adjacent subcutaneous tissue layer or fat layer at 196. Two parallel implants carrying resistor heaters are represented at 198 and 200 located at the interface 202 between dermis 194 and next adjacent subcutaneous tissue layer 196. Dot indicia, certain of which are represented at 204 were located in a matrix format at the surface of epidermis 192. A water-filled plastic transparent bag or container represented generally at 206 was filled with water and closed using a clamp fixture represented generally at 208. To apply tamponade, a transparent sheet of glass 210 was positioned over the upper surface of bag 206. The inward or contact surface of bag 206 as shown in general at 212 was positioned against the surface of epidermis 192 and functioned to apply a small amount of pressure as well as provide for a thermal transfer from the surface of epidermis 192 to the liquid within container 206. Experiments were run with liquids of different temperature within the container 206. For example, ice water did not work and what was contemplated was a form of heat sinking at temperatures near body temperature which maintained the surface of the skin within the narrow temperature range of from about 37° C. to about 40° C. Implants 198 and 200 were spaced apart 5 mm edge-to-edge or 8 mm center-to-center. It was found that a coating of water or glycerol functioned both as a lubricant permitting the skin surface to shrink during treatment and as a heat transfer medium to the liquid within a container 206. Water and glycerol exhibit a high thermal conductivity to provide for good heat transfer across the interface between the bag 206 and epidermis 192. Thus, the thermal transfer medium preferably will exhibit a high thermal conductivity.

Figure 15:
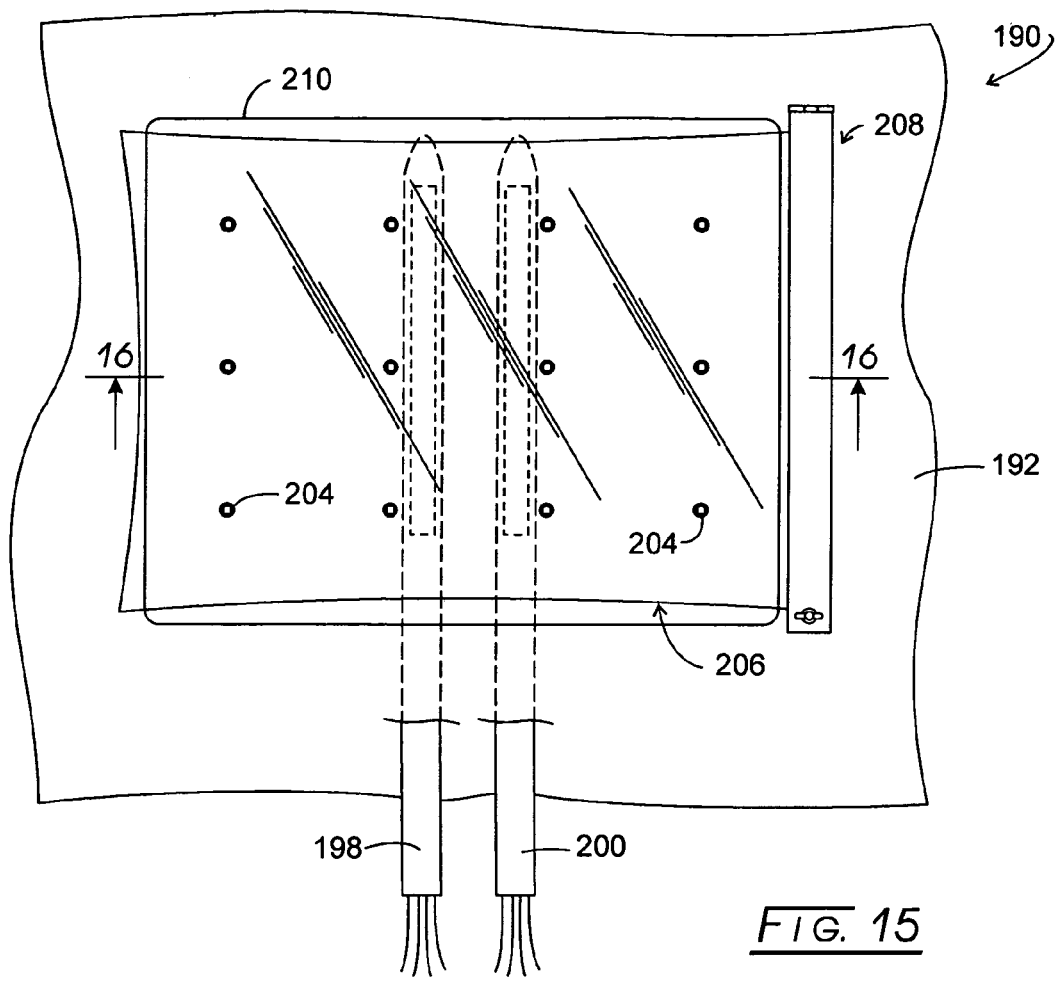
FIG. 15 is a top schematic view of the experiment of FIG. 14.
Figure 16:
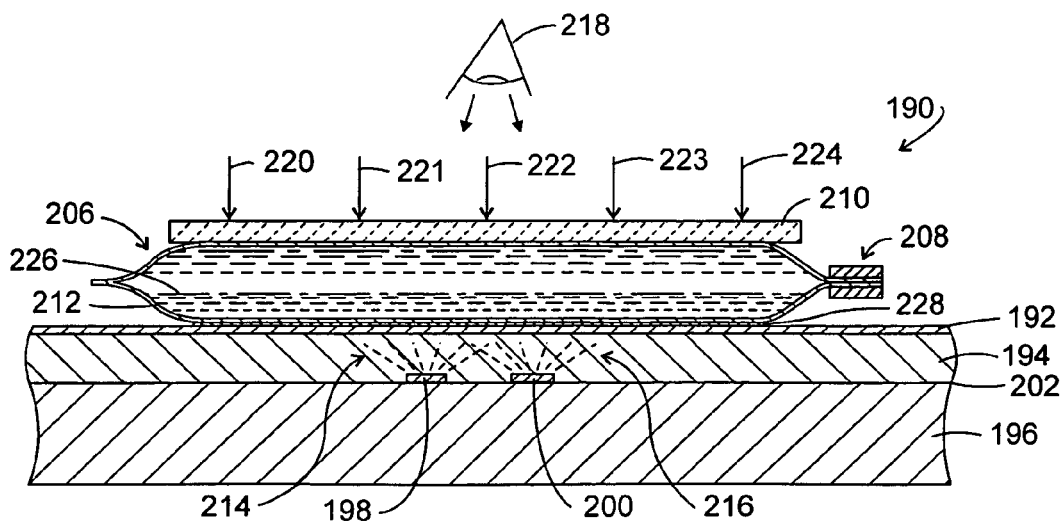
FIG. 16 is a sectional view taken through the plane 16-16 shown in FIG. 15.

Looking additionally to FIGS. 15 and 16, the set-up 190 is reproduced in a top view and a sectional view. In FIG. 16, conduction heat transfer paths are represented as dashed lines and identified in general at 214 and 216 in conjunction with respective implants 198 and 200. During the procedure, the indicia as at 204 (FIG. 15) could be observed as represented at the eye station 218. Slight pressure is applied through the glass plate 210 as represented by force arrows 220-224. Alternatively, the weight of the water filled bag will provide sufficient tamponade if the bag is at least 1.5 inches thick. Water is schematically represented at 226 within container 206. Additionally, a layer of heat transferring and lubricating water is shown at 228, intermediate the contact surface 212 of container 206 and the surface of epidermis 192. With this arrangement, for the water-filled plastic container or bag 206 to perform adequately as a heat sink, it was necessary to agitate the water 226 at least at its adjacency with contact surface 212. With such an arrangement, skin surface temperatures were maintained between about 38° C. and about 40° C., it later being determined that a range of about 37° C. to about 40° C. was preferred.

Figure 17:
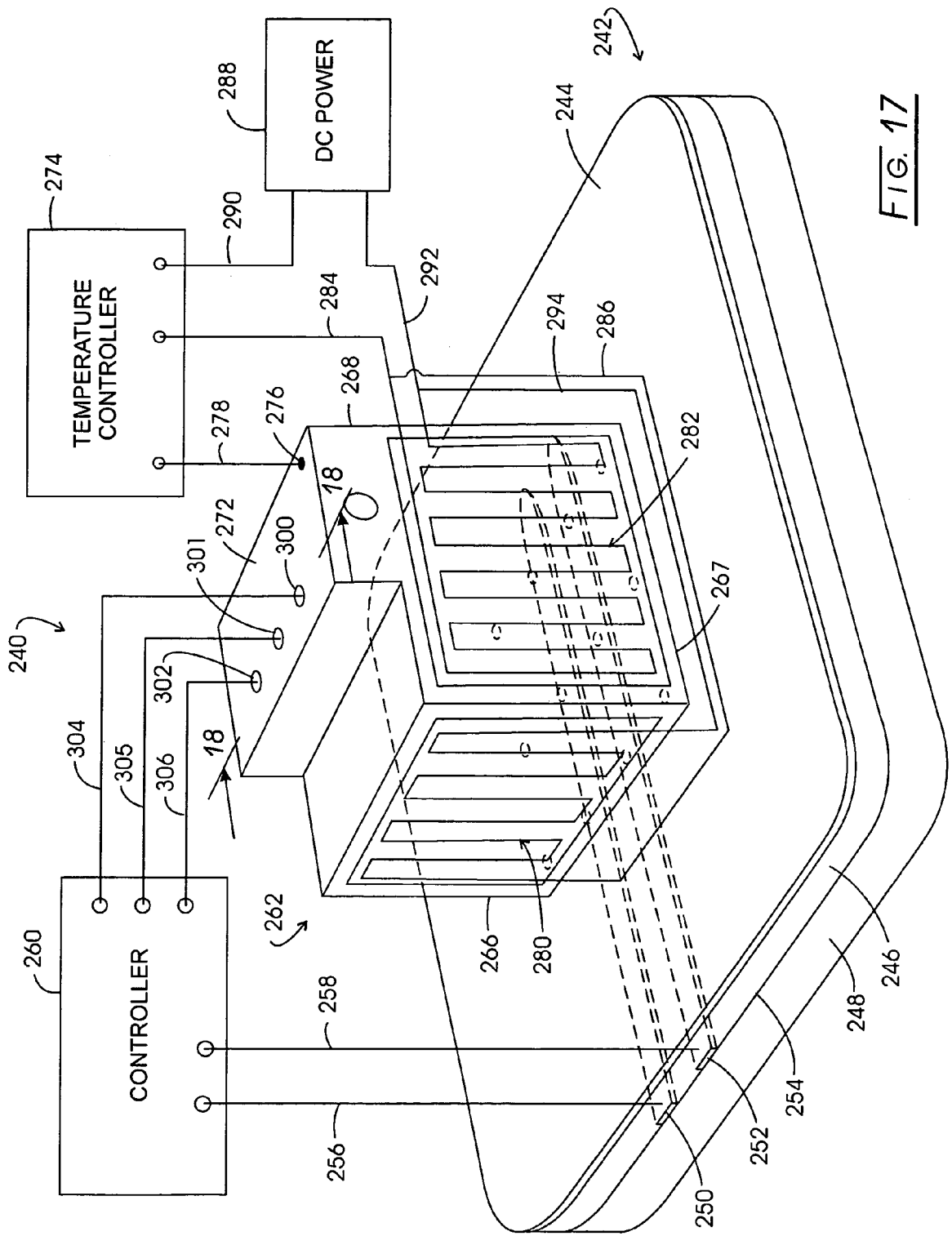
FIG. 17 is a schematic and perspective view of experimentation carried out utilizing an instrumented and heated aluminum heat sink.
Figure 18:
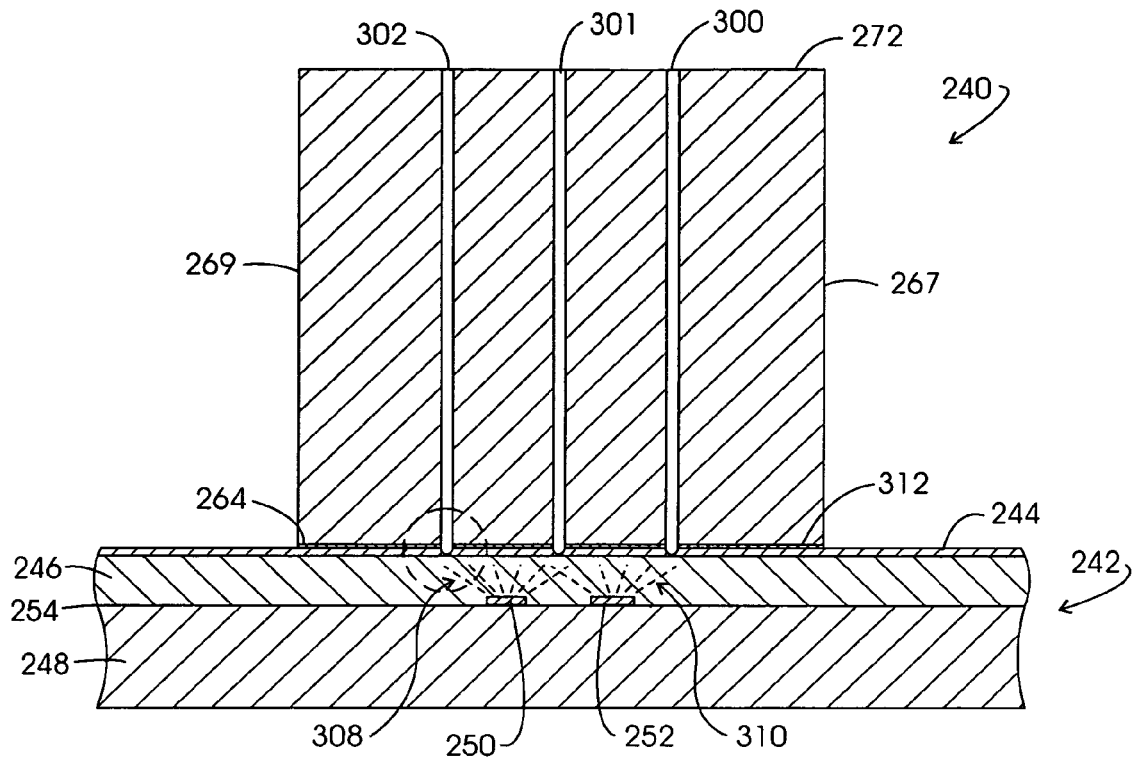
FIG. 18 is a sectional view taken through the plane 18-18 shown in FIG. 17.
Figure 19:
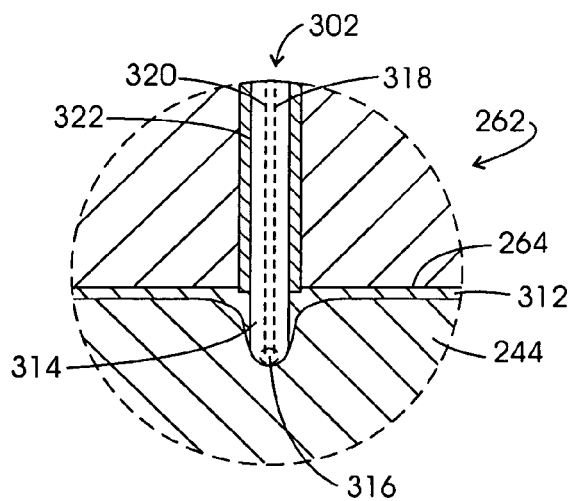
FIG. 19 is an enlarged partial view of an identified portion of the section of FIG. 18.
Figure 25:
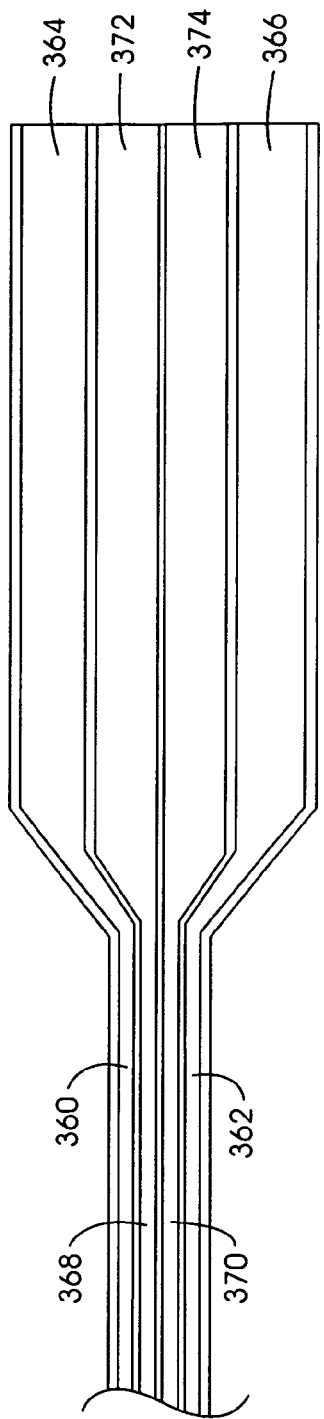
FIG. 25 is a further enlarged view of the lead assemblage configured with the resistor segment of FIG. 24.

Experimentation was also carried out utilizing an instrumented and heated aluminum heat sink. Referring to FIGS. 17-19, such a set-up is represented generally at 240. As before, experiments using set-up 240 were carried out both ex vivo and in vivo in conjunction with skin (pig) as represented in general at 242. In the figures schematically represented are epidermis 244; dermis 246; and next adjacent subcutaneous tissue or fat layer 248. Implants as described in connection with FIGS. 8 and 9 are shown at 250 and 252 located at the interface 254 between dermis 246 and fat layer 248. Implants 250 and 252 were spaced apart 5 mm edge-to-edge or 8 mm center-to-center and arranged in parallel adjacency. Energizing d.c. current to the resistor components of implants 250 and 252 is represented at respective lines 256 and 258 extending from a controller function represented at controller block 260. Resting upon the epidermis layer 244 is a block-shaped aluminum heat sink represented generally at 262. Heat sink 262 was dimensioned with a contact surface seen in FIG. 18 at 264 which was defined by four 2 inch wide sides 266-269 (FIGS. 17, 18) and having a height at top portion 272 of 2½ inches. Sides 266 and 267 were heated by "copper on Kapton" (polyimide) resistance heaters which were controlled from a commercial temperature controller represented at block 274. Controller 274 monitored the temperature of heat sink 262 at a thermocouple 276 (FIG. 17) as represented at line 278. Controlled d.c. power was supplied to the resistance heating functions represented generally at 280 and 282 as represented by circuit lines 284 and 286. Control to the d.c. power function represented at block 288 from controller 274 is at line 290. Power input to the resistive heating functions 280 and 282 is represented extending from power function 288 with lines 292 and 294. Three bores 300-302 are seen extending through the heat sink 262. Each of these bores carried a seed thermocouple, each exhibiting a small outside diameter. The outputs of these thermocouples to the controller function with respect to bores 300-302 are represented respectively at lines 304-306. Aluminum heat sink 202 was electrically insulated by being clear hard anodized. FIG. 18 reveals implants 250 and 252 and interface 254. Emanating from the resistor components of these implants are dashed lines representing conduction heat transfer or migration as shown respectively at 308 and 310 within dermis layer 246. A layer of water represented at 312, as before, provided lubrication and improved thermal transfer between the skin surface and heat sink 262. FIG. 18 further reveals that the spacing between bores 300-302 corresponded with the center-to-center spacing of bipolar radiofrequency performing implants as at 40, i.e., 15 mm. Additionally, bore 301 is spaced evenly between bores 300 and 302. With this spacing, resistor carrying implant 250 is located between bores 301 and 302 and implant 252 is located between bores 300 and 301. Looking additionally to FIG. 19, bore 302 reappears in enlarged form. Within that bore was a 0.020 inch outside diameter (OD) stainless steel sheath 314, the bottom portion of which carries the very small seed thermocouple as revealed at 316. Paired leads 318 and 320 extend from the thermocouple 316 providing the function represented at line 306 in FIG. 17. Stainless steel sheath 314 within the body of heat sink 262 is wrapped with a thermal and electrically insulating shrinkwrap tubing 322 having a thickness of 0.002 inch. It was deemed desirable that the thermocouple as at 316 be supported to measure the temperature at the epidermis surface as opposed to being influenced by the temperature of the heat sink 262. Accordingly, this stainless steel sheath as at 314 extended below contact surface 264 a distance of 0.020 inch such that each thermocouple was located within a slight depression within the epidermis layer 244. The weight of the heat sink 262 itself provided requisite tamponade or pressure. In this regard, the heat sink exhibited a weight of 0.875 pounds to provide a pressure of about 0.219 pounds per square inch. The temperature controller 274 (FIG. 17) was found to maintain the temperature of heat sink 262 at 40° C.+/−0.5° C. Use of this form of heat sink further demonstrated that the layer of water 312 improved the heat sink function. Maximum skin surface temperature for all implant embodiments as measured with these three thermocouples remained between about 42° C. and 43° C. The temperatures never rose above 43° C. for any of the experimental runs and the temperatures as recorded with the thermocouples remain within 1° C. of each other. Using heater implants as at 90 (FIG. 8), the experimental runs demonstrated that the timed element of thermal dosage to the dermis 246 could be importantly reduced depending upon elected setpoint temperature. It was contemplated that pre-cooling of the dermis layer 246 prior to therapy may be beneficial. Additionally, the heat sink function can be continued for an interval following the therapy interval.

The principal structure of the resistor carrying implants configured according to the invention is one wherein a thermally and electrically insulative support is provided which performs as a thermal barrier. Such support is configured, for instance, with the earlier-described polyetherimide, "Ultem". That thermal barrier and support is combined with a thin polymeric electrically insulative circuit support formed of the earlier-described "Kapton". Rectangularly configured serpentine resistor segments are carried by the circuit support with a lead assemblage extending therefrom. The circuit support is adhesively attached to the thermally insulative flat support such that these gold-plated copper resistor segments are located against the flat support surface of the flat support. Accordingly the resisotor segments are protected against otherwise corrosive body fluids and the like. To determine the temperature of the resistor segments, they are intermittently polled with respect to the resistance value they exhibit and that resistance value is compared with a corresponding value representing setpoint temperature. A 4-point circuit lead assemblage is employed to gather resistance and thus temperature data in a manner immune from the impedance characteristics of cables and the like leading from the implant to a controller.

The initial implant embodiment described herein is a single channel or single resistor-type and is illustrated in connection with FIGS. 20-28. Structural configuration in terms of component layers, thicknesses, electrical insulation and cable connector guides will be found to be essentially repeated in the embodiments for multiple channels or multiple resistor segment implants.

Figure 26:
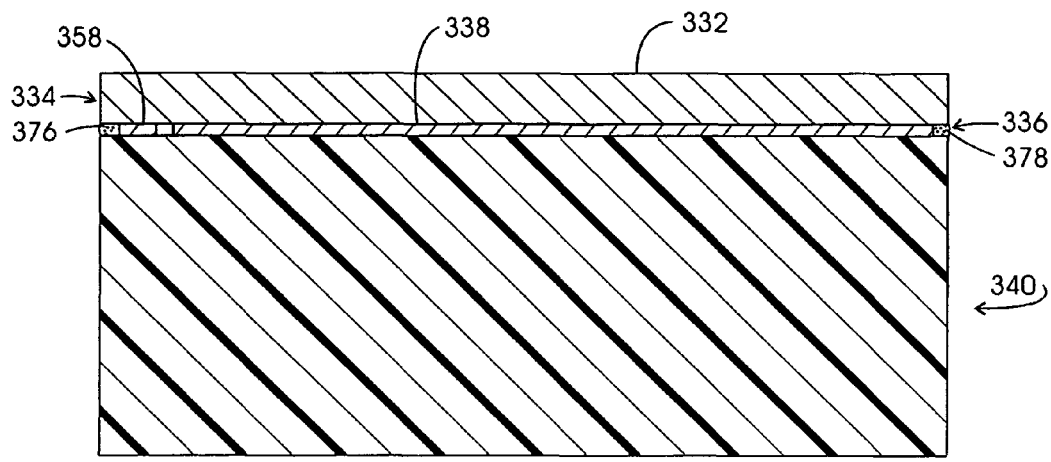
FIG. 26 is a sectional view taken through the plane 26-26 shown in FIG. 22.

Referring to FIG. 20, such a single channel implant is shown in perspective and represented generally at 330. Seen as the forward surface in the figure is the outside surface 332 of a thin polymeric electrically insulative polyimide circuit support identified in general in FIG. 26 at 334. The rectangular periphery of a resistor segment heater represented generally at 336 is located, again as seen in FIG. 26, at the interior or inward surface 398 of circuit support 334. That assemblage, in turn, is supported upon a thermally insulative generally flat polyetherimide support represented generally at 340. Support 340 extends along a lengthwise dimension between a leading end represented generally at 342 to a trailing end represented in general at 344. Toward the trailing end 344, both the flat support 340 and circuit support 334 expand in width to provide more facile engagement with a lead assemblage as represented in phantom at edges 346 and 348. That region is coupled with a polymeric connector guide represented generally at 350. As seen additionally In FIG. 22, the guide 350 at its outward surface is flat with no entrance openings formed within it. However, as seen at the bottom view of FIG. 23, connector guide 350 as well as a portion of the thermally insulative flat support are provided with openings which combine to provide a rectangular access opening represented generally at 352. Opening 352 permits cable connection from resistor connected leads to a controller function. Looking momentarily to FIG. 21, it may be observed that the leading end 342 of the support and thermal barrier 340 is slanted forwardly as seen at 354 to an extent effective to provide a mechanical bias toward dermis when the implant is inserted within a heating channel.

Figure 24:
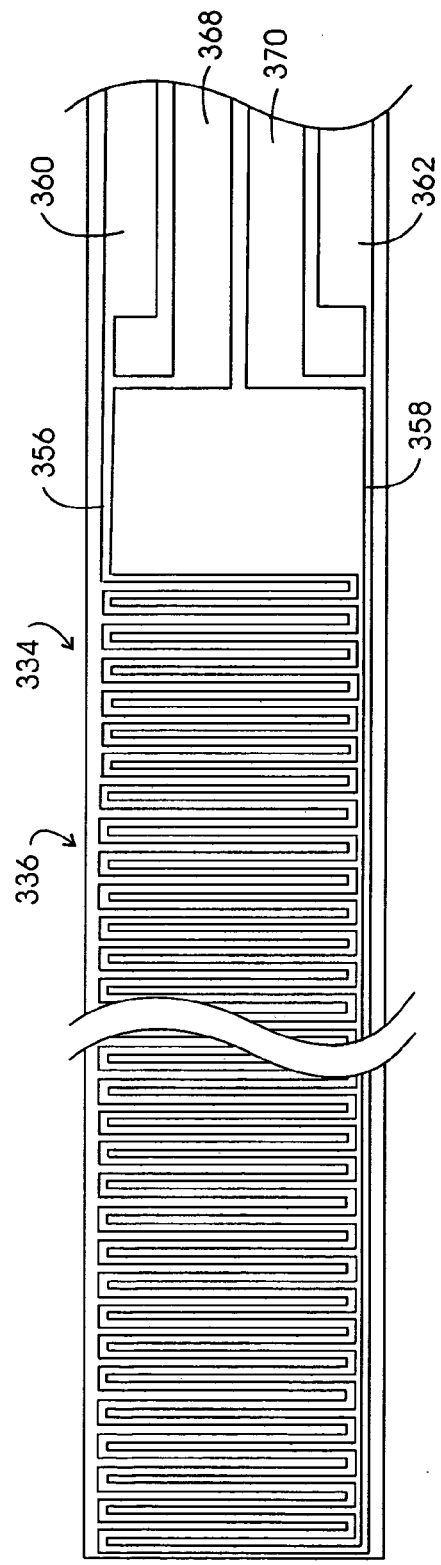
FIG. 24 is an enlarged, broken away view of the resistor segment and associated 4-point lead assemblage of the implant of FIG. 20.

Referring to FIG. 24, the serpentine but rectangular resistor segment 336 reappears in broken away and enlarged fashion. The arbitrarily designated inner surface of "Kapton" substrate or circuit support 334 reappears upon which heater resistor segment 336 has been deposited and is in thermal exchange association therewith. The trace width of segment 336 is 0.003 inch and the spacing between trace lengths also is 0.003 inch. The width of the serpentine segment is 0.086 inch and the resistor segment is offset from the edges of the "Kapton" circuit support 334 by about 0.005 inch. Resistor segments as at 336, in general, are formed of a metal exhibiting a temperature coefficient of resistance greater than about 2000 ppm/° C. Two gold-plated copper leads each having a width of 0.003 inch at 356 and 358 are seen to be extending to and continuous with enlarged gold-plated copper leads shown respectively at 360 and 362. Looking to FIG. 25, leads 360 and 362 are expanded in width still further respectively at 364 and 366. Those leads 364 and 366 function as source current leads for 4-point measurement procedures. Returning to FIG. 24, lead 356 is tapped by lead 368 and lead 362 is tapped by lead 370. Lead 368 continues in expanded width form at 372 and lead 370 continues in expanded width form to provide lead 374. Leads 372 and 374 are sense and power leads to carry out a resistance based temperature measurement, for example, a constant current of 100 milliamps is introduced to source lead 364 to traverse resistor segment 336 and return at lead 358. As that source current is applied, the voltage drop between leads 368 and 370 as represented at leads 372 and 374 is evaluated with respect to resistance and is compared to a resistance value corresponding with setpoint temperature. Following such measurement, power is applied to the sense leads 372 and 374 to excite the heater segment 336 to produce thermal energy. That power interval may, for example, be 100 milliseconds while the sense interval may be, for example, 10 milliseconds.

Returning momentarily to FIG. 26, lead 358 reappears in sectional view in conjunction with resistor segment 336. Note that medical grade adhesive as seen at 376 and 378 completes the encapsulation of resistor segment 336 and its associated lead 376.

Figure 27:
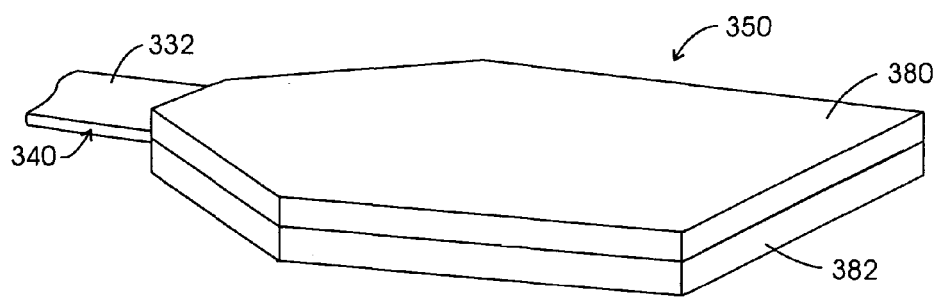
FIG. 27 is a partial perspective view showing the upward side of a cable connector guide employed with the implant of FIG. 20.
Figure 28:
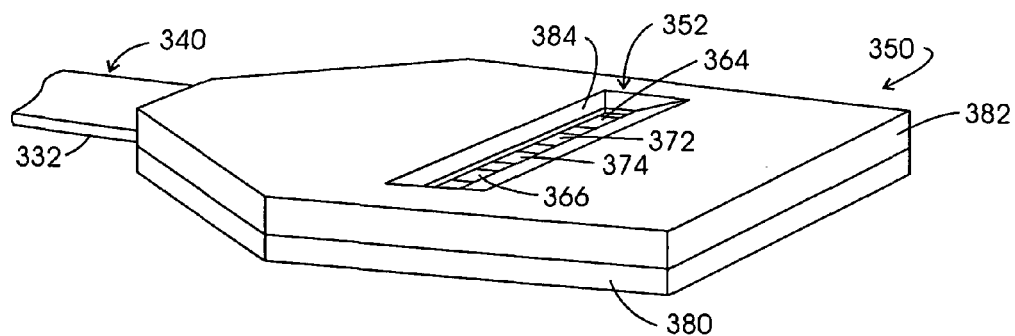
FIG. 28 is a partial perspective view showing the cable connector guide of FIG. 27 but revealing its underside.
Figure 40:
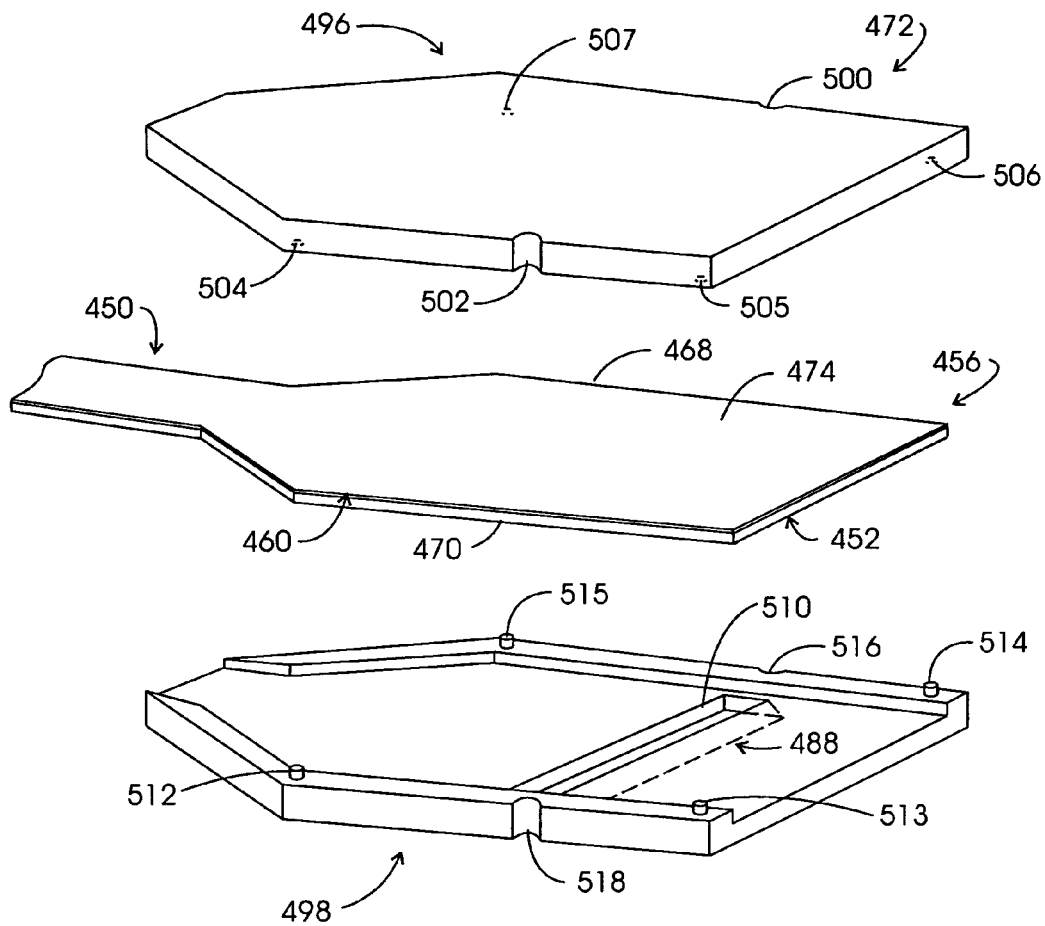
FIG. 40 is an exploded view of the connector guide shown in FIG. 29 and also showing a thermal barrier and lead structure.

Now looking to FIGS. 27 and 28, the connector guide 350 for the single channel implant 330 is revealed at an enhanced level of detail. Such a guide is illustrated later herein in exploded fashion in conjunction with a multi-channel implant (FIG. 40). In FIG. 27, guide 350 is seen to be fashioned of two interlocking components, an upper one being shown at 380 and a lower one being shown at 382. In general, components 380 and 382 are formed of white medical-grade polycarbonate material. Looking to FIG. 28, component 382 is seen to be molded with a lead accessing notch 384 forming part of access opening 352, it being recalled that an access also is made through flat support 340. These 4-point leads 364, 366, 372 and 374 are revealed within access opening 352.

FIGS. 29-33 illustrate an implant structured in similar fashion as that at 350 but incorporating more than one heating and sensing resistor segment. In particular, the embodiment illustrated contains four resistor segments or channels. With the exception of greater length, the implant dimensions heretofore discussed remain the same for these multiple channel embodiments. Referring to FIG. 29, a four heater resistor segment implant is represented generally at 390 in perspective fashion. Looking additionally to FIGS. 30 and 33, the outer surface 392 of a thin polyimide circuit support 394 is revealed. As seen in FIG. 33, the inward surface 396 of circuit support 394 supports four heater and temperature sensing resistor segments shown in phantom in FIGS. 29 and 30 at 400-403. As represented in FIGS. 29 and 33, circuit support 394 is, in turn, positioned upon generally flat thermally insulative polyetherimide support represented generally at 406 and as seen in FIG. 33 is configured with an insulative surface 410. Circuit support 394 and its associated resistor segments, for example, at 400 is adhesively attached to the support surface 408 of flat support 406. In this regard, encapsulation is complete with outboard adhesive components 412 and 414. Flat support 406 is seen having a lengthwise dimension extending between a leading end represented generally at 416 and a trailing end represented generally at 418. A polymeric connector guide is shown in general at 420 which is positioned about trailing end 418 of the implant 390, a location wherein the widthwise extent of the implant is expanded to provide for resistor leads of increased width. The resultant expanded widthwise boundary is represented in phantom at 422 and 424 in FIG. 29. Looking momentarily to FIG. 32, it may be observed that leading end 416 of the thermal barrier and support 406 is slanted forwardly to an extent effective to provide a mechanical bias toward dermis when the implant is inserted within a heating channel. That slanted region is shown at 426.

As in the case of implant 330, the upward surface of the connector guide 420 is uninterrupted as seen in FIGS. 29 and 30. However, looking to FIG. 31, the bottom surface of the guide 420, as before, is configured with a rectangular access opening represented generally at 428. Opening 428 extends not only through the lower component of the connector guide 420 but also through flat support 410 to derive access to the leads extending to the resistor segments 400-403.

Referring to FIG. 34, resistor segments 400-403 are represented in enlarged and broken away fashion as they are supported from the inward surface 396 of circuit support 394. The segments 400-403 are addressed by four lead traces identified respectively at 430-433. A common or return lead is shown at 434. Leads 430-434 are continuous with and extend to leads of enlarged widthwise dimension shown respectively at 436-440. Having a 4-point topography, the lead assemblage additionally provides that lead 430 extends to a source current lead 441 and that a sense current lead 435, provided in common with lead 434, extends to a sense current lead 442 of increased widthwise dimension. Expanded widthwise dimension leads 436-442 reappear in FIG. 35 extending in continuous fashion to respective leads 444-450 which are of further expanded widthwise extent. With this 4-point arrangement, as before, leads 449 and 450 are source current leads, while leads 444-448 are voltage drop sensing leads and powering leads for the resistor segments. Lead 430 reappears in the sectional view of FIG. 33.

Figure 38A:
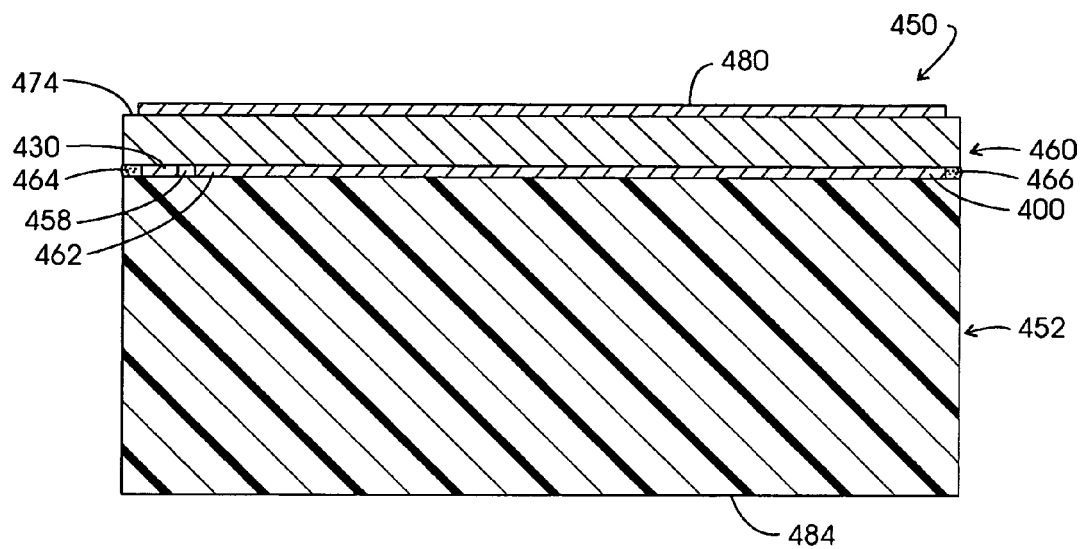
FIG. 38A is a sectional view taken through the plane 38A-38A shown in FIG. 37.
Figure 38B:
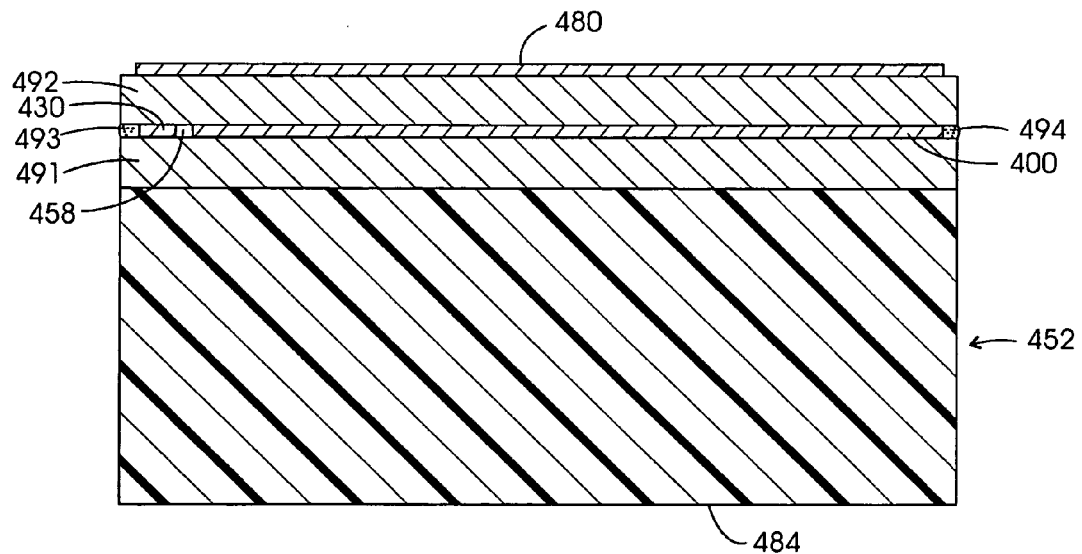
FIG. 38B is a sectional view similar to FIG. 38A but showing a configuration with a circuit support and a separate thermal spreader support.

The performance of resistor segments 400-403 as described in connection with implants as at 390, may be enhanced in terms of thermal performance through the utilization of thermal spreaders. FIGS. 36, 37, 38A, 38B and 39 reveal such an adaptation. In these figures, resistor segments 400-403 as well as their associated lead topography retain the same identifying numeration as provided in conjunction with FIGS. 33-35. Referring to FIG. 36, such an implant is represented generally at 450. Implant 450 is configured with a thermally insulative generally flat polyetherimide support provided, for example, at the earlier described "Ultem". The thermal barrier and flat support as represented generally at 452 exhibits a lengthwise dimension extending between a leading end identified generally at 454 and a trailing end identified generally at 456. As seen in FIG. 38A, the support surface 458 of support 452 adhesively supports and secures the resistor segments and forward portions of the lead assembly, segment 400 and lead 430 being shown in the figure. These resistor segments 400-403, in turn, are carried by a thin (0.001 inch) polyimide electrically insulative circuit support (Kapton) represented generally at 460. In particular, the resistor segments 400-403 and associated lead assemblage are carried at the inward surface 462 of circuit support 460 thus their representation is in phantom in connection with FIG. 36. Such an arrangement protects the gold-plated copper electrical components from contamination due to body fluids or the like. In this regard, FIG. 38A additionally reveals medical-grade adhesive as at 464 and 466 at the outboard sides of the resistor segments functioning to complete their encapsulation. In order to accommodate lead components of expanded widthwise dimension, both the flat support 452 and circuit support 460 expand width at the trailing end 456 as represented by boundaries 468 and 470 which are shown in phantom as they are retained within a polymeric connector guide represented generally at 472.

FIGS. 36 and 37 reveal that outward surface 474 of circuit support 460 carries four generally rectangularly-shaped thermal spreaders 480-483. Formed, for example, of a thermally conductive material such as gold-plated copper, these spreaders 480-483 promote to promulgation of thermal energy into dermis in somewhat uniform fashion. Note that the thermal spreaders are configured with edge boundaries corresponding in alignment with the edge boundaries of a thermally associated resistor heater segment. The spreaders 480-483 may, for example, when formed of a copper material exhibit a thickness of between about 0.005 inch and about 0.020 inch. A thickness of 0.0056 inch has been found to be convenient inasmuch as it corresponds with conventional "4-ounce" copper.

FIGS. 38A and 39 reveal the lower or insulative surface 484 of flat support 452. Additionally, as seen in FIG. 39, the tip at the leading end 454 of flat support 452 is forwardly slanted as represented at surface 486. This slant is the same as described in connection with FIG. 32. The figure also reveals a rectangular access opening shown generally at 488 extending both through the lower surface 490 of connector guide 472 as well as the flat support 452 itself to access the leads at the inward surface 462 of circuit support 460.

An adaptation may be made with respect to the mounting and resultant encapsulation of the resistor segment-lead assemblage circuit over the polyetherimide flat support. By utilizing two layers of the 0.001 inch thick polyimide circuit support material (Kapton) access to the lead assemblage may be provided through the upward component of connector guides as at 472. Such an alternative access is represented in dashed line fashion at 488' in FIG. 37. As is apparent, providing an access opening through the trailing end 456 of flat support 452 is not required for such an arrangement. The pertinent alteration to the implant structure is illustrated schematically in FIG. 38B. Looking to that figure polyetherimide flat support 452 remains with lower (insulative) surface 484 not being disturbed. It's oppositely disposed support surface 458 now is adhered to the underside of 0.001 inch thick polyimide (Kapton) circuit support 491, the outward surface of which carries the resistor segments 400-403 and associated lead assemblage, resistor segment 400 and its lead 430 again being illustrated. Adhesively mounted over such circuitry except at trailing end 456 is an encapsulation polyimide (Kapton) layer 492, again of 0.001 inch thickness. Encapsulation is secured with medical-grade adhesive as indicated at 493 and 494. Without more the structure and represents an alternative embodiment to implant 390 described in connection with FIGS. 29-32. Where polyimide layer 492 supports thermal spreaders such as that at 480, an alternative architecture to implant 450 is realized. The central theme to all embodiments resides in a thin layer polyimide encapsulation of appropriate circuit components.

Referring to FIG. 40, an exploded view of the medical-grade polycarbonate connector guide 472 is provided. Guide 472 is configured in somewhat clam shell fashion being formed of two connector guide components represented generally at 496 and 498. Components 496 and 498 are shown positioned above and below the trailing end of region 456 of implant 453. In this regard, flat support and thermal barrier 452 is observable in combination with the circuit support 460. The outward surface 474 of circuit support 460 is seen to carry no resistor segment leads, those leads being disposed at its inward surface 462 as seen in FIG. 38A. Component 496 is seen to incorporate oppositely disposed detents 500 and 502 which are provided to assure a secure connection with a cable connector. Note additionally that component 496 is formed with upwardly depending cylindrical pin-receiver holes represented in phantom at 504-507.

Component 498 incorporates a rectangular, inwardly tapered window 510 which serves as the outer component of rectangular opening 488 (FIG. 39) and four upstanding cylindrical alignment pins 512-515 which are configured to engage respective pin receiver holes 504-507 in a snap-together arrangement. Finally, component 498 is formed with oppositely disposed detents 516 and 518 which correspond for alignment with respective detents 500 and 502.

Figure 41:
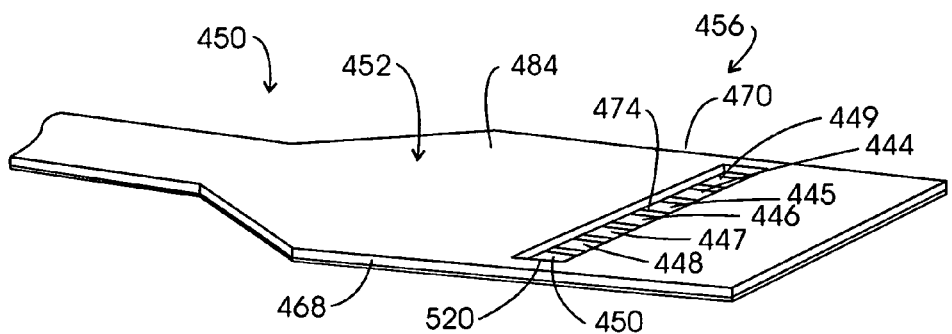
FIG. 41 is a partial perspective view of the bottom of the trailing end region of the thermal barrier and associated circuit of the implant of FIG. 29.

Referring to FIG. 41, implant 450 is shown overturned in the sense of its rendition in FIG. 40. Accordingly, the insulative surface 484 of flat support and thermal barrier 452 is shown to be upwardly disposed. Note that the flat support and thermal barrier 452 is configured with a rectangular opening 520 forming the inner component of opening 488 (FIG. 39) and revealing access to resistor segment leads 444-450.

Referring to FIG. 42, connector guide 472 reappears with its assembled components 496 and 498 in conjunction with a cable connector represented generally at 526. Connector 526 is formed of two polymeric components 528 and 530 which are seen to engage a ribbon-type multi-lead electrical connector 532. Looking additionally to FIG. 43, connector guide 472 and cable connector 526 reappear. It may be observed that components 528 and 530 define a cavity 534. Within cavity 534 there are located seven gold-plated, beryllium-copper cantilever beam contacts one of which is represented at 536. These seven contacts engage the seven 4-point connection resistor segment lead traces 444-450 (FIG. 35). Note that the forward contacting portion of contacts as at 536 engage the bottom of circuit support 460 through a window or opening 488 incorporating openings 510 and 520.

The positioning of implants as at 390 and 450 at the interface of dermis and the next subcutaneous tissue layer may involve the preliminary formation of a heating channel utilizing a flat needle introducer or blunt dissector. Looking to FIG. 44, such an introducer is represented generally at 540. Device 540 is, for instance, 4 mm wide and is formed of a stainless steel, for example, type 304 having a thickness of about 0.015 inch to about 0.020 inch. Its tip, represented generally at 542 is not "surgically sharp" in consequence of the nature of the noted interface between dermis and fat layer. However, looking to FIG. 45, it may be observed that the tip 542 slants upwardly from bottom surface 544 to evoke a slight mechanical bias toward dermis when the instrument is utilized for the formation of a heating channel. In general, the procedure involves forming the channel with the instrument 540, whereupon it is left in place and an implant then is inserted through the entrance incision along the top of it. Following appropriate insertion of the heater implant, the introducer instrument 540 is removed from the heating channel.

As discussed in connection with FIGS. 14-19, experimentation determined that where, for example, water-filled conformal containers were utilized as a heat sink for the instant procedure, agitation of such liquid or water near at least the contact surface is desirable. In this regard, it was found that the utilization of a conventional laboratory magnetic stirring assembly was quite effective. Measurement of the effectiveness can be carried out by immersing tea leaves or some similar flocculent material within the container to observe the extent of liquid agitation.

Figure 46:
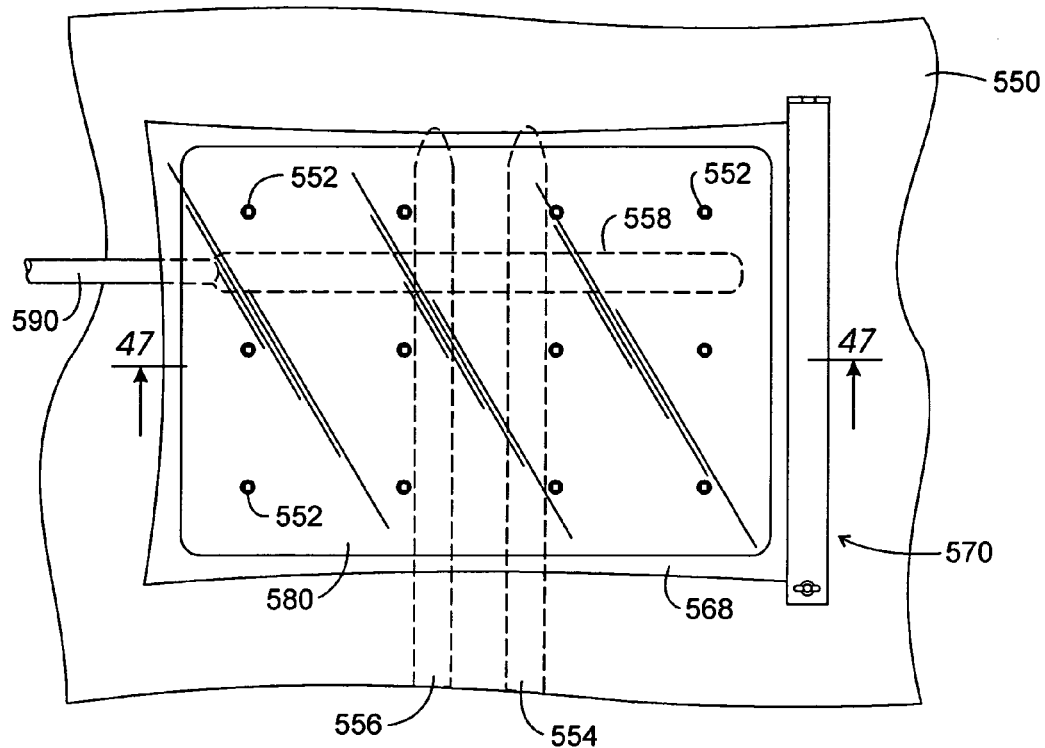
FIG. 46 is a top schematic view of a conformal transparent heat sink showing a water agitating pneumatic bladder.
Figure 47:
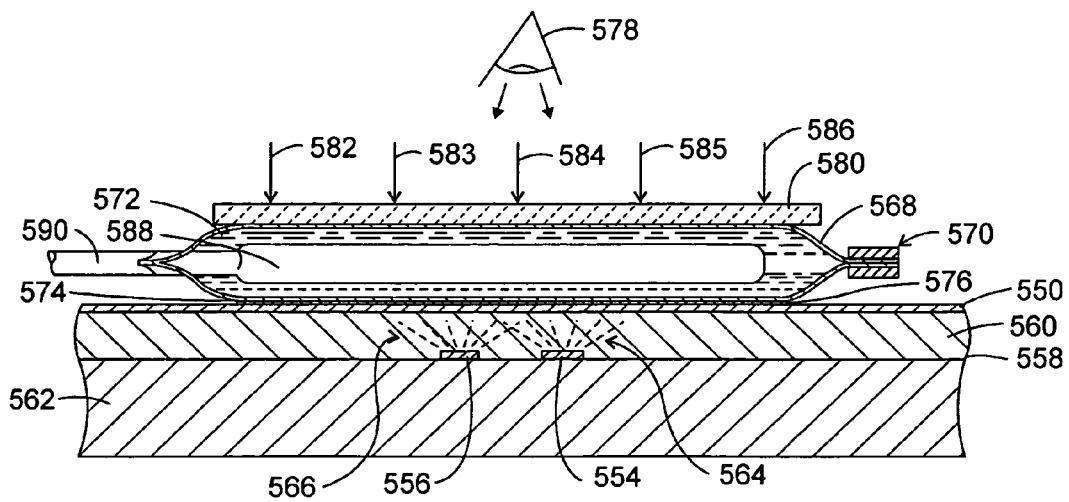
FIG. 47 is a sectional view taken through the plane 47-47 shown in FIG. 46.

Another liquid agitation approach is represented in FIGS. 46 and 47. In FIG. 46, epidermis is represented at 550 having a matrix of indicia located on the surface thereof, certain of which are represented at 552 showing digitally recorded additional positions as white centers and dark circles as skin carried indicia. Looking additionally to FIG. 47, two single resistor segment implants 554 and 556 have been located in heater channels positioned at the interface 558 between dermis 560 and the next adjacent subcutaneous tissue or fat layer 562. Conduction heat transfer from the resistor segments of implants 554 and 556 is depicted as a thermal migration pattern shown respectively in general at 564 and 566. In general, the implants 554 and 556 will be mutually spaced about 5 mm edge-to-edge. A bag-like transparent conformal polymeric container 568 is positioned above the implants 554 and 556 and is seen to be closed or secured by a clamping assembly represented generally at 570. FIG. 47 reveals that the container 568 is filled with a suitable liquid such as water as at 572 and its contact surface as at 574 is slightly pressed against a water heat transfer and lubricant layer 576. Other heat transfer layers such as glycerol may be employed, however, water exhibits an excellent heat transfer characteristic. Contact surface 574 is slightly pressed against layer 574 to assure uniform and continuous contact of the resistor segment region of the implants with dermis. Dermis shrinkage is visualized, for example, from eye station 578 looking through transparent glass plate 580. Pressure applied to the plate 580 is symbolized by force arrows 582-586. For the instant embodiment, water 572 is agitated by the reciprocative inflation and deflation of an elongate bladder having a pneumatic input/output pipe, a portion of which is shown at 590.

Figure 48:
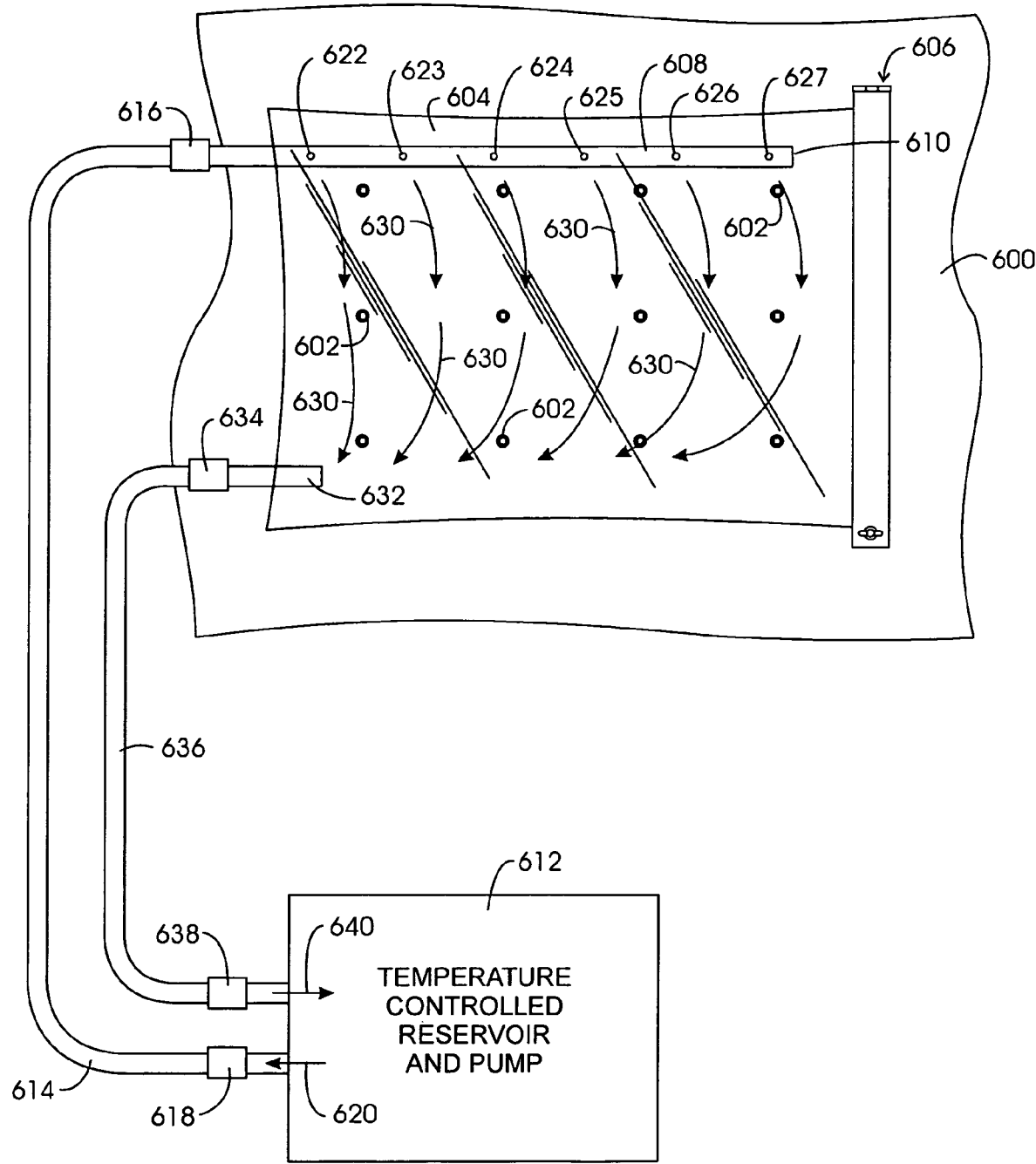
FIG. 48 is a top schematic view of a transparent conformal heat sink utilizing temperature controlled water recirculation.

Referring to FIG. 48, a conformal heat sink arrangement is depicted wherein temperature controlled water or suitable liquid is circulated within a polymeric container. In the interest of clarity, implants, a glass plate and the like are not shown. However, the surface of epidermis is shown at 600 over which a matrix of visible indicia have been located and the initial positions thereof digitally recorded. Certain of these indicia are represented at 602. As before, the central white square portions of these indicia are the originally memorized components and the circular indicia are those placed upon surface 600. The polymeric bag or conformal container of the heat sink function is represented at 604 which will have a conformal contact surface pressing against epidermis surface 600 with an intermediate thermal transfer and lubricating layer of water or the like therebetween. The bag-like container 604 is closed by a clamping assembly represented generally at 606. Shown extending within and across the length of container 604 is a multi-orifice water distribution pipe or conduit 608 which may be both transparent and flexible. The conduit 608 is plugged at its distal end 610 and is supplied a flow of temperature controlled water from a reservoir and pump 612 via a flexible polymeric conduit 614. In this regard, conduit 614 is coupled to conduit 608 at a connector 616 and to the reservoir and pump at a connector 618. The outflow of water is represented at arrow 620. Depending upon the apparatus and conduit lengths involved, conduit 614 may be provided with a thermally insulative covering. The setpoint heat sinking temperature for the fluid involved is controlled at reservoir and pump 612 and the setpoint temperature for such devices will be in the range of about 20° C. to about 26° C. Fluid is circulated from orifices 622-627 of conduit 608 as represented by flow arrows certain of which are identified at 630, to return to reservoir and pump 612 through a relatively shorter outlet conduit 632. Conduit 632 is coupled by a connector 634 to a flexible turn conduit 636 which, in turn, communicates with the pump and reservoir 612 from connector 638. Fluid return to the pump and reservoir 612 is represented at arrow 640.

Figure 49:
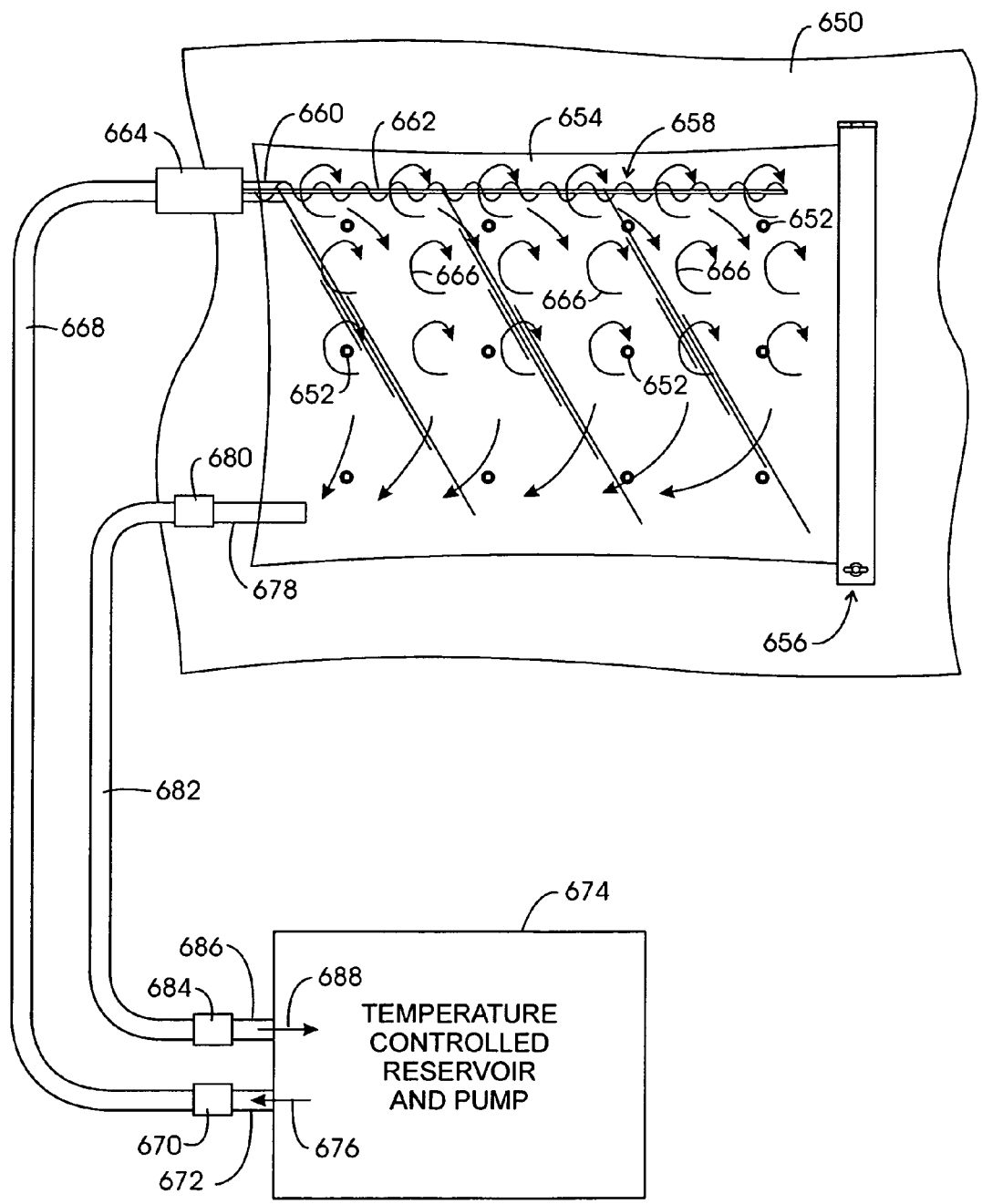
FIG. 49 is a top schematic view of a conformal transparent heat sink showing temperature controlled water recirculation in conjunction with a water-driven agitator.

Recirculating heat sink assemblies as described in FIG. 48 also can be implemented with a mechanical form of water agitation and circulation. Looking to FIG. 49, a mechanically implemented water circulating approach is illustrated. In the figure, a surface of epidermis is shown at 650 upon which a matrix of dot indicia is positioned. Certain of those dot indicia are represented by the common numeration 652. As before, the dot indicia are shown surmounting a white square representing the initial dot position before the procedure occurs which is recorded in digital memory. A transparent conformal container or bag is represented at 654 positioned over the epidermis surface 650. Container 654 is closed with a clamping assembly represented generally at 656. Within container 654 there is located a rotatably mounted polymeric screw mechanism represented generally at 658. Screw mechanism 658 is supported for rotation at a water input tube 660 and is seen to have a centrally disposed shaft 662 rotatably extending from a fluid drive component 664 which delivers water under pressure into the tube 660 to effect rotation along with rotational agitation of water within container 650. That agitation is represented by the generally "C-shaped" arrows, certain of which are identified at 666 representing the generation of water eddy currents. Temperature controlled water input to drive 664 is from flexible conduit 668 which extends to fluid coupling 670 connected, in turn, to the outlet conduit 672 of a temperature controlled reservoir and pump 674. The controlled temperature water output is represented at arrow 676. Water within the container 654 is returned to the reservoir and pump 674 through an output conduit or pipe 678 extending to a fluid connector 680. Flexible fluid return conduit 682 extends from connector 680 to fluid connector 684. Connector 684, in turn, is coupled with an input pipe or conduit 686 communicating with the temperature controlled reservoir and pump 674 as represented by arrow 688.

Figure 50:
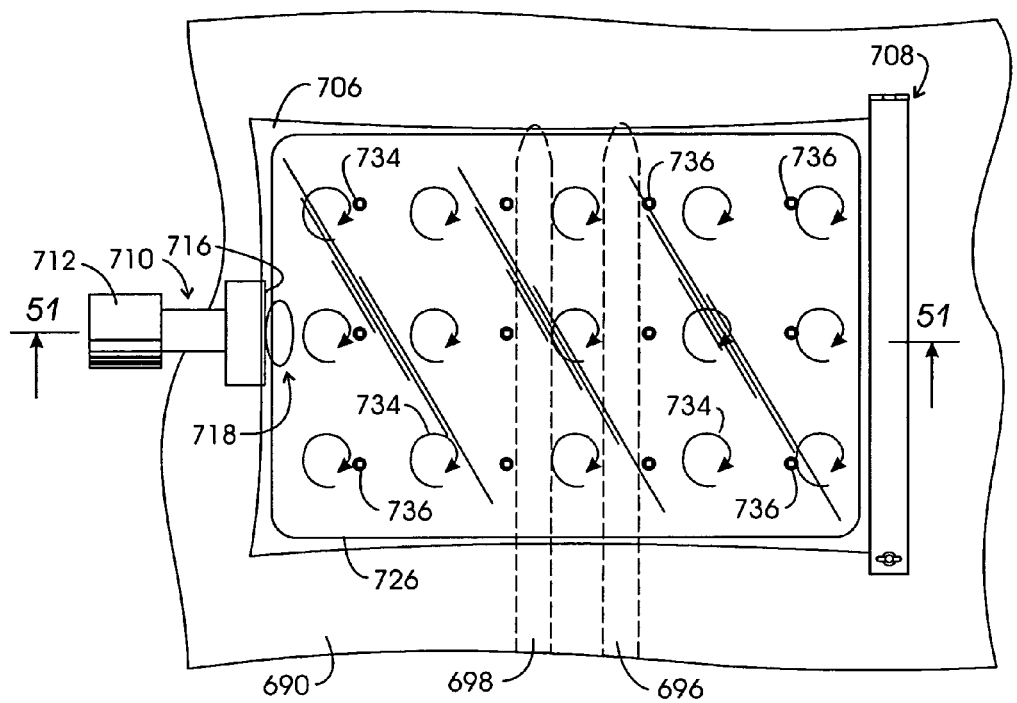
FIG. 50 is a top schematic view of a transparent conformal heat sink retaining water agitated with a motor-driven magnetic stirring assembly.
Figure 51:
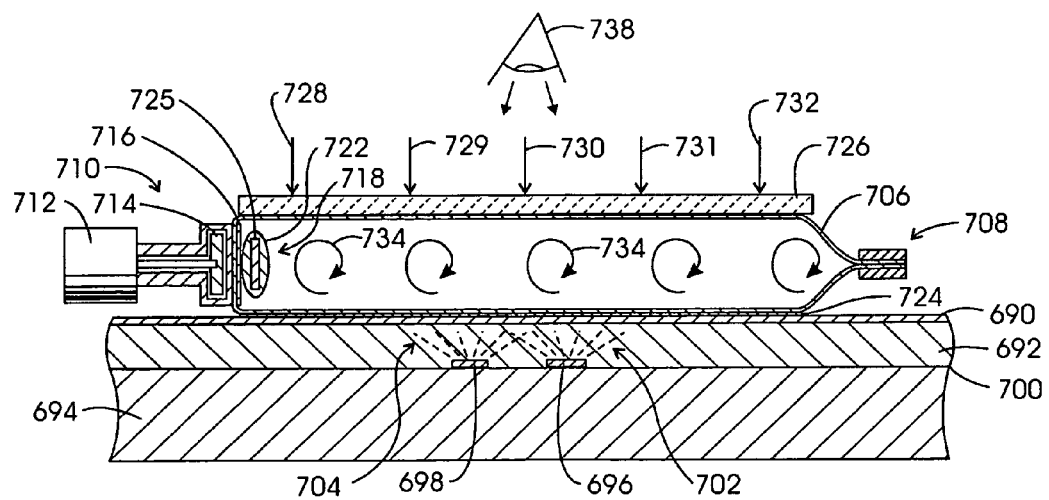
FIG. 51 is a sectional view taken through the plane 51-51 shown in FIG. 50.

As described earlier herein, certain experimentation was carried out utilizing a conventional laboratory stirrer as a heat sink water agitator. Looking to FIGS. 50 and 51, such an arrangement is depicted. In the figures, epidermis is represented schematically at 690; dermis at 692; and next adjacent subcutaneous tissue or fat layer at 694. Two resistor segment-based implants 696 and 698 are located at the interface 700 between dermis 692 and next adjacent subcutaneous tissue or fat layer 694. Thermal migration due to conduction heat transfer is represented generally by dashed line collections shown in general at 702 and 704 with respect to implants 696 and 698. Positioned over the outer surface of epidermis 690 is a transparent conformal container or bag 706 which encloses a liquid such as water and is secured by a clamp assembly represented generally at 708. At the opposite side of the container 706 there is located a magnetic stirring assembly represented generally at 710. Assembly 710 includes an electric motor 712, the output shaft of which drives a magnet 714 (FIG. 51). Opposite magnet 714 and within the container 706 is a polymeric flat plate 716 and freely immersed within the container 706 adjacent plate 716 is an ellipsoidal magnet stirring rod represented generally at 718 and seen in FIG. 51 as being comprised of a rod magnet 720 embedded within a polymeric capsule 722. That figure also reveals a layer of water 724 functioning as a thermal transfer and lubricating medium between the surface of epidermis 690 and the contact surface of container 706. Slight pressure is asserted through the container 706 from a transparent glass plate 726 as represented by force arrows 728-732. Water agitation is represented by curled arrows, certain of which are identified in the figures at 734. FIG. 50 reveals a matrix of visible indicia or dots representing an initial skin condition, certain of these indicia are identified at 736 as black dots, the centers of which are represented as a small white square corresponding with an initial digital recordation of the indicia prior to commencement of therapy. These dots may be viewed by the clinician as represented in FIG. 51 at eye station 738.

Figure 52:
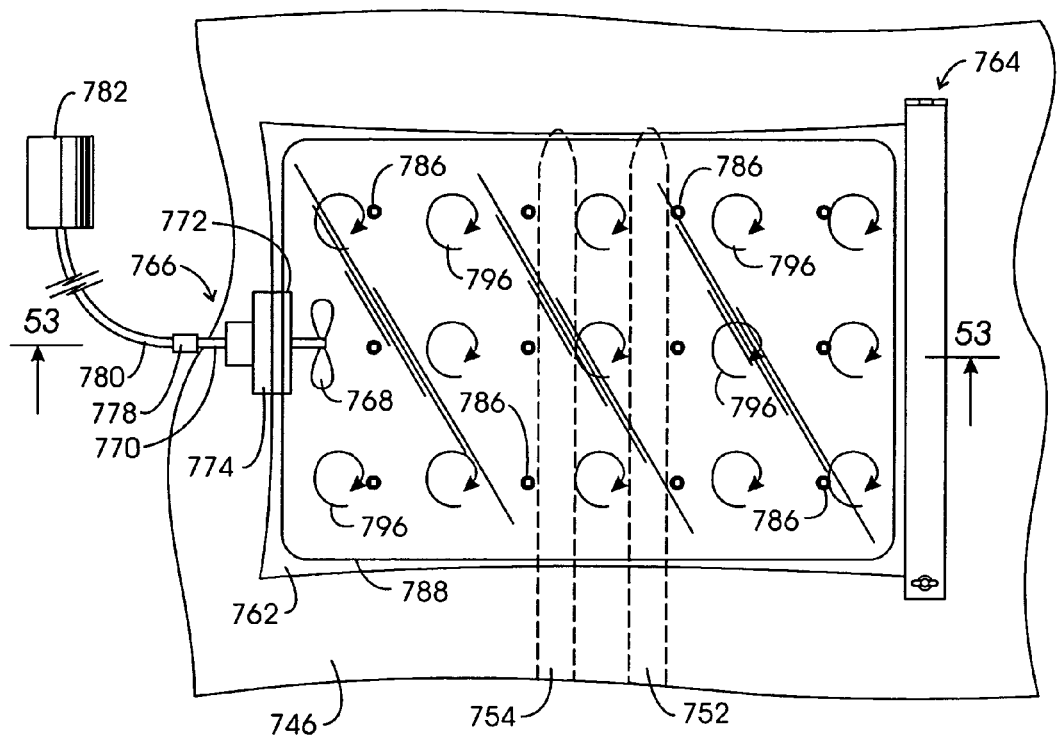
FIG. 52 is a top schematic view of a conformal transparent heat sink retaining water agitated with a motor-driven impeller.
Figure 53:
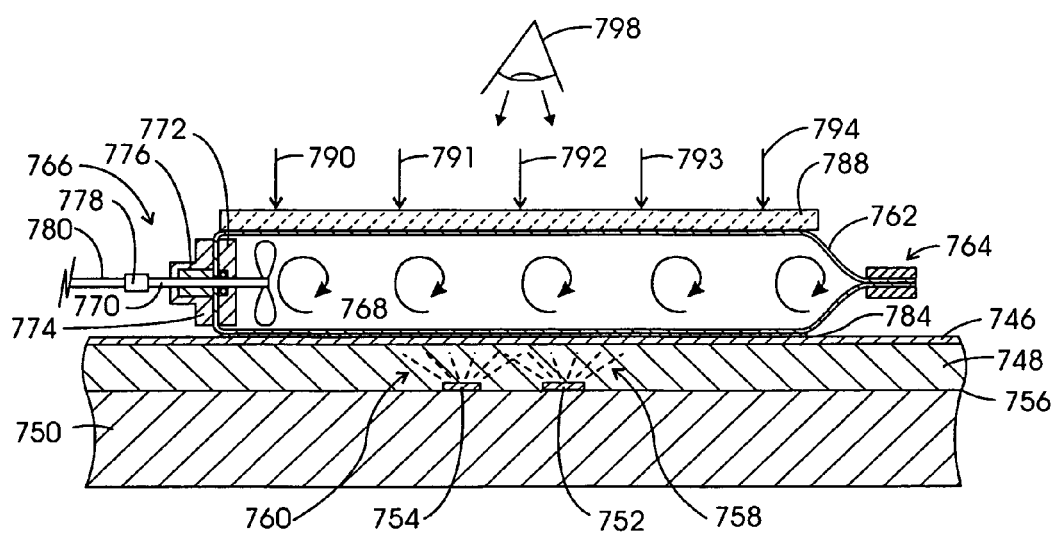
FIG. 53 is a sectional view taken through the plane 53-53 in FIG. 52.

Direct agitation of the water within the conformal container heat sinks also can be developed utilizing a conventional impeller. Looking to FIGS. 52 and 53, such an arrangement is schematically depicted. In FIG. 53 epidermis is shown at 746; dermis at 748; and next adjacent subcutaneous tissue or fat layer at 750. Adjacently disposed generally parallel resistor segment carrying implants 752 and 754 are located in heating channels at the interface 756 between dermis 748 and next adjacent subcutaneous tissue 750. The thermal migration accompanying conduction heat transfer from the implants 752 and 754 is represented respectively at dashed line groupings 758 and 760. Such migration, for example, occurs with an edge-to-edge spacing between implants 752 and 754 of 5 mm or a center-to-center spacing of 8 mm. Positioned over the epidermis 746 is a transparent conformal container or bag 762 which retains water and is closed at a clamping assembly represented generally at 764. Immersed in the water within container 762 is a driven propeller assembly represented generally at 766. Assembly 766 includes a propeller blade 768 mounted for driven rotation on a shaft 770 extending through polymeric seal plates 772 and 774. Plates 772 and 774 are retained against each other at opposite faces of container 762 material by machine screws (not shown) and the shaft 770 is seen in FIG. 53 to extend through a water seal bushing 776. The shaft also is connected at a connector 778 with a flexible driveshaft 780 extending in driven relationship to an electric motor seen in FIG. 52 at 782. FIG. 53 further reveals a layer of water 784 which functions to provide enhanced thermal exchange and lubrication between the heat sink contact surface and the surface of epidermis 746. FIG. 52 illustrates schematically a matrix of visible indicia certain of which are identified at 786. Indicia 786 comprise black dots located at the surface of epidermis 746 and interiorly disposed white squares representing the initial position of the dots as digitally recorded. Pressure is applied to the container 762 by a sheet of transparent glass 788 as is represented by force arrows 790-794, while water agitation is represented by curled arrows, certain of which are identified at 796. With the arrangement shown, the clinician may observe the extent of shrinkage through the transparent glass sheet 788 and transparent conformal container 762 as represented at eye station 798.

Figure 54:
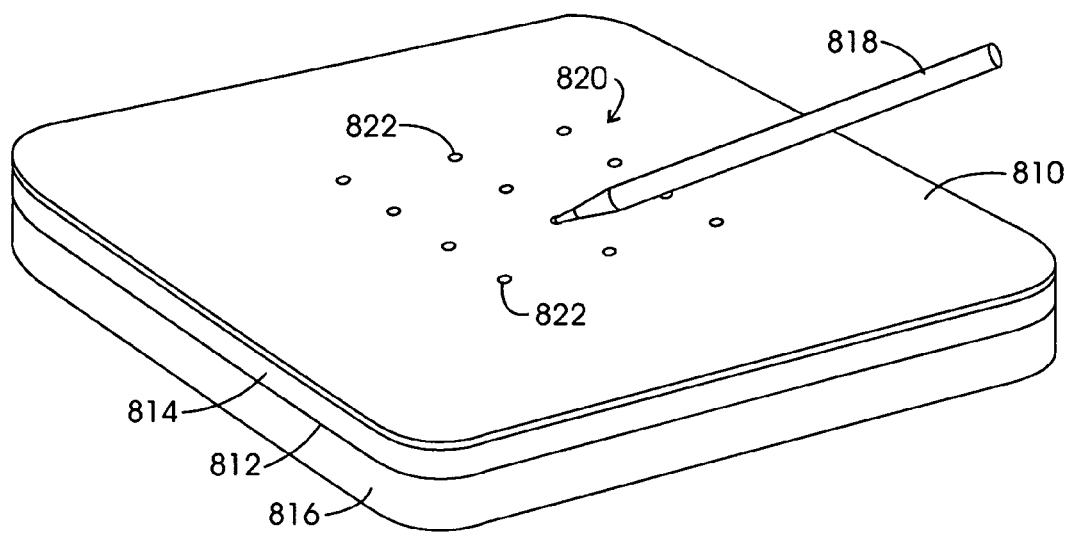
FIG. 54 is a perspective schematic representation of skin, the upper surface of which is being marked to provide a visible dot matrix.
Figure 55:
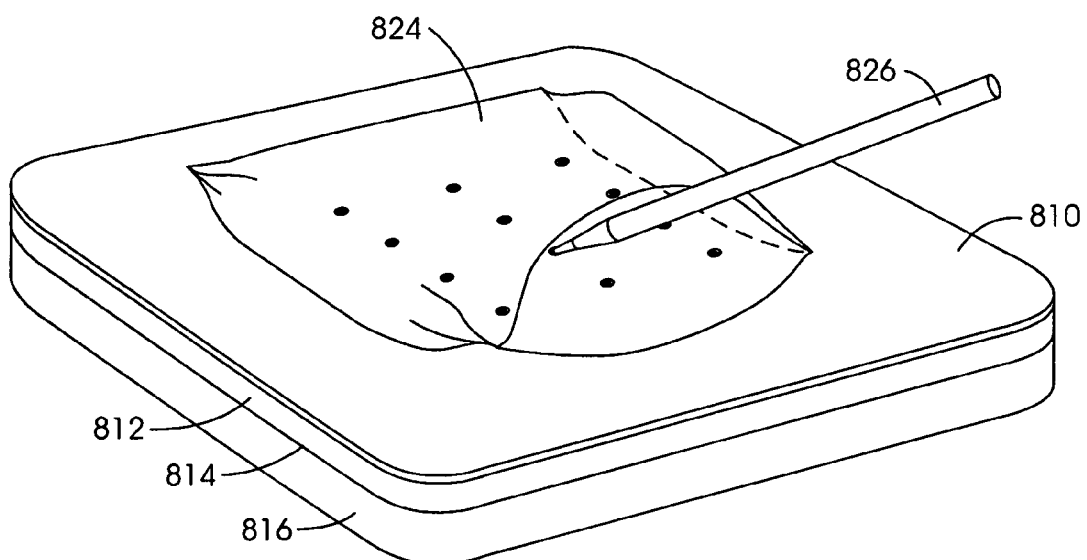
FIG. 55 is a perspective view showing the skin of FIG. 56 with the interior of the contact surface of a conformal transparent heat sink being marked with dots which coincide with those shown in FIG. 54.

In the above discourse, discussion was provided describing a location of a matrix of visible indicia or dots on the surface of epidermis. These indicia may be generated with an alcohol dissolvable ink. Looking to FIG. 54, tissue is schematically portrayed which includes an epidermis 810 underlying which is dermis 812 which establishes an interface 814 with the next adjacent subcutaneous tissue or fat layer 816. An appropriate hand-held ink marker 818 is illustrated forming a matrix of visible indicia represented generally at 820 and fashioned of discrete dot-like indicia, certain of which are identified at 822. Where a transparent conformal container or bag is utilized to retain water for heat sink purposes, the inside of the bag over the contact surface may be employed to provide an initial position matrix of dots or visible indicia prior to the container being filled with water. Looking to FIG. 55, such an unfilled conformal container is seen having been positioned over the matrix 820 (FIG. 54). A clamping assembly has not closed the bag 824 and a marker 826 is shown marking the inside of the container over its contact surface with a matrix of dots or visible indicia which are in registry of those of matrix 820. Subsequent to this marking, the container 824 is filled with water and associated agitation assembly. Then it is clamped closed and the dots so formed by marker 826 are retained in registry with the indicia as at 822 of matrix 820.

Figure 56:
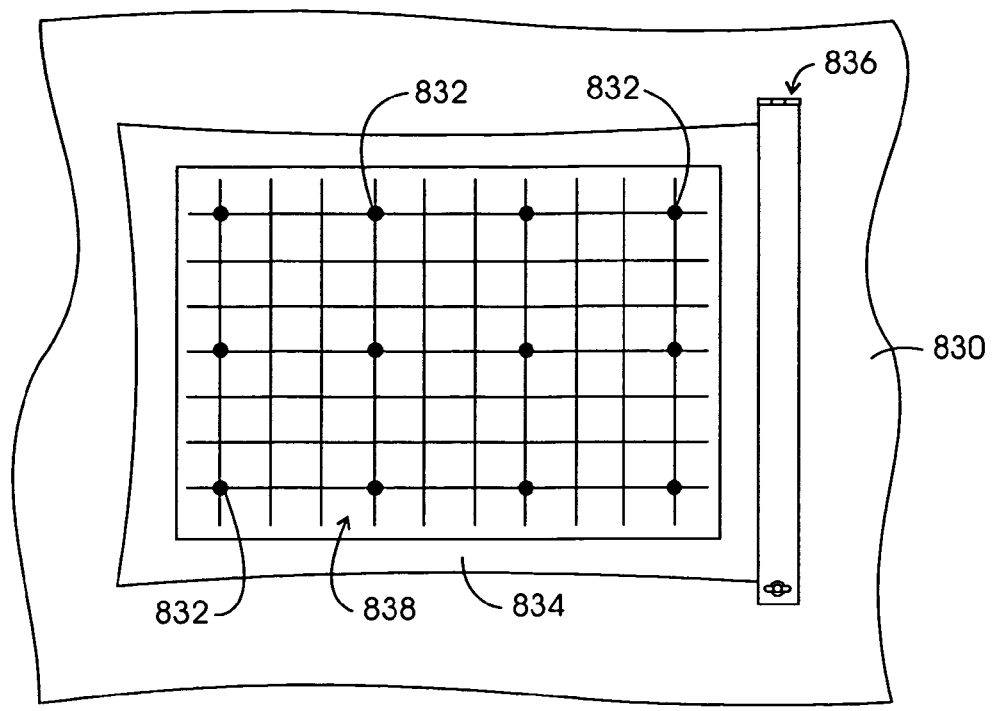
FIG. 56 is a top schematic view of a conformal transparent heat sink showing the inward side of its contact surface carrying a grid having intersections matching a skin carried dot matrix.

Another approach to developing this visible indicia-based evaluation is illustrated in FIG. 56. In that figure, the surface of epidermis is shown at 830. A template guided and controlled matrix of visible indicia as represented by dots, certain of which are identified at 832, is then marked upon the epidermis surface 830. A transparent polymeric conformal container-type heat sink or bag as at 834 is provided being filled with liquid and clamped with a clamping assembly represented generally at 836. The contact surface of container 834, however, is formed with a pre-printed grid represented generally at 838, certain intersections of which correspond with the location of dots or indicia 832. With the arrangement, relative motion of the dots or visible indicia 832 can be readily evaluated with respect to grid 838.

Figure 57:
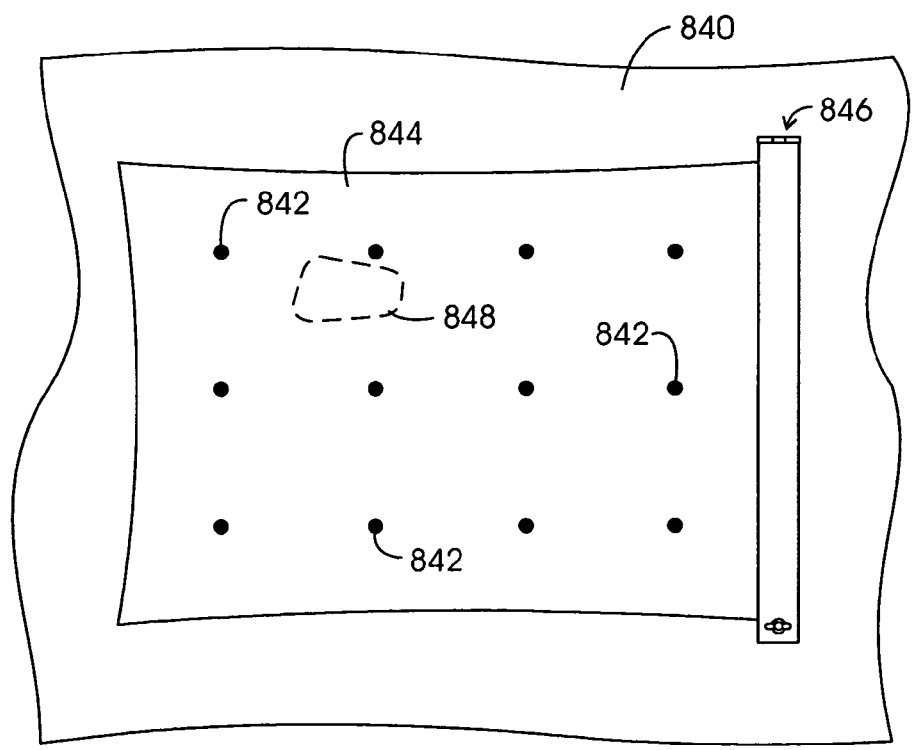
FIG. 57 is a top schematic view of a transparent conformal heat sink, the contact surface of which is coated with a thermochromic material and showing a region of heat induced coloration of such material.

The transparent polymeric conformal containers or bags also can be employed to incorporate a temperature safety indicator. The contact surface of a water-filled heat sink is provided to support a thin transparent layer of reversible thermochromic ink. Should any region of that thermochromic material experience a temperature at or above a skin surface limit temperature, for example, 40° C., then that region will change color and be observable through the transparent heat sink by the clinician. Where such a region is seen, for example, to be changing from a clear to a red coloration, the procedure can be shut down immediately. Looking to FIG. 57, the surface of epidermis is represented at 840 again carrying a matrix of dot-like visible indicia, certain of which are represented at 842. Over this matrix region there is positioned a water-filled transparent conformal heat sink container 844 which is clamped closed by a clamp assembly represented generally at 846. The container 844 additionally will incorporate appropriate water agitation and/or circulation assemblies (not shown). Shown as a dashed boundary 848 observable through heat sink 844 is a region experiencing a thermochromic color change representing an exceeding of a skin surface limit temperature. The presence of such a region 848 will alert the clinician to terminate the procedure forthwith.

Figure 58:
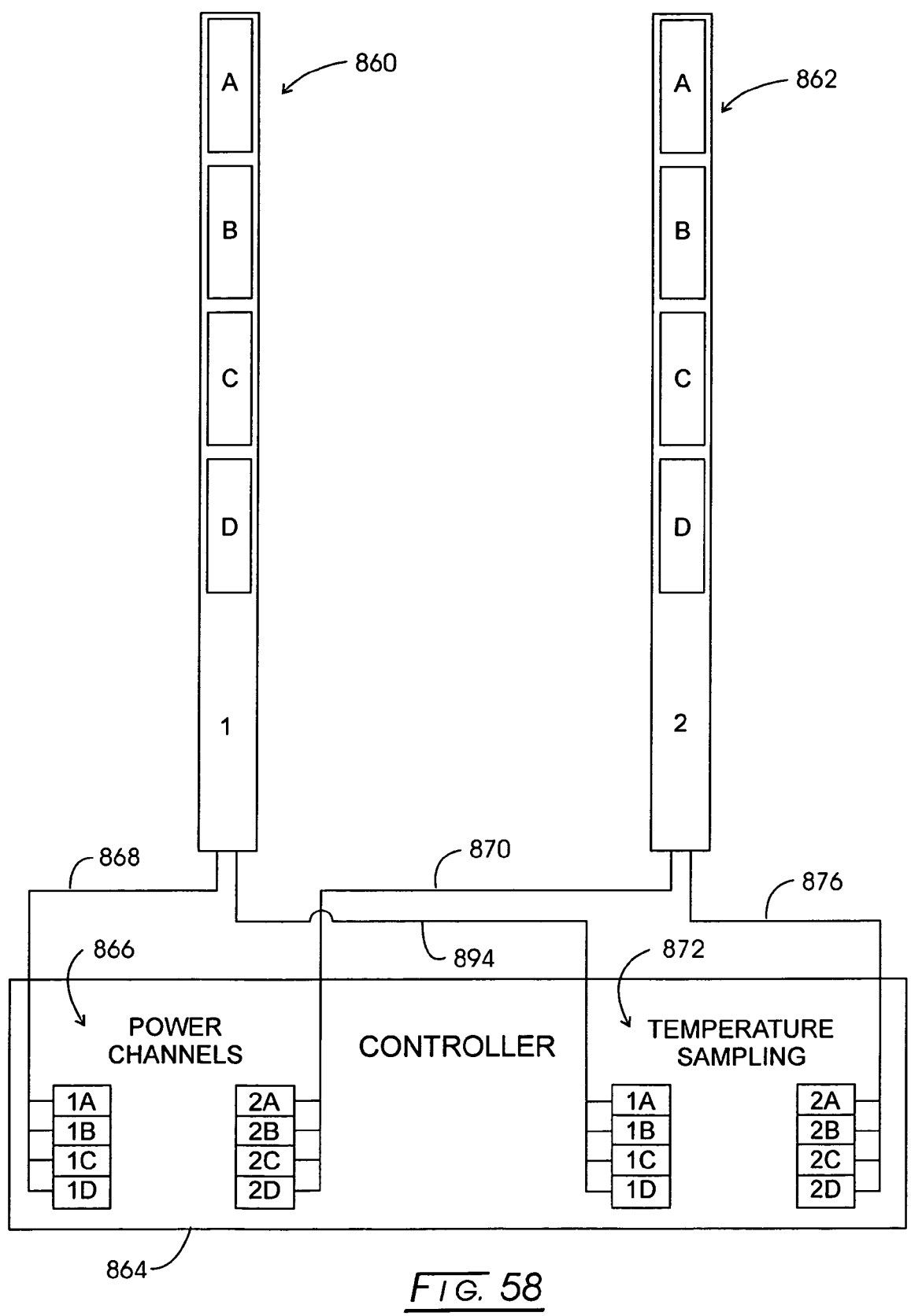
FIG. 58 is a schematic representation of a controller performing in conjunction with two four channel implants configured according to the invention.

Referring to FIG. 58, a controller arrangement for use with a four resistor segment implant as described in connection with FIGS. 29-35 is schematically illustrated. Accordingly, two implants are revealed and identified in general at 860 and 862. Implants 860 and 862 are represented in a parallel relationship and as noted above, without more, their edge-to-edge spacing generally will be about 5 mm. In the course of the heating performance of the resistor segments on these implants segment resistance value will be intermittently sampled to determine corresponding resistor segment temperature. For the instant demonstration, implant 860 is designated as implant No. 1 and implant 862 is represented as implant No. 2. A controller for operation in conjunction with implants 860 and 862 is schematically represented at 864. Controller 864 performs in conjunction with eight resistor segment power channels as represented generally at 866. In this regard, one channel of the resistor segment system extends to resistor segments A-D of implant No. 1 as represented at 1A-1D and line 868. Correspondingly, d.c. electric power is provided at resistor segments 2A-2D of implant No. 2 as represented by line 870. The temperatures of the resistor segments are periodically sampled by evaluating their resistance values. Controller 864 then compares those sample resistance values with a resistance value corresponding with setpoint temperature to develop a control over thermal output. The temperature sampling function of controller 864 is represented in general at 872. Segments 1A-1D of implant 860 are sampled for resistance value as represented at line 874, while the corresponding temperature sampling at implant 862 for segments 2A-2D is represented at line 876.

Now considering the sampling of resistor segments to measure temperature at the situs of the resistor segments, once the implant has been located within heater channels and preferably following the positioning of a heat sink at the skin region of interest, the temperature of each segment prior to therapy is determined. For instance, this predetermined resistor segment temperature, $T_{RS,t0}$, is based on an algorithm related to the measured skin surface temperature, $T_{skin,t0}$, which may be expressed as follows:

$$T_{RS,t0} = f(T_{skin,t0}). \qquad (2)$$

When the associated controller is instructed to commence auto-calibration the following procedure may be carried out:

a. The controller measures the resistance of each resistor segment preferably employing a low-current DC resistance measurement to prevent current induced heating of those resistors.

b. Since the resistor component is metal having a well-known, consistent and large temperature coefficient of resistance, α having a value preferably greater than 3000 ppm/° C. (a preferred value is 3800 ppm/° C.), then the target (setpoint) resistance for each Resistor Segment can be calculated using the relationship:

$$R_{RSi,target} = R_{RSi,t0}(1 + \alpha^*(T_{RS,t} - T_{t0})) \qquad (3)$$

where:
$R_{RSi,t0}$=measured resistance of Resistor Segment, i, at imputed temperature of Resistor Segment under skin, $T_{RS,to}$
α=temperature coefficient of resistance of resistor segment.
$T_{RS,t}$=target or setpoint treatment temperature.
$T_{RS,t0}$=Imputed temperature of resistor segment residing under the skin and prior to the start of any heating.

For four-point sensor resistor connections, no accommodation need be made for the impedance exhibited by the cable extending to the controller. Temperature evaluations are made intermittently, for example, every 500 milliseconds and the sampling interval may be quite short, for example, 2 milliseconds.

Figure 59:
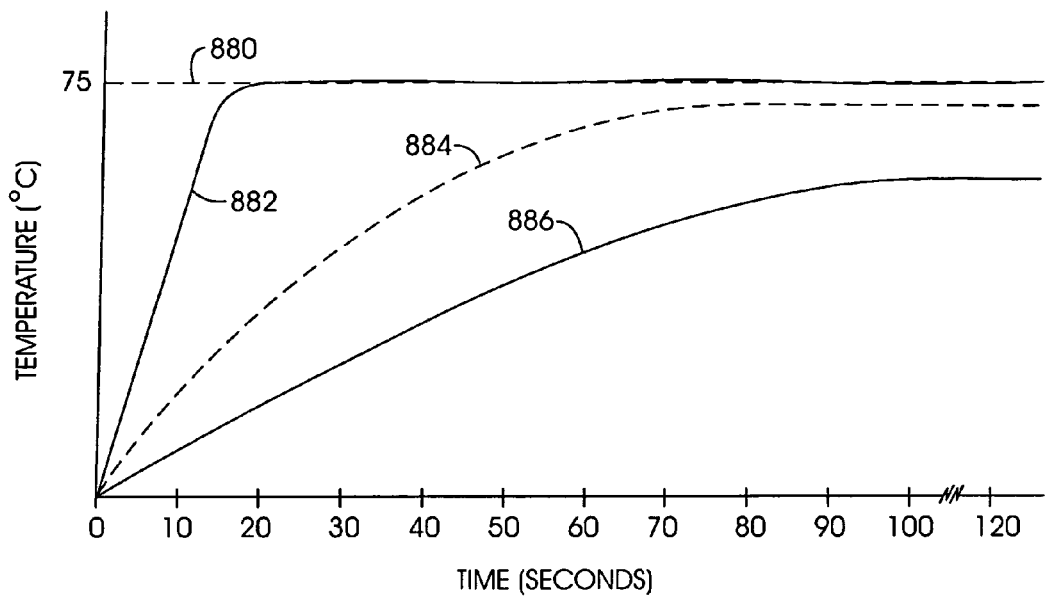
FIG. 59 is a chart relating temperature and time with respect to resistor segment invoked heat-up profiles.

Looking to FIG. 59 and harkening back to FIG. 11 and the discussion concerning zones A and B associated therewith, the characteristics of dermis heating are illustrated. The heater resistor segments of the present implants generally exhibit a low thermal mass and dermis region heat-up will be by conduction heat transfer at a slower pace than the heat-up of the resistor segments themselves. In FIG. 59, the heat-up characteristics of the resistor segments as well as dermis region zones A and B as they respond to thermal migration over time are portrayed. In the figure, a setpoint temperature of 75° C. is represented at horizontal dashed line 880. Curve 882 represents the temperature of the resistor segment being heated. Note that it heats to setpoint temperature at line 880 quite rapidly, for instance, within about 15 seconds. The temperature sampling-based control show an accurate regulation about level 880, for example, within +/−0.5° C. It is anticipated that that differential can be improved, for example to +/−0.1° C. with enhanced sampling rates. Curve 884 tracks temperature development or thermal migration across the region of dermis as it is related to earlier-described zone A identified at dashed boundaries 138 and 140 in FIG. 11. Curve 884 shows that conduction thermal migration reaches to within about 4-5° C. of the setpoint at dashed line 880 within about 60-70 seconds. For this conduction heat transfer, good thermal contact is called for between the resistor segment and dermis. In this regard, the system is quite susceptible to extremely small gaps or a dry interface as discussed above in connection with FIG. 13. The 4° C. to 5° C. drop below setpoint temperature is occasioned by the thermal impedance of the interface between dermis and the heated surface which includes the polyimide layer as described in FIGS. 33, 38A and 38B. Zone B has been described at 142-145 in FIG. 11. That zone B represents a region extending about 2 mm outboard of the edges of the implants. The heat-up or thermal migration characteristic for zone B is represented at curve 886 in FIG. 59. In this regard, the curve reaches within about 10° C. of setpoint level 880 within about 90 to 120 seconds. It should be noted, however, that the resultant dermis region temperature, for example, about 65° C. for the instant example is sufficient to evoke collagen shrinkage.

For purposes of description, the temperature increase from the initial temperature of the tissue to be treated to the temperature necessary to achieve effective therapy is herein designated as $\Delta T$, i.e. the temperature elevation. For example, the initial temperature of the tissue, such as, face tissue, may be approximately 33° C. The temperature of the collagen shrinkage domain generally extends from about 65° C. to about 75° C. Thus the minimum $\Delta T$ necessary to enter the collagen shrinkage domain would be 32° C., and the maximum acceptable $\Delta T$ in this example is 42° C.

A number of substances have been identified that interact with the ECM of dermis and alter the thermally responsive properties of its collagen fibers. As described herein, substances with such properties are termed "adjuvants." A variety of such substances are known that function as temperature setpoint lowering adjuvants wherein utilization of such an adjuvant lowers the temperature elevation ($\Delta T$) required to induce collagen shrinkage, i.e., lowers the thermal transformation temperature. The amount of reduction of the $\Delta T$ produced by a given concentration of a given adjuvant is identified herein as the $\Delta T_a$. It will be recognized by those skilled in the art of protein structural chemistry that the reduction in length of collagen fibers, i.e. shrinkage, is a result in part of an alteration of the physical structure of the molecular structure of the collagen fibers. The internal ultrastructure of collagen fibers, being comprised of tropocollagen molecules aggregated into collagen fibrils, and then aggregated further into even larger collagen fibers, is a result of complex interactions between the individual tropocollagen molecules, and between molecules associated with the collagen fibers, for example, elastin, and hyaluronan. The molecular forces of these interactions include covalent, ionic, disulphide, and hydrogen bonds; salt bridges; hydrophobic, hydrophilic and van der Waals forces. In the context of the invention, adjuvants are substances that are capable of inducing or assisting in the alteration of the physical arrangement of the molecules of the skin in order to induce, for instance shrinkage. With respect to collagen fibers, adjuvants are useful for altering the molecular forces holding collagen molecules in position, changing the conditions under which shrinkage of collagen can occur.

Protein molecules, such as collagen are maintained in a three dimensional arrangement by the above described molecular forces. The temperature of a molecule has a substantial effect on many of those molecular forces, particularly on relatively weaker forces such as hydrogen bonds. An increase in temperature may lead to thermal destabilization, i.e., melting, of the three dimensional structure of a protein. The temperature at which a structure melts is known as the thermal transformation temperature. In fact, irreversible denaturation of a protein, e.g., cooking, is a result of melting or otherwise disrupting the molecular forces maintaining the three dimensional structure of a protein to such an extent that that once heat is removed, the protein can no longer return to its initial three dimensional orientation. Collagen is stabilized in part by electrostatic interactions between and within collagen molecules, and in part by the stabilizing effect of other molecules serving to cement the molecules of the collagen fibers together. Stabilizing molecules may include proteins, polysaccharides (e.g., hyaluronan, chondroitin sulphate), and ions.

A persistent problem with existing methods of inducing collagen shrinkage that rely on heat is that there is a substantial risk of damaging and or killing adipose (fat layer) tissue underlying the dermis, resulting in deformation of the contours of the overlying tissues, with a substantial negative aesthetic effect. Higher temperatures or larger quantities of energy applied to the living cells of the dermis can moreover result in irreversible damage to those cells, such that stabilization of an altered collagen network cannot occur through neocollagenesis. Damage to the living cells of the dermis will negatively affect the ability of the dermis to respond to treatment through the wide variety of healing processes available to the skin tissue. Adjuvants that lower the $\Delta T$ required for shrinkage have the advantage that less total heat need be applied to the target tissue to induce shrinkage, thus limiting the amount of heat accumulating in the next adjacent subcutaneous tissue layer (hypodermis). Reducing the total energy application is expected to minimize tissue damage to the sensitive cells of the hypodermis, thereby limiting damage to the contour determining adipose cells.

One effect of adjuvants with respect to the instant discourse is that certain biocompatible reagents have the effect of lowering the temperature required to begin disruption of certain molecular forces. In essence, adjuvants are capable of reducing the molecular forces stabilizing the ultrastructure of the skin, allowing a lower absolute temperature to induce shrinkage of the collagen network that determines the anatomy of the skin. Any substance that interferes with the molecular forces stabilizing collagen molecules and collagen fibers will exert an influence on the thermal transformation temperature (melting temperature). As collagen molecules melt, the three dimensional structure of collagen undergoes a transition from the triple helix structure to a random polypeptide coil. The temperature at which collagen shrinkage begins to occur is that point at which the molecular stabilizing forces are overcome by the disruptive forces of thermal transformation. Collagen fibers of the skin stabilized in the ECM by accessory proteins and compounds such as hyaluronan and chondroitin are typically stable up to a temperature of approximately 58° C. to 60° C., with thermal transformation and shrinkage occurring in a relatively narrow phase transition range of 60-70° C. Variations of this transition range are noted to occur in the aged (increasing the transition temperature) an in certain tissues (decreasing by 2-4° C. in tendon collagen). In effect the lower temperature limit of the collagen shrinkage domain is determined by the thermal transformation temperature of a particular collagen containing structure.

It will be recognized by those skilled in molecular biology that the thermal transformation temperature necessary to achieve a reduction in skin laxity may not entirely be determined by the thermal transformation temperature of collagen fibers, but may also be affected by a variety of other macromolecules present in the dermis, including other structural proteins such as elastin, fibronectin, heparin, carbohydrates such as hyaluronan and other molecules such as water and ions.

Substances exhibiting the properties desirable for lowering the $\Delta T$ include enzymes such as hyaluronidase collagenase and lysozyme; compounds that destabilize salt bridges, such as beta-naphtalene sulphuric acid; each of which is expected to reduce the $\Delta T$ by 10-12° C., and substances that interfere with hydrogen bonding and other electrostatic interactions, such as ionic solutions, such as calcium chloride or sodium chloride; detergents (a substance that alters electrostatic interactions between water and other substances), such as sodium dodecyl sulphate, glycerylmonolaurate, cationic surfactants, or N,N, dialkyl alkanolamines (i.e. N,N-diethylethanolamine); lipophilic substances (lipophiles) including steroids, such as dehydroepiandrosterone, and oily substances such as eicosapentanoic acid; organic denaturants, such as urea; denaturing solvents, such as alcohol, ethanol, isopropanol, acetone, ether, dimethylsulfoxide (DMSO) or methylsulfonylmethane; and acidic or basic solutions. The adjuvants that interfere with hydrogen bonding and other electrostatic interactions may reduce the $\Delta T$ for the shrinkage transition by as much as 40° C. depending on the concentration and composition of the substances administered. The $\Delta T_a$ of a particular adjuvant in use will be dependent on the chemical properties of the adjuvant and the concentration of adjuvant administered to the patient. For enzymatic adjuvants such as hyaluronidase, the $\Delta T_a$ is also dependent on the specific activity of the delivered enzyme adjuvant in the dermis environment.

Adjuvants suitable for use with the instant subject matter would desirably be compatible with established medical protocols and be safe for use in human patients. Adjuvants should be capable of rapidly infiltrating the targeted skin tissue, should cause minimal negative side effects, such as causing excess inflammation, and should preferably persist for the duration of the procedure. Suitable adjuvants may be, for instance, combined with local anesthetics used during treatment, be injectable alone or in combination with other reagents, be heat releaseable from the implants of the invention, or be capable of entering the targeted tissue following topical application to the skin surface. Certain large drug molecules, such as enzymes functioning as adjuvants according to the invention may be drawn into the target dermal tissue through iontophoresis (electric current driving charged molecules into the target tissues) The exact mode administration of adjuvants will be dependent on the particular adjuvant employed.

In a preferred embodiment, the thermal transition temperature lowering adjuvant is present in highest concentrations in the tissues of the dermis. For highest efficacy, a concentration gradient is established, wherein the adjuvant is at a higher concentration in the dermis that in the hypodermis. A transdermal route of administration is one preferred mode of administration, as will occur with certain topical adjuvants. For adjuvants that are applied topically to the surface of the skin, for instance as a pomade, as the adjuvant either diffuses or is driven across the epidermis, and passes into the dermis, a concentration gradient is established wherein the adjuvant concentration is higher in the dermis than in the hypodermis. Because the collagen matrix is much more prevalent in the dermis than in the epidermis, presence of the adjuvant in the epidermis is expected to be without negative effect. Certain adjuvants, for instance, enzymes with collagen binding activity, would be expected to accumulate in the dermal tissue.

A variety of methods are known wherein drugs are delivered to the patient transdermally, i.e. percutaneously, through the outer surface of the skin. A variety of formulations are available that enhance the percutaneous absorption of active agents. These formulations may rely on modification of the active agent, or the vehicle or solvent carrying that agent. Such formulations may include solvents such as methylsulfonylmethane, skin penetration enhancers such as glycerylmonolaurate, cationic surfactants, and N, N, dialkyl alkanolamines such as N,N-diethylethanolamine, steroids, such as dehydroepiandrosterone, and oily substances such as eicosapentanoic acid. For further discussion of enhancers of transdermal delivery of active agents, for instance adjuvants according to the invention, see: U.S. Pat. No. 6,787,152 to Kirby et al., issued Sep. 7, 2004; and U.S. Pat. No. 5,853,755 to Foldvari, issued Dec. 29, 1998.

When adjuvants are injected, it is preferable that they be deposited as close to the dermis as practicable, preferably, intradermally. Because the dermis is relatively thin, and difficult to penetrate with hypodermic needles, the adjuvants may be delivered subdermally, or at the interface between the dermis and the next adjacent subcutaneous tissue (hypodermis or adipose tissues underlying the dermis). Even to the extent that adjuvants are delivered into the adipose tissue of the hypodermis, because the hypodermis is typically very thick compared to the dermis, a concentration gradient will develop, wherein the adjuvant will diffuse quickly into the dermis, and fully equilibrate with the dermal tissue, before the adjuvant has fully equilibrated with the hypodermis.

In a further embodiment, the implants carry a surface coating of adjuvant that is released into the dermis upon activation of the implant. It is an advantage that when utilizing ΔT lowering adjuvants that the implants are placed very near the location where adjuvants can provide the most benefit. A number of compositions are known in the art that can be released from an implant by heating of the implant. For example, the upper, or dermis facing, surface of the implant can be coated with microencapsulated adjuvant, for instance hyaluronan. Once a preliminary heating of the implant begins, the encapsulated adjuvant is released, and immediately begins diffusing into the dermis tissue, as the implant is already in place at the interface between the dermis and hypodermis. As the adjuvant diffuses through the dermis, a concentration gradient develops wherein the adjuvant is at the greatest concentration in the dermis, with reduced concentrations in the epidermis and hypodermis. Following this preliminary heating, regular heating-up to a lowered setpoint temperature may be carried out. As described previously, while it is not a requirement that the adjuvant be at greatest concentration in the dermis (for instance, if the adjuvant is applied topically to the skin surface), it is considered an advantage to for the adjuvant to be at the greatest concentration in the tissue layer wherein adjuvant activity is needed.

In a further embodiment of implant delivery of the adjuvant, the adjuvant is encapsulated in liposomes and suspended in a compatible vehicle. The surfaces of the implant to be inserted into the patient are then coated with the liposome/vehicle composition. When the implant is inserted into the tissue of the patient, the vehicle coating, preferably moderately water soluble and biologically inert, prevents the adjuvant from being displaced from the implant surface for the period of time necessary for insertion. Once the implant is activated on the noted preliminary basis, the dermis facing upper surface of the implant is heated and the liposomes encapsulating the adjuvant are induced by heat to release the adjuvant. Different compositions of liposomes are useful for providing release of the adjuvant at a particular temperature range. Similarly, the vehicle binding the adjuvant encapsulating liposomes to the implant can be chosen so that the vehicle does not release the liposomes themselves unless a desired temperature has been reached. In this manner the release of adjuvant from an implant surface may be configured so that the adjuvant is released in a directional manner, even though the entire implant surface is coated with an adjuvant composition. Those skilled in the art will recognize that a variety of heat releaseable encapsulating systems are available for use in delivering adjuvant. Further discourse on the composition of liposomes is available by referring to U.S. Pat. No. 5,853,755 (supra).

The following discourse specifically describes certain embodiments of specific adjuvants that are useful for the present purpose. Artisans will recognize that other substances known in the art to have similar effects will be useful as adjuvants, and thus, the following embodiments should not be considered as limiting.

Hyaluronidase is an enzyme that cleaves glycosidic bonds of hyaluronan, depolymerizing it and, converting highly viscous polymerized hyaluronan into a watery fluid. A similar effect is reported on other acid mucopolysaccharides, such as chrondroitin sulphate. Hyaluronidase is commercially available from a number of suppliers (e.g., Hyalase, C. P. Pharmaceuticals, Red Willow Rd. Wrexham, Clwydd, U.K.; Hylenex, Halozyme Therapeutics (human recombinant form); Vitrase, (purified ovine tissue derived form) ISTA Pharmaceuticals; Amphadase, Amphastar Pharmeceuticals (purified bovine tissue derived)).

Hyaluronidase modifies the permeability of connective tissue following hydrolysis of hyaluronan. As one of the principal viscous polysaccharides of connective tissue and skin, hyaluronan in gel form, is one of the chief ingredients of the tissue cement, offering resistance to the diffusion of liquids through tissue. One effect of hyaluronidase is to increase the rate of diffusion of small molecules through the ECM, and presumably to decrease the melting temperature of collagen fibers necessary to induce shrinkage. Hyaluronidase has a similar lytic effect on related molecules such as chondroitin sulphate. Hyaluronidase enhances the diffusion of substances injected subcutaneously, provided local interstitial pressure is adequate to provide the necessary mechanical impulse. The rate of diffusion of injected substances is generally proportionate to the dose of Hyaluronidase administered, and the extent of diffusion is generally proportionate to the volume of solution administered. The addition of hyaluronidase to a collagen shrinkage protocol results in a reduction of the $\Delta T$ required to induce 20% collagen shrinkage by about 12° C. Review of pharmacological literature reveals that doses of hyaluronidase in the range of 50-1500 units are used in the treatment of hematomas and tissue edema. Thus, local injection of 1500 IU hyaluronidase in 10 ml vehicle into the target tissue is predicted to reduce the temperature necessary to accomplish 20% shrinkage of collagen length from about 63° C. to about 53° C. For multiple injection sites 100 IU hyaluronidase in 2 ml of alkalinized normal saline or 200 IU/ml are expected to be similarly effective as an adjuvant. The manufacturer's recommendations for Vitrase indicate that 50-300 IU of Vitrase per injection are expected to exert the adjuvant effect. It should be noted that use of salimasa vehicle for delivery of adjventson anesthesia may be contradicted where introduction of excess electrolytes would interfere with operation of the implants.

Hyaluronidase has been used in clinical settings as an adjunct to local anesthesia for many years, without significant negative side effects, and is thus believed to be readily adaptable for use. When used as an adjunct to local anesthesia, 150 IU of hyaluronidase are mixed with a 50 ml volume of vehicle that includes the local anesthetic. A similar quanitity of hyaluronidase is expected to be effective reducing the $\Delta T$ for effecting shrinkage by approximately 10° C., with or without the addition of anesthetic. When hyauronidase is injected intradermally or peridermally, the dermal barrier removed by hyaluronidase activity persists in adult humans for at least 24 hours, with the permeabilization of the dermal tissue being inversely related to the dosage of enzyme delivered (in the range of administered doses of 20, 2, 0.2, 0.02, and 0.002 units per mL. The dermis is predicted to be restored in all treated areas 48 hours after hyaluronidase administration.

Additional background on the activity of hyaluronidase is available by referring to the following publications (and the references cited therein):
18. Lewis-Smith, P. A., "Adjunctive use of hyaluronidase in local anesthesia" *Brit. J. Plastic Surgery,* 39: 554-558 (1986).
19. Clark, L. E., and Mellette, J. R., "The Use of Hyaluronidase as an Adjunct to Surgical Procedures" *J. Dermatol., Surg. Oncol.,* 20:842-844 (1994).
20. Nathan, N., et al., "The Role of Hyaluronidase on Lidocaine and Bupivacaine Pharmaco Kinetics After Peribulbar Blockade" *Anesth Anala.,* 82: 1060-1064 (1996).

See also U.S. Pat. No. 6,193,963 to Stern, et al., issued Feb. 27, 2001.

Lysozyme is an enzyme capable of reducing the cementing action of ECM compounds such as chondroitin sulphate. Lysozyme (aka muramidase hydrochloride) has the advantage that it is a naturally occurring enzyme; relatively small in size (14 kD), allowing rapid movement through the ECM; and is typically well tolerated by human patients. A topical preparation of lysozyme, as a pomade of lysozyme is available (Murazyme, Asta Medica, Brazil; Murazyme, Grunenthal, Belgium, Biotene with calcium, Laclede, U.S.). The addition of lysozyme as an adjuvant to a collagen shrinkage protocol results in a reduction of the $\Delta T$ required to induce 20% collagen shrinkage by about 10-12° C. Additional background on the use of lysozyme to lower the $\Delta T$ for collagen shrinkage is available. See for instance, U.S. Pat. No. 5,484,432 to Sand, issued Jan. 16, 1996.

Those skilled in the art will recognize that a variety of adjuvants that reduce the stability of the collagen fiber, tropocollagen, and or substances that serve to cement these structures are adaptable for use with the instant heater implants. Adjuvant ingredients may include agents such as solvents, such as dimethylsulfoxide (DMSO), monomethylsulfoxide, polymethylsulfonate (PMSF), methylsulfonylmethane, alcohol, ethanol, ether, diethylether, and propylene glycol. Certain solvents, such as DMSO, are known to lead to the disruption of collagen fibers, and collagen turnover. When DMSO is delivered to patients with scleroderma, a condition that exhibits an overproduction of collagen and scar tissue as a symptom, an increase of excretion of hydroxyproline, a constituent of collagen is noted. This is believed to due to increased breakdown of collagen. Solvents that will alter the hydrogen bonding interactions of collagen fibers, such as DMSO and ethanol are predicted to reduce the $\Delta T$ necessary to reach the thermal transition temperature of collagen fibers, with the reduction of $\Delta T$ being expected to be relative to the alteration of the hydrophilicity of the collagen environment by the solvent. Small diffusible solvents such as DMSO and ethanol offer the further advantage of being able to rapidly penetrate the epidermis and reach the dermis tissue, while being generally safe for use in human patients.

In a further embodiment, adjuvants may be used in combination with one another, in a manner that either further lowers the $\Delta T$ either synergistically or additively. Combining adjuvants provides a means to utilize a particular adjuvant to achieve its optimal effect, and when combined with a second adjuvant, further lower the heating necessary to achieve the desired shrinkage, while avoiding adverse side effects associated with higher doses of a particular adjuvant.

Figure 60:
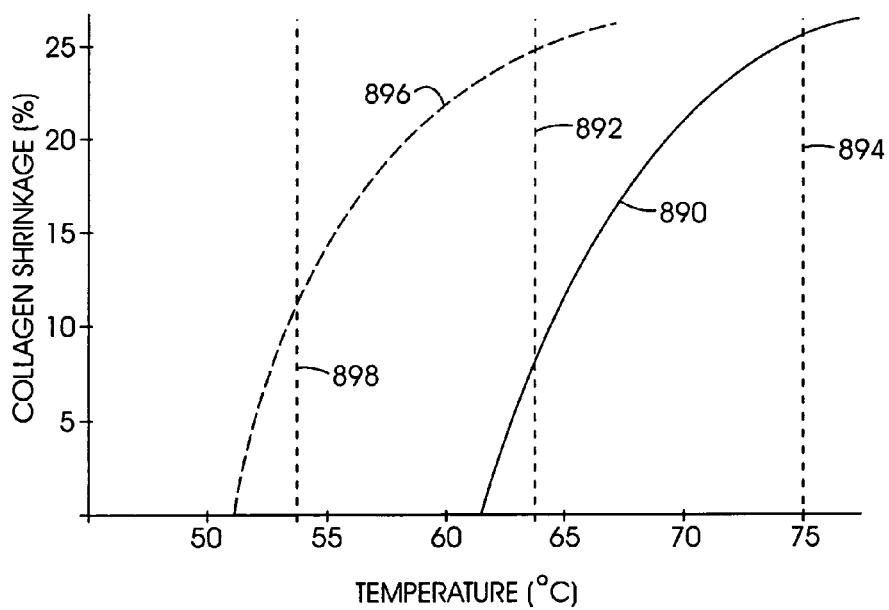
FIG. 60 illustrates two curves relating collagen shrinkage in percent and temperature for a ten minute therapy interval using an adjuvant and not using an adjuvant.
Figure 66F:
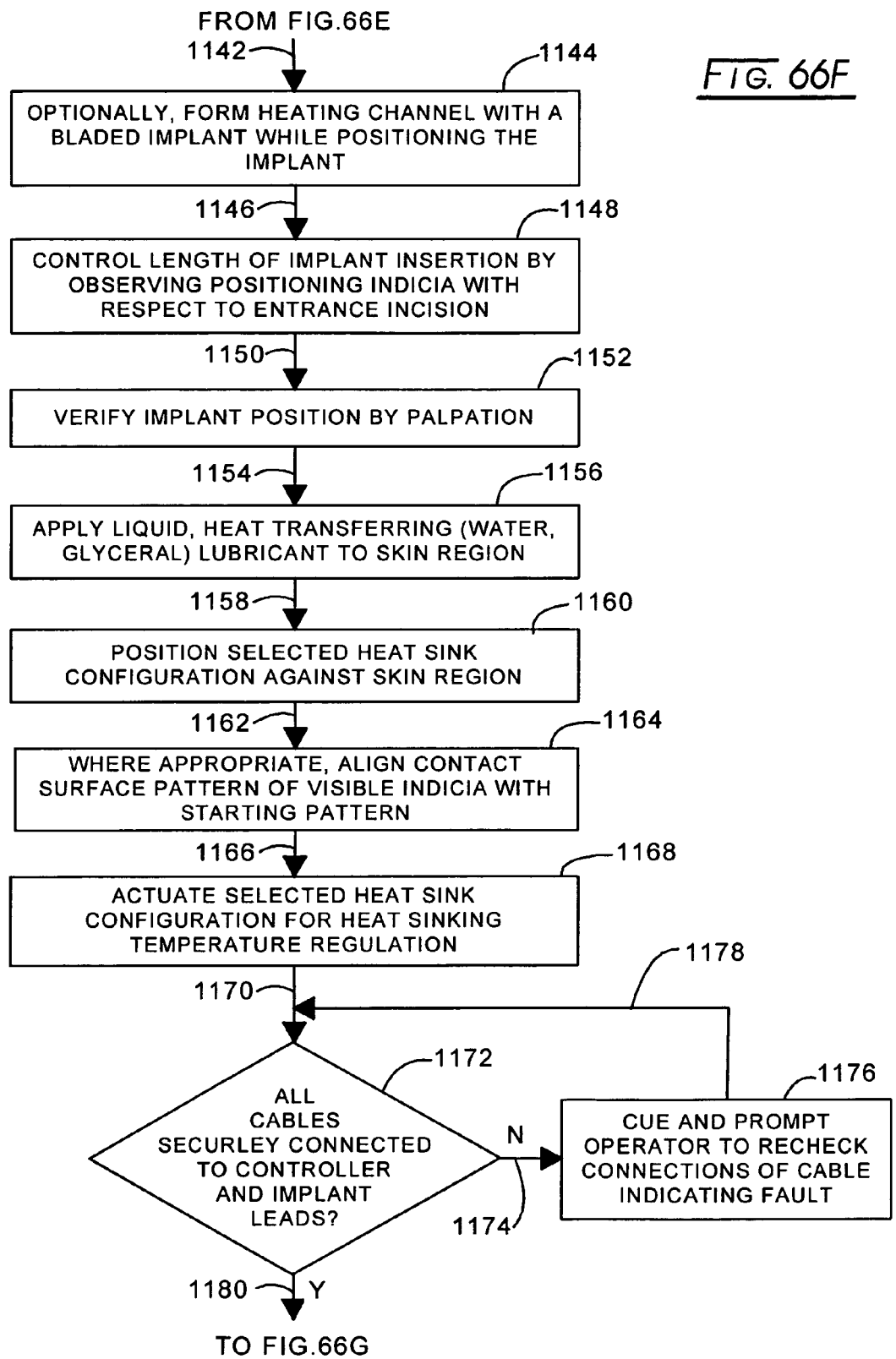
Figure 66H:
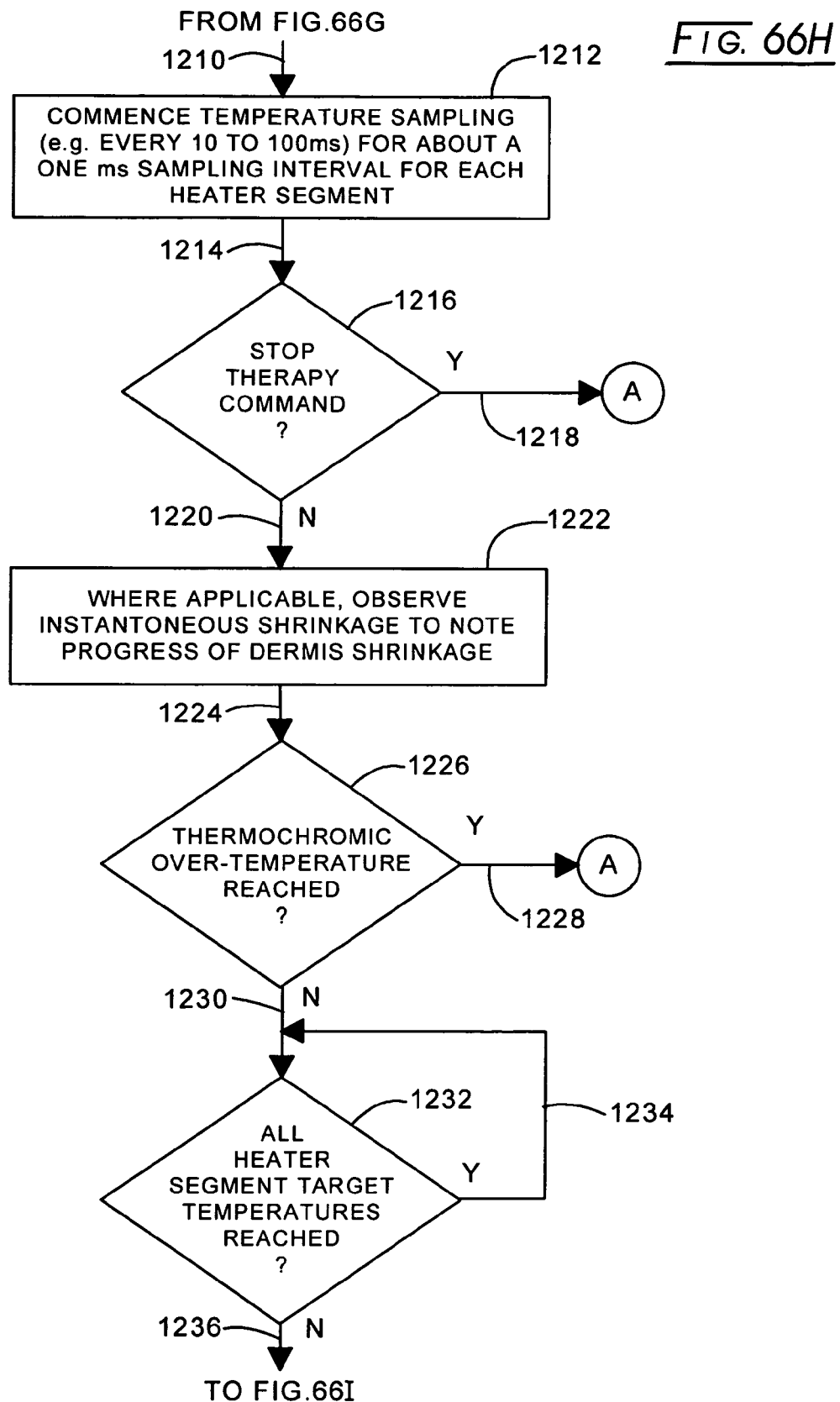
Figure 66J:
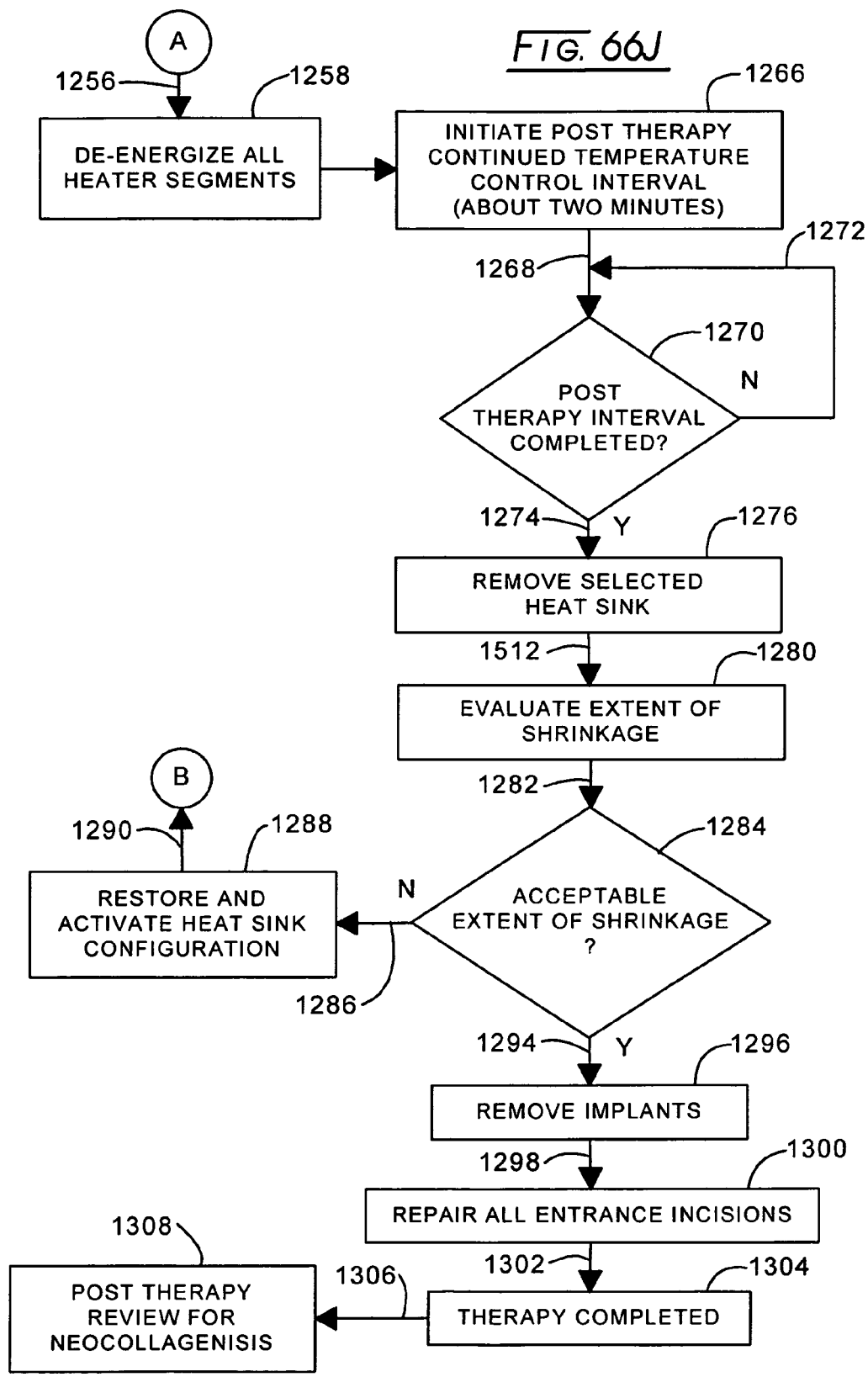
Figure 67A:
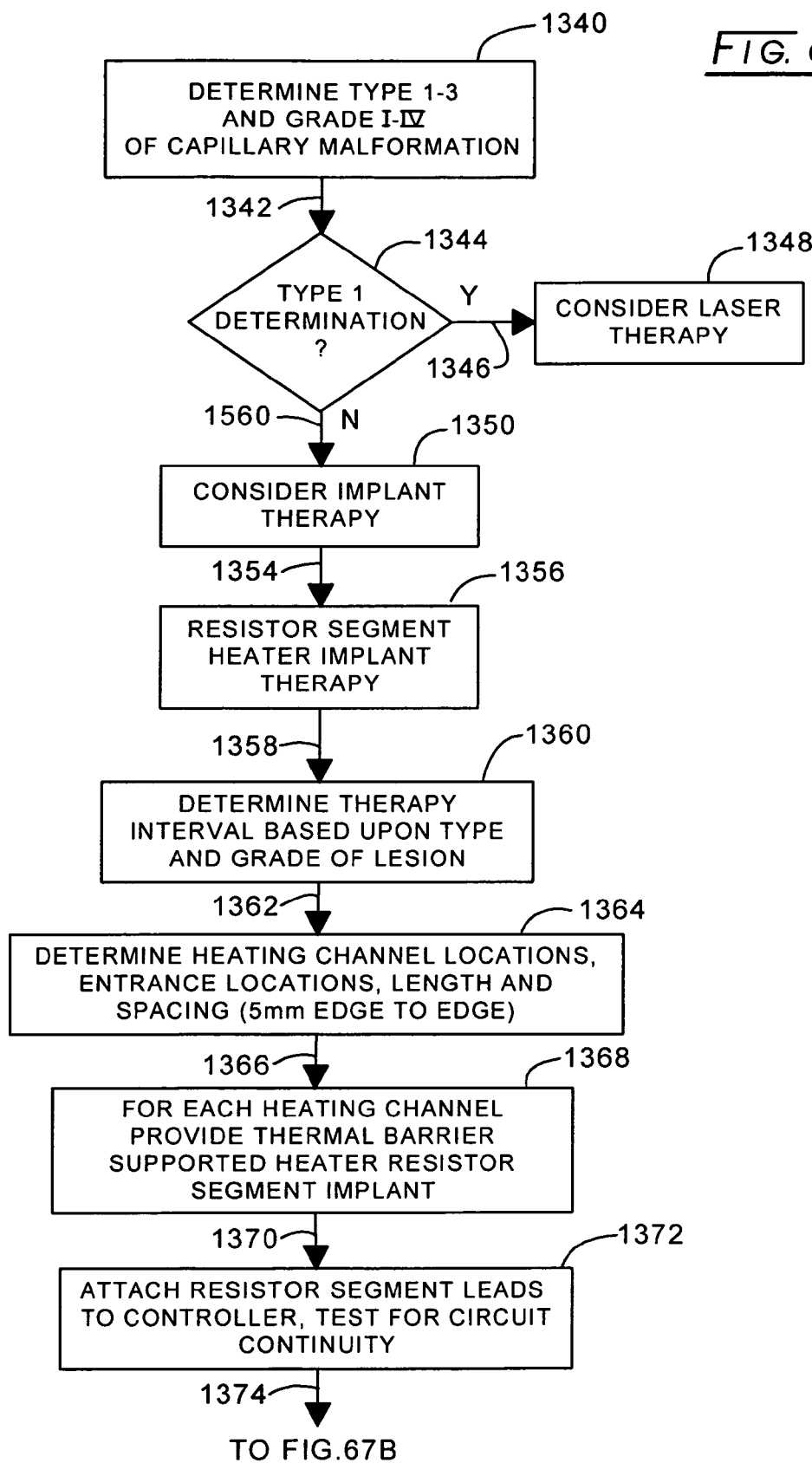
Figure 67D:
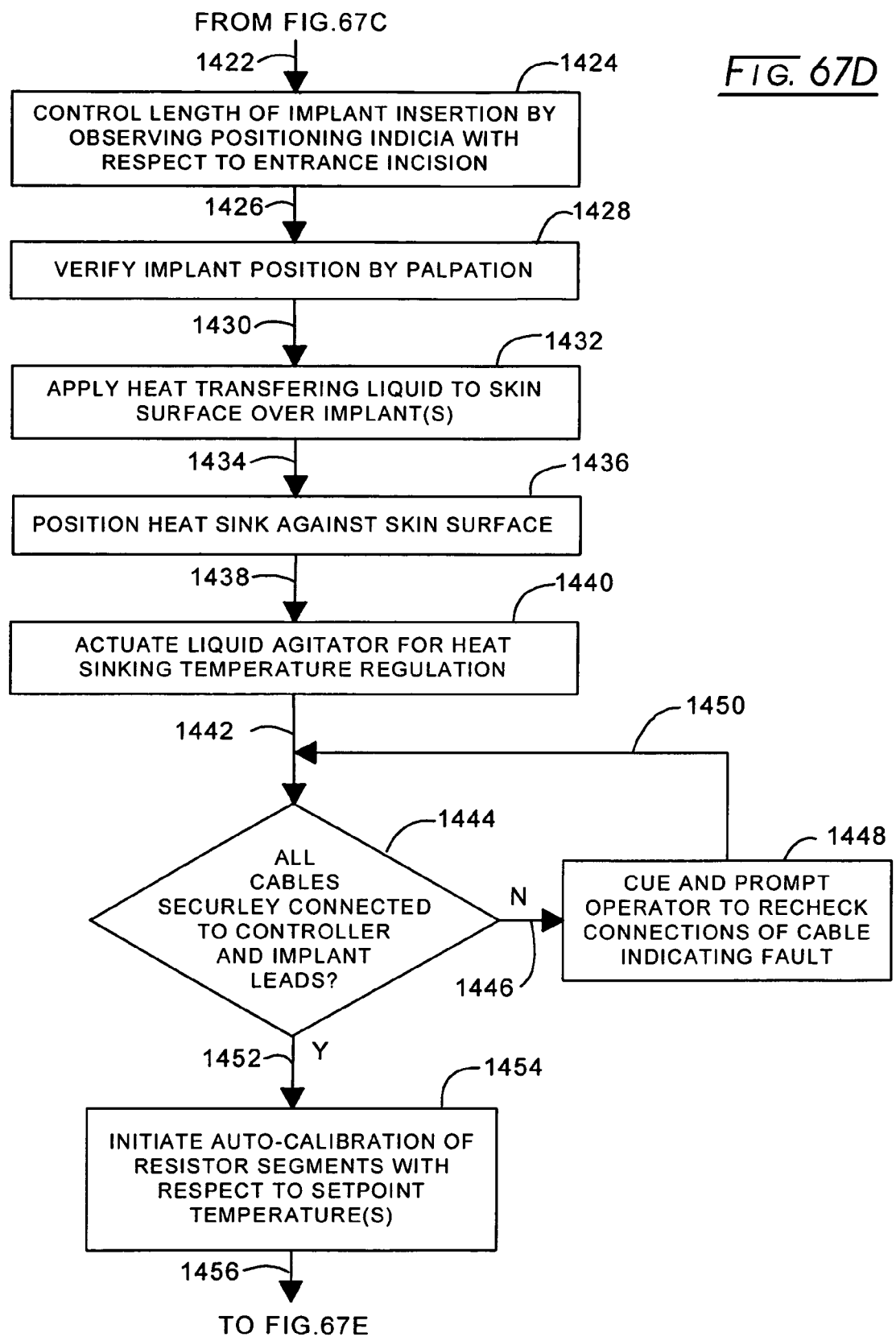
Figure 67F:
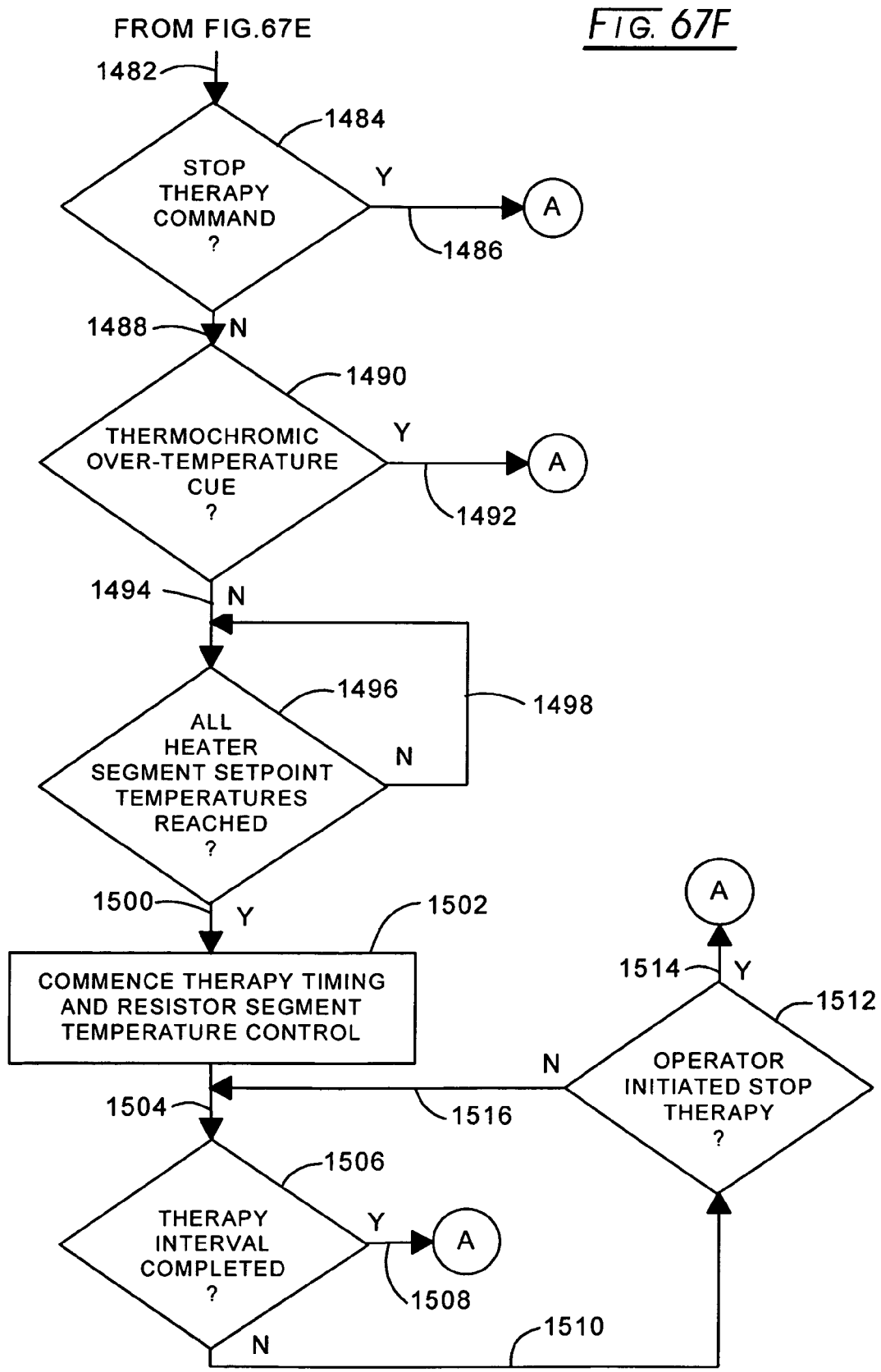
Figure 67G:
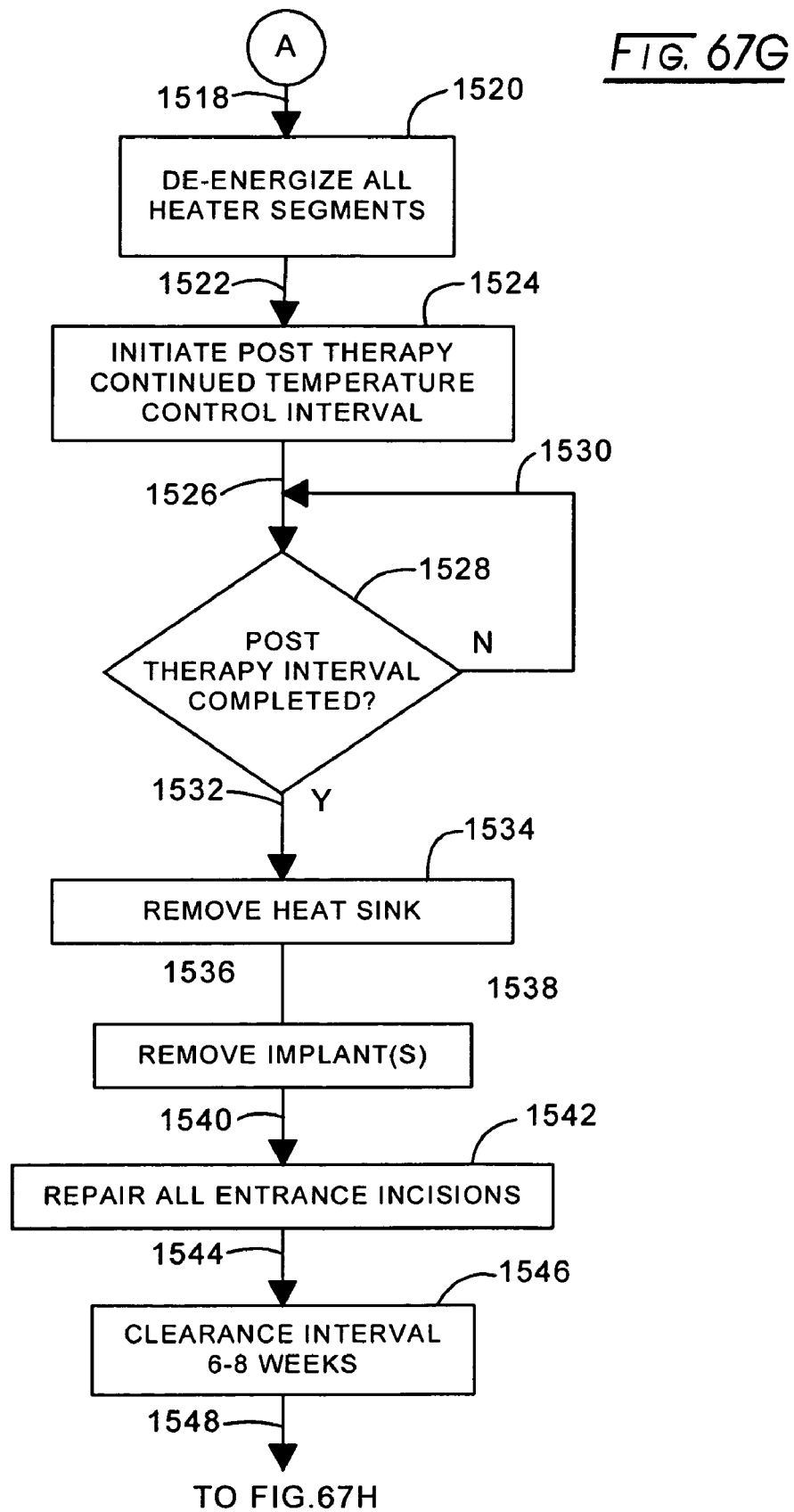
Figure 67H:
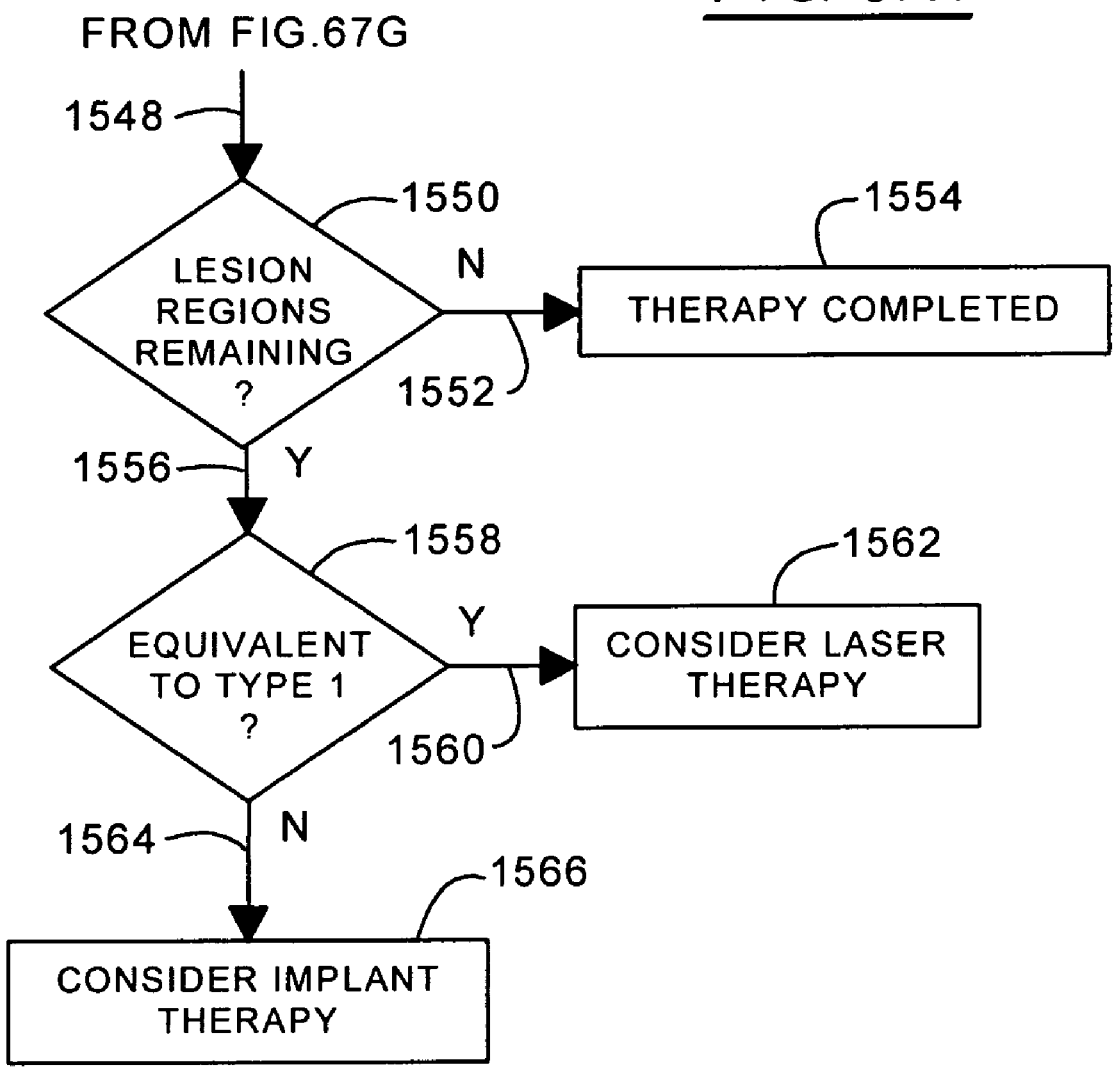

FIG. 60 presents an experience-based representation of the beneficial effects associated with the use of adjuvants in conjunction with this resistor segment based implant technology. The curves in the figure are experientially evolved, representing a ten minute heating time with resistor segment carrying implants spaced edge-to-edge 5 mm apart as discussed in connection with FIG. 11. Hypothetical curve 895 represents the relationship between collagen shrinkage in terms of percent with respect to dermis region temperature without the utilization of an adjuvant. Curve 890 reveals that at about a temperature of 62° C. there is no shrinkage at all, the dermis being below thermal transformation temperature. At about 63° C. as represented at vertical dashed line 892, about 10% collagen shrinkage is realized and at about 70° C. around a 20% collagen shrinkage is realized. At 75° C. the shrinkage approaches 25%, a level of shrinkage considered hazardous and to be avoided. In general, clinicians will desire to work within a collagen shrinkage range of between about 15% and about 20%.

Hypothetical curve 890 should be contrasted with corresponding hypothetical curve 896 which assumes the application of an adjuvant dropping the thermal transition temperature for collagen shrinkage from about 63° C. to about 53° C. Typically, as noted above, the adjuvants will lower that threshold temperature by 10° C. to 12° C. The 75° C. setpoint temperature at dashed line 894 is now 63° C. assuming a 12° C. reduction in threshold. At that 63° C., collagen shrinkage approaches 25%. Such shrinkage will be about 20% at about 58° C. As noted at vertical dashed line 898, 10% collagen shrinkage is realized at 53° C. as opposed to 65° C. By so shifting the threshold transition temperature thermal burden on both epidermis and next adjacent subcutaneous tissue is substantially reduced to avoid the possibility of thermal injury to those important two components.

A stainless steel flat dissecting instrument 540 has been described in connection with FIGS. 44 and 45 which has the function of forming a heating channel through an entrance incision prior to locating an implant within the preformed channel. However, the thermally insulative generally flat polyetherimide thermal barrier and support component of the implant leading end may be bladed so as to enter a skin entrance incision and guidably move under compressive urging along the interface between dermis and next adjacent subcutaneous tissue to form and be located within a heating channel. The bladed leading end can be established in the course of injection molding of the thermal barrier. Looking to FIG. 61, a bladed implant is represented in general at 910. Implant 910, with the exception of its forward end or tip is configured in the manner described at 450 in FIG. 36. Accordingly, it is formed with an elongate polyetherimide support and thermal barrier extending from a leading end represented generally at 912 to a trailing end shown generally at 914. This thermal barrier supports a polyimide circuit support (Kapton), the outer surface of which carries four gold-plated copper thermal spreaders as seen at 916-919, heater resistor segments being located beneath the polyimide layer and registry with these thermal spreaders. A connector guide as represented generally at 920 is located adjacent trailing end 914. Leading end 912 of the thermal barrier now supports an introducer tip identified generally at 922. Tip 922 will permit the clinician to insert the implant 910 at the interface between dermis and next adjacent subcutaneous tissue or fat layer without the optional use of a separate introducer dissecting device.

Tip 922 may be formed of a type 304 stainless steel (full hard). Looking to FIG. 62, the tip 922 is revealed in perspective fashion and has a thickness of 0.005 inch and an overall length of 0.380 inch. The tip is configured with two cutting or dissecting edges 924 and 926 extending rearwardly from a point 928 at an included angle of 41°. Rearwardly of the edges 924 and 926 the tip 922 is configured with an embeddable rear portion represented generally at 930. Portion 930 is seen to be configured with embedding notches 932-935. Looking additionally to FIGS. 63 and 64, a sectional view reveals embeddable rear portion 930 as it is located within the thermal barrier as a consequence of an injection molding process. The blade edges 924 and 926 extend axially to point 928, a distance of 0.160 inch.

In use, the clinician forms a small entrance incision within the skin at the heating channel entrance location then manually inserts the bladed implant 910 through that incision, in a manner wherein it will bluntly dissect and be located within a heating channel positioned at the interface between dermis and the next adjacent subcutaneous tissue or fat layer.

In the course of development of the instant implants and method, it was determined that the overall length of the implants utilized should be a fixed value, for instance, 7.75 inches and that the active or heating regions within that constant implant length should vary but be formed with a consistent identical number of heating and temperature sensing resistor segments. By thus standardizing the number of resistor segments, for example, four, the associated control system may be more simply configured to consistently perform in conjunction with that number of resistor segments. FIG. 65A-65C combine to illustrate this standardization approach in structuring the implants which developers have referred to as "wands". In FIG. 65A, one version of such an implant is represented in general at 940 and is labeled at dimension arrow 942 as having a fixed length, i.e., 7.75 inches. Within this fixed length there is a heating region represented by and labeled at dimension arrow 944. The heating region length at arrow 944 may, for example, be 3.2 inches and the length of the thermal spreaders and associated embedded resistor segments 946-949 may be, for example, 15 mm. From the heating region dimension arrow 944 there extends a non-heating region represented at dimension arrow 950 which supports no electrodes and extends that length of the implant which remains 3 mm in width. Because the implants may be inserted at the dermis-fat layer interface from aesthetically elected entrance locations, positioning indicia as represented generally at 952 may be imprinted along the non-heating region and visually related to the entrance incision location. Indicia 952 are somewhat similar to the distance marking indicia on catheters.

Looking to FIG. 65B, a next version of a system implant is represented generally at 960. Implant 960 is configured with a fixed consistent length corresponding with that of implant 940, i.e., 7.75 inches, as represented at dimension arrow 962. The heating region for implant 960 is represented at dimension arrow 964 and will be shorter than the heating region of implant 940, for example, being about 2.4 inches in length. However, within the heating region remain a fixed, consistent four thermal spreaders 966-969 and associated resistor segments. Those spreaders and resistor segments may, for example, have a common length of 12 mm. Extending rearwardly from the heating region, as before, is a non-heating region represented by dimension arrow 970. This non-heating region may be observed to be lengthier than the corresponding non-heating region 950 of implant 940. As before, positioning or implant insertion extent identifying visible indicia as represented generally at 972 may be provided along the non-heating region.

Referring to FIG. 65C, a third version of the implant is represented in general at 976. Implant 976 has the noted fixed length, i.e., 7.75 inches which is consistent with that of implants 960 and 940 as represented at dimension arrow 978. Implant 976 is configured with a heating region of about 1.6 inches in length as represented at dimension arrow 980. As before, the heating region incorporates a fixed consistent four thermal spreaders and associated embedded resistor segments 982-985. These thermal spreaders may have a length, for example, of 8 mm. The non-heating region for implant 976 is more elongate as represented by dimension arrow 986. This non-heating region incorporates implant insertion extent positioning indicia as represented generally at 988.

FIGS. 66A-66J combine as labeled thereon to provide a flowchart describing a method of the invention. At the commencement of the procedure, the clinician determines that skin region suited for shrinkage as indicated at block 1000. In correspondence with this determination, as represented at line 1002 and block 1004, a determination is made as to the desired percentage extent of linear collagen shrinkage. In this regard, an upper limit of less than about 25% shrinkage is recommended. Line 1006 extends from block 1004 to the determination at block 1008 wherein consideration is made as to the amount of shrinkage to be provided at the borders of the skin region to provide a form of "feathering". Once the parameters of shrinkage are determined, then as represented at line 1010 and block 1012 a therapy interval can be projected or estimated. That interval will be determined with respect to a predetermined setpoint therapy temperature as discussed in connection with FIG. 60. The quantification of therapy intervals has been discussed above in connection with equation (1) and publication 15. These determinations also are predicated upon whether a temperature setpoint lowering adjuvant is to be used in conjunction with the heating of the skin region for shrinkage, for instance, hyaluronidase may be administered to the skin region. Accordingly, as represented at line 1014 and block 1016, a query is posed as to whether adjuvant is to be used. If it is not to be used, then as represented at line 1018 and block 1020, the setpoint temperature (resistor segment) is established as $T_1$. This corresponds with dashed line 880 in FIG. 59. The method then continues as represented at line 1022.

Use of such adjuvant is highly beneficial in terms of providing thermal protection to both the next adjacent subcutaneous tissue or fat layer as well as to the epidermis, with the lower temperature collagen shrinkage domain being developed by delivering adjuvant to the skin region targeted for shrinkage. Administration of adjuvant may be carried out, for instance by topically applying in over the targeted skin surface or by delivering adjuvant from the surface of the implant. Where the query posed at block 1016 results in an affirmative determination that an adjuvant is to be used, then as represented at line 1024 and block 1026, the type and quantity of adjuvant and the adjuvant delivery system are determined. As represented at lines 1028 and block 1030, the setpoint temperature is established as $T_2$, wherein the basic setpoint temperature $T_1$, is diminished to an extent of $\Delta T_a$, where $\Delta T_a$, is equal to the reduction of the $\Delta T$ necessary to reach a collagen shrinkage domain. For the example of high hyaluronidase, $\Delta T_a$, the reduction of $\Delta T$, is about 10° C. to 12° C. and thus $T_2$, is 10° C. to 12° C. less than $T_1$.

Whether the adjuvant chosen at block 1026 is to be topically applied or otherwise, it is administered to the skin region targeted for shrinkage as represented at line 1032 and block 1034. After an administration of the adjuvant, as represented at line 1036 and block 1038, a delay or time interval $t_1$, ensues of time length effective for diffusion of the adjuvant, for example, through the stratum corneum and remaining epidermis into the dermis and including the time length necessary for the adjuvant to lower $\Delta T$. Following the delay interval $t_1$, any excess adjuvant resulting from topical application may be removed from the skin surface. In this regard, the adjuvant may be incorporated in a cream carrier. Removal of the excess adjuvant also clears the skin surface for providing a starting pattern of visible indicia such as dots. However, the excess adjuvant at the skin surface may be permitted to remain and function as a heat transfer and lubricating medium.

If the adjuvant chosen at block 1026 is to be an implant delivered one, it is activated by heating of the implant for a time interval of length effective for release of the adjuvant. A delay may then ensue for a time length effective for diffusion of the adjuvant into dermis. The adjuvant application features described with respect to transdermal or implant delivered adjuvants also may be carried out when utilizing other adjuvants and delivery systems. When employing other adjuvant delivery methods, such as iontophoretic delivery, the adjuvant may be applied to the skin surface and then drawn into the dermis by activation of an appropriate electric cable field. Delay periods necessary for activity of the delivered adjuvant are familiar to those employing known methods in dermatologic fields including, for instance, local anesthesia. The program, as represented at line 1040 returns to line 1022. Line 1022 is seen to extend to block 1042 providing for a determination of heating channel locations including their entrance locations, length and spacing. Next, as represented at line 1044 and block 1046, an implant is provided for each channel location. Preferably, such implants will incorporate a thermal spreader as described in connection with FIGS. 36-39 and when incorporating multiple resistor segments will be of standardized lengths as described in conjunction with FIGS. 65A-65C. As represented at line 1048 and block 1050, an implant with a bladed thermal barrier leading end may be provided as described in conjunction with FIGS. 61-64. Line 1052 extends from block 1050 to block 1054. The latter block describes the provision of a starting pattern of visible indicia at the surface of the skin suited for evaluating the percentage of shrinkage developed. Placement of such indicia has been described in connection with FIG. 54. The pattern may be developed with a template, and, as represented at line 1056 and block 1058, a digital image of the starting pattern may be provided. Line 1060 leads from block 1058 to block 1062 providing for the selection of a heat sink configuration for controlling the temperature at epidermis surface to reside within a range of about 37° C. and not to exceed 40° C. Line 1064 extends from block 1062 to branch lines 1066 and 1068 which extend respectively to blocks 1070 and 1072. Block 1070 describes the transparent polymeric conformal bag-like container incorporating a pulsating pneumatic bladder as discussed in connection with FIGS. 46 and 47. Block 1072 describes a transparent polymeric bag-like conformal container with recirculation water developed with a temperature controlled reservoir and pump as described in connection with FIG. 48. Line 1074 extends from block 1072 to another configuration identified at block 1076 wherein a transparent polymeric conformal container is combined with a re-circulating temperature controlled liquid such as water and a mechanical agitator as described in connection with FIG. 49. Line 1078 extends from block 1072 to block 1080 to identify another configuration which is the heat controlled aluminum heat sink described in connection with FIGS. 17-19. Line 1082 extends from block 1076 to block 1084 identifying another heat sink configuration. At that block, a transparent polymeric conformal container with a magnetic stirring assembly configuration is set forth as has been described in connection with FIGS. 50 and 51. Line 1086 extending from block 1080 leads to block 1088 representing another transparent polymeric bag-like conformal container configuration which incorporates a motor driven propeller form of agitation. This approach has been described in connection with FIGS. 52 and 53. Line 1090 extending from block 1084 and line 1092 extending from block 1088 lead to line 1094 and block 1096 indicating that where transparent container is selected, the clinician may optionally provide a pattern of visible indicia adjacent its contact surface which corresponds with the starting pattern of visible indicia. That arrangement has been described in connection with FIGS. 55 and 56. As represented by line 1098 and block 1100, the outside of the contact surface of the transparent heat sink may be treated with a thin, transparent layer of thermochromic material which has a visually perceptible color cue at epidermis surface temperatures above a maximum value, for example, 40° C. With the emergence of this color at a region as described in connection with FIG. 57, the system can be shut down. Line 1102 extends from block 1100 through the optional arrangement set forth at block 1104. That option provides for the location of one or more temperature sensors on the heat sink container surface for the purpose of measuring liquid (water) temperature while it is being stirred. Such sensors should be displaced from the heat sink contact surface. Next, as represented at line 1106 and block 1108, an appropriate heat sink (water) temperature is determined taking into account the temperature drop at the interface between the epidermis surface and the heat sink contact surface. The temperature of the water within the polymeric bag-like conformal container will be within a range of about 20° C. to 26° C. The procedure then continues as represented at line 1110 extending to block 1112. Block 1112 provides that the subcutaneous fat layer may be pre-cooled from the skin surface for a pre-cooling interval. As represented at line 1114 and block 1116 the clinician may optionally form the heating channels for receiving implants utilizing a surgically blunt dissecting introducer device. Such a device has been described in conjunction with FIGS. 44 and 45. Line 1118 extends from block 1116 to introduce procedures for administering local anesthetic. It is preferred that the local anesthetic be administered by injection as opposed to diffusion through the epidermis and dermis. The more popular of anesthetic agents is lidocaine combined with a normal saline diluent. Line 1118 extends to block 1120 providing for administration of the local anesthetic, whereupon, as represented at line 1122 and block 1124 a delay, $t_2$, ensues for anesthetic effectiveness. It may be recalled that a diffusion delay, $t_1$, is required following application of adjuvants. That delay generally will be of shorter duration than the delay for anesthetic effectiveness. Accordingly, the clinician may wish to carry out the procedure of block 1038 subsequent to the procedure at block 1124. At this stage in the procedure the practitioner will attach the resistor segment leads to the system controller. Such connection is represented at line 1126 and block 1128. Following connection with the system controller, as represented at line 1130 and block 1132, an entrance incision is formed at each heating channel entrance location. The clinician, as represented at line 1134 and block 1136 may then employ a dissecting instrument or introducer device to form heating channels commencing at each heating channel entrance location. Next, as represented at line 1138 and block 1140, an implant is inserted within each heating channel through the now open entrance location. The resistor segments will be oriented for thermal exchange with the lower region or surface of the dermis layer.

Line 1142 extends from block 1140 to describe the next option represented at block 1144. For this option, the heating channel may be formed by a bladed implant while the implant is being positioned. Such a bladed implant has been described in connection with block 1050. For either implant option, as represented at line 1146 and block 1148, the clinician may control the length of implant insertion by observing the positioning indicia with respect to the channel entrance location incision. Such indicia has been described in connection with FIGS. 65A-65C.

As part of this positioning, the clinician also may verify implant location by palpation as represented at line 1150 and block 1152. Following such positioning, as represented at line 1154 and block 1156, a heat transferring liquid such as water or glycerol is applied to the skin region of interest. This fluid also serves as a lubricant permitting the movement of skin below an applied heat sink. In the latter regard, as represented at line 1158 and block 1160, the selected heat sink is positioned against the skin region epidermis and whatever agitator or recirculation system which is associated with it is actuated. An aspect of the heat sink positioning may involve the registration of indicia between the heat sink and skin surface. Accordingly, as represented at line 1162 and block 1164, where appropriate, such alignment of a contact surface pattern of visible indicia or the like is aligned with the starting pattern of indicia at the skin surface. Such an arrangement has been discussed above in connection with FIGS. 54-56. Next, as represented at line 1166 and block 1168, the water agitation function of the heat sink is actuated to provide for temperature regulation. With the positioning of the implants, as represented at line 1170 and block 1172, the controller associated with the cables attached to the implants will verify whether or not proper electrical connections have been made. In the event they have not, then as represented at line 1174 and block 1176 the operator will be cued as to the discrepancy and prompted to recheck connections. The program then returns to line 1170 as represented at line 1178. In the event of an affirmative determination with respect to the query posed at block 1172, then the procedure continues as represented at line 1180 and block 1182 where the operator initiates auto-calibration of all resistor segments with respect to setpoint temperature. Auto-calibration has been discussed above in connection with equations (2) and (3). When the setpoint temperature related resistance(s) have been developed, as represented at line 1184 and block 1186, the resistance value(s) associated with setpoint temperature(s) are placed in memory and the program continues as represented at line 1188 and block 1190. The query at block 1190 determines whether auto-calibration has been successfully completed. In the event that it has not, then as represented at line 1192 and block 1194, the controller provides an illuminated auto-calibration fault cue and, as represented at line 1196 and block 1198, it provides a prompt to recheck connection of cables and to replace any faulty implants. The program then loops to line 1180 as represented at line 1200. Returning to block 1190, where auto-calibration has been successfully completed, then as represented at line 1202 and block 1204, slight pressure or tamponade is applied over the skin region of interest through the selected heat sink. For example, such pressure has been described as being applied through a transparent glass plate as discussed, inter alia, in connection with FIG. 47. In general, this pressure will be greater than 0 psi and does not need to be greater than 0.22 psi.

The program then commences to initiate the treatment or therapy as represented at line 1206 and block 1208. From block 1208, line 1210 extends to block 1212 providing for the commencement of temperature sampling, for example, every 10-100 milliseconds. The sampling interval may be for 1 or 2 milliseconds with respect to the heater segment. Temperature characteristics associated with the resistor segment form of heating have been discussed in connection with FIG. 59.

At this early juncture in the procedure, the operator may wish to stop the therapy. Accordingly, as represented at line 1214 and block 1216 the program determines whether a stop therapy command has been received by the system. In the event that it has been received, then as represented at line 1218 and node A, all heater segments will be de-energized. Node A reappears in conjunction with line 1256 leading to block 1258. In the event there has been no stop therapy command received by the system, then as represented at line 1220 the procedure continues and, as represented at block 1222 the clinician may observe instantaneous shrinkage. Such observation continues as represented at line 1224 which extends to the query at block 1226 which determines whether a thermochromic over-temperature cue has been observed. This temperature monitoring has been described above in connection with FIG. 57. In the event an over-temperature cue is present, then as represented at line 1228 and node A, the procedure is terminated, all heater segments being de-energized. Where no over-temperature cue is present, then as represented at line 1230 and block 1232 a determination is made as to whether all heater segment target or setpoint temperatures have been reached. In the event they have not, then the procedure loops to line 1230 as represented at line 1234. Where the heater segments have reached target temperature, then as represented at line 1236 and block 1238, therapy timing commences and the procedure continues as represented at line 1240 to the query at block 1242 representing a determination as to whether the extent of shrinkage desired has been reached. In this regard, the desired extent of collagen shrinkage may be accomplished before the end of a predetermined therapy interval. Where that goal has not been reached, then as represented at line 1244 and block 1246 a query is posed as to whether the predetermined therapy interval has been completed. In the event that it has not, then as represented at line 1248 and block 1250, a query is again made as to whether the operator has initiated a stop therapy condition. This stopping of therapy may, for instance, be a consequence of a malfunction such as an unwanted burn condition, a surface over-temperature cue, or in the event a shrinkage goal has been reached before the termination of a therapy interval. In the event of a negative determination, then as represented at line 1252 the program loops to line 1240 and the queries which repeat.

Looking to the query at block 1242, where the shrinkage goal has been reached, then as represented at line 1254, the program reverts to node A. Node A reappears in conjunction with line 1256 and block 1258 providing for the de-energization of all heater segments. Looking to block 1246, in similar fashion where the projected therapy interval is completed, then as represented at line 1260 the procedure reverts to node A. Returning to block 1250, where an operator initiated stop therapy command has been received by the system, then as represented at line 1262 the system reverts to node A and the de-energization of all resistor segments.

Returning to block 1258 following the de-energization of all heater segments, as represented at line 1264 and block 1266, post therapy continued temperature control is carried out for a post therapy interval. The post therapy interval may last, for example, about two minutes. Accordingly, as represented at line 1268 and block 1270, a determination is made as to whether the post therapy interval is completed. In the event that it is not, then as represented at line 1272 extending to line 1268 the program loops. If the post therapy interval is completed, then as represented at line 1274 and block 1276 the heat sink is removed with concomitant release of pressure, and the program continues as represented at line 1278 and block 1280. At this stage in the procedure, the clinician evaluates the extent of collagen shrinkage accomplished. As represented at line 1282 and block 1284, a query is posed as to whether an acceptable extent of shrinkage has been accomplished. In the event that it has not, then as represented at line 1286 and block 1288, the heat sink is restored and activated and the procedure reverts to node B as represented at line 1290. Node B reappears in connection with line 1292 extending to line 1202 restarting the therapy.

Looking again to the query posed at block 1284, where an acceptable extent of shrinkage has occurred, then as represented at line 1294 and block 1296, the implants are removed, and as indicated at line 1298 and block 1300, all entrance incisions are repaired. As represented at line 1302 and block 1304, therapy is then completed. However, as shown at line 1306 and block 1308, the clinician will carry out a post therapy review to determine the presence of successful neocollagensis.

The implants also may be employed in treating capillary malformation which often is referred to as port wine stain (PWS). As discussed above in connection with publication 14, such lesions have been classified, for instance, utilizing video microscopy, three patterns of vascular ectasia being established; type 1 ectasia of the vertical loops of the capillary plexis; type 2 ectasia of the deeper, horizontal vessels in the capillary plexis; and type 3, mixed pattern with varying degrees of vertical and horizontal vascular ectasia. As noted above, in general, due to the limited depth of laser treatment, only type 1 lesions are apt to respond to such therapy.

Capillary malformations (PWS) also are classified in accordance with their degree of vascular ectasia, four grades thereof being recognized as Grades I-IV. The grade categorizations are discussed above. FIGS. 67A-67H are combined as labeled thereon to provide a process flow chart for the treatment of capillary malformation. Looking to FIG. 67A and block 1340, a determination is made of the type and Grade of the capillary malformation lesion. Then, as represented at line 1342 and block 1344, a query is posed as to whether a type 1 lesion is at hand. If that is the case, then as represented at line 1346 and block 1348, the practitioner may want to consider the utilization of laser therapy. On the other hand, where the determination at block 1344 indicates that a type 1 lesion is not at hand, then as represented at line 1350 and block 1352, the practitioner will consider resort to implant therapy with implants as disclosed herein. In accordance with the instant teachings, as represented at line 1354 and block 1356, resistor segment heater implant therapy will be elected. Energization of the heater resistor segments will be carried out, for example, as discussed in connection with FIG. 59 but at a much lower setpoint temperature which will not adversely affect dermis tissue, i.e., that setpoint temperature will be atraumatic with respect to dermis. In general, such setpoint temperature will be in a range from about 45° C. to about 60° C. Once setpoint temperature is reached, as represented at line 1358 and block 1360, the practitioner will determine a therapy interval based upon the predetermined type and grade of lesion. Heating of the blood vessels of the lesion takes place to an extent evoking necrotic cauterization and subsequent dissipation (resorption) from the dermis. When this occurs, while the heating remains atraumatic to dermis, over time angiogenesis or the formation of new blood, blood vessels will occur, typically without the regeneration of capillary malformation. Next, as indicated at line 1362 and block 1364, a determination is made as to the heating channel locations including the entrance locations to those channels and the length and spacing of the channels. It may be recalled, that where the implants of the present teaching are employed in a mutually parallel manner, then an edge-to-edge spacing of about 5 mm is recommended for implant widths of about 3 mm. Once the heating channels are determined, then as represented at line 1366 and block 1368, for each such heating channel there is provided a thermal barrier supported heater resistor segment implant. As discussed in connection with FIGS. 65A-65C, it is preferred that the implants will have the same overall length and retain a fixed or consistent number of heater resistor segments as well as thermal spreaders, those components varying in a common length. As represented at line 1370 and block 1372, the practitioner will attach resistor leads to controller cables. Circuit continuity may be tested at this juncture. The procedure continues with selection of a heat sink configuration as represented at line 1374 and block 1376. Generally, the heat sink will maintain the epidermis surface temperature within a range of about 30° C. to about 37° C. Various heat sink configurations have been discussed above in connection with FIGS. 46-53. Should the heat sink selected be transparent, then as represented at line 1378 and block 1380 as an option, a layer of thermochromic material having a visibly perceptible color cue at epidermis surface temperature above an elective maximum can be provided. The material layer will be located at the "skin" side of the container contact surface. Such material has been discussed above in connection with FIG. 57. Another option is represented at line 1382 and block 1384 wherein one or more temperature sensors may be located on the heat sink container surface displaced from its contact surface. In this same regard, as represented at line 1386 and block 1388, appropriate heat sink temperature is determined taking into account the temperature drop at the interface between the epidermis surface and the heat sink contact surface with respect to skin surface temperature. In general, the heat sink liquid temperature will be in a range of about 20° C. to about 26° C. Line 1390 extends from block 1388 to block 1392 which provides that the practitioner may wish to pre-cool the subcutaneous fat layer from the skin surface for a pre-cooling interval. Where a bladed implant has not been provided as described in conjunction with FIGS. 61-64, then the heating channel may be formed utilizing a blunt dissecting introducer instrument as discussed in connection with FIGS. 44 and 45. Next, as represented at line 1398 and block 1400, a local anesthetic may be administered, an injection form of administration being preferred. Time is required for the local anesthetic to become effective, thus, as represented at line 1402 and block 1404, a delay ensues awaiting an anesthetic effectiveness. As the local anesthetic becomes effective, then, as represented at line 1406 and block 1408, using a scalpel, for each heating channel entrance location, an entrance incision is made to the dermis-subcutaneous fat layer interface. Optionally, as represented at line 1410 and block 1412, a blunt dissecting instrument as provided at block 1396 may be employed for forming the heating channel(s) through the entrance incision(s). Once so formed, as represented at line 1414 and block 1416, an implant is inserted within each channel in an orientation wherein all heat spreaders are contactable with dermis. Generally, it has been found that where the implants are pre-connected to the controller cables, insertion is more facilely carried out. Heating channels also may be formed in conjunction with the insertion of implants where a bladed implant is employed as represented at line 1418 and block 1420. Such bladed implants have been described in connection with FIGS. 61-64. Line 1422 extending from block 1420 to block 1424 indicates that the extent of implant insertion may be controlled by observing positioning indicia with respect to the entrance incision. Such indicia has been described above in connection with FIGS. 65A-65C. Next, as represented at line 1426 and block 1428, the position of the implants may be verified by palpation. In preparation for positioning of the heat sinks, as represented at line 1430 and block 1432, a heat transferring liquid, for example, water, is applied to the skin surface over the implants, whereupon, as represented at line 1434 and block 1436, a heat sink is positioned over the implants, such heat sink having been selected as described in connection with block 1376. Upon such placement, as represented at line 1438 and block 1440, a liquid agitator within the heat sink or the like is actuated for heat sinking temperature regulation. With the heat sink in position, as represented at line 1442 and block 1444, a determination is made as to whether all cables are securely connected to the controller as well as the implant leads. In the event they are not, then as represented at line 1446 and block 1448 the practitioner is cued as well as prompted to recheck the connections of those cables indicating a fault. The program then loops to line 1442 as represented at line 1450. In the event of an affirmative determination with respect to block 1444, then as represented at line 1452 and block 1454, auto-calibration of the heater resistor segments with respect to set point temperature is carried out. Such auto-calibration has been discussed above in connection with blocks 1182 et seq. As represented at line 1456 and block 1458, resistance values representing setpoint temperature are placed in memory. The program continues as represented at line 1460 to the query posed at block 1462 determining whether the auto-calibration procedure has been successfully completed. In the event that it has not been successfully completed, then as represented at line 1464 and block 1466, an auto-calibration fault cue is illuminated and, as represented at line 1468 and block 1470, the practitioner is prompted to re-check connections of cables to the controller and replace any faulty implants. The program then loops as represented at lines 1472 and 1460. In the event of an affirmative determination with respect to the query posed at block 1462, then as represented at line 1474 and block 1476, slight pressure is applied to the surface of the skin under treatment to assure appropriate thermal spreader/dermis contact and conduction heat transfer from the polymerically encapsulated heater resistor segment (tamponade). With such pressure application, as represented at line 1478 and block 1480 therapy is commenced by applying d.c. current to the heater resistor segments while periodically polling or sampling those resistor segments for temperature related resistance values. It may be recalled that for the instant therapy, the setpoint temperature is relatively low so as to remain atraumatic to the dermis, avoiding shrinking phenomena. The heat energy dosage is that providing for the necrotic coagulation of the blood vessel phenomena associated with capillary malformation. As represented at line 1482 and block 1484, for any of a variety of reasons, the practitioner may initiate a stop therapy condition. Such condition is represented by the query posed at block 1484. In the event that such a stop command has been received, then as represented at line 1486 and node A, all resistor segments are de-energized. A stop therapy command may result from the next query as represented at line 1488 and block 1490, determining whether the thermochromic over-temperature cue has been activated. This skin surface over-temperature sensor approach has been described above in connection with FIG. 57. Accordingly, where such an over temperature cue has been observed, then as represented at line 1492 and node A, all resistor segments are de-energized. The procedure then continues as represented at line 1494 and block 1496 determining whether all heater segment setpoint temperatures have been reached. In the event that they have not been reached, then as represented at line 1498 extending to line 1494, the system dwells until such setpoint temperatures have been reached. Accordingly, where those temperatures have been reached, as represented at line 1500 and block 1502 therapy timing is commenced along with temperature setpoint control which is carried out by periodically sampling resistance values at the 4-point configured lead assemblages. With the reaching of setpoint temperature the procedure continues as represented at line 1504 and block 1506 determining whether the therapy interval is completed, In the event that it is completed, as represented at line 1508, the procedure reverts to node A providing for the de-energization of all heater segments. Where the therapy interval is not completed, as represented at line 1510 and block 1512, a determination is made again as to whether the operator has initiated a stop therapy condition. Where such a stop therapy condition has been initiated, for example, responding to an over-temperature cue, as discussed in connection with block 1490, then as represented at line 1514 the procedure reverts to node A and a de-energization of all heater segments. In the event that the therapy interval continues and no stop therapy command has been received, the program loops as represented at line 1516 extending to line 1504.

Node A reappears in conjunction with line 1518 extending to block 1520 providing, as described above for the de-energization of all heater segments. Upon carrying out de-energization of the heater segments, as represented at line 1522 and block 1524, the practitioner initiates post therapy continued temperature control for a selected interval. This is carried out by maintaining the function of the heat sink for such interval. The post therapy being initiated, as represented at line 1526 and block 1528, the program queries as to whether the post therapy interval is completed. In the event it has not been completed, then as represented at lines 1530 and 1526, the program loops. Where the post therapy interval has been completed, then as represented at line 1532 and block 1534, the heat sink is removed and as represented at line 1536 and block 1538 the implants are removed. Upon such removal, as represented at line 1540 and block 1542, all entrance incisions are repaired. Next, as represented at line 1544 and block 1546, a clearance interval ensues, for instance, having a duration of about 6-8 weeks over which time the necrotically coagulated blood vessels causing capillary malformation are naturally (resorption) absorbed. In general, the body function will tend to create normal vascularity in the treated region. As noted above, this is referred to as angiogenesis. Following the clearance interval, as represented at line 1548 and block 1550, a determination is made as to whether there are lesion regions remaining. In the event there are no such lesions remaining, then as represented at line 1552 and block 1554, therapy is completed. Where lesion regions do remain, then as represented at line 1556 and block 1558, a determination is made as to whether the remaining lesion region(s) are the equivalent to the earlier-described type 1 which are amenable to laser therapy. In the event that they are, then as represented at line 1560 and block 1562, the practitioner may consider laser therapy. Whether remaining lesions are not equivalent to type 1, then as represented at line 1564 and block 1566 the practitioner may consider implant therapy.

Since certain changes may be made in the above apparatus and method without departing from the scope of the instant description herein involved, it is intended that all matter contained in the above description or shown in the accompanying drawings shall be interpreted as illustrative and not in a limiting sense.

The invention claimed is:

1. The method for effecting a controlled heating of tissue within the region of the dermis of skin, comprising the steps:
   (a) determining a skin region for treatment;
   (b) providing one or more heater implants each comprising a thermally insulative generally flat support having a support surface and an oppositely disposed insulative surface, the support extending between leading and trailing ends, a circuit located adjacent said support surface having one or more electrical resistance heater segments with leads extending to the trailing end;
   (c) determining one or more heating channel locations along said skin region;
   (d) locating each heater implant along a heating channel generally at the interface between dermis and next adjacent subcutaneous tissue in an orientation wherein said one or more heater segments are positioned for thermal exchange relationship with adjacent tissue within the region of dermis and in thermally insulative relationship with said next adjacent subcutaneous tissue;
   (e) applying tamponade over at least a portion of said skin region to an extent effective to maintain substantially continuous conduction heat transfer between tissue within the region of dermis and said one or more heater segments;
   (f) simultaneously with step (e) controlling the temperature of the surface of skin in at least a portion of said skin region to an extent effective to protect the skin surface from thermal injury while permitting the derivation of effective therapeutic temperature at tissue within the said region of the dermis; and
   (g) effecting an energization of said one or more heater segments substantially to attain a setpoint temperature.

2. The method of claim 1 in which:
step (g) is carried out to effect a controlled shrinkage of dermis or a component of dermis of skin.

3. The method of claim 1 in which:
step (g) is carried out to effect a therapeutic treatment of a capillary malformation.

4. The method of claim 3 in which:
step (g) is carried out to effect an irreversible vascular coagulation with a setpoint temperature atraumatic to dermis.

5. The method of claim 1 further comprising the step:
(h) monitoring the temperature of said electrical resistance heater segments during step (g).

6. The method of claim 5 in which:
step (b) provides one or more heater implants with leads defining a 4-point configuration for determining the electrical resistance of each segment and for electrically heating each segment; and
step (h) is carried out by intermittently determining said electrical resistance and comparing that resistance with a resistance value corresponding with setpoint temperature.

7. The method of claim 1 in which:
step (f) is carried out with a heat sink assemblage having a contact surface in thermal exchange contact with the surface of skin at the skin region.

8. The method of claim 7 in which:
step (e) is carried out by applying pressure to said skin region from said heat sink contact surface.

9. The method of claim 7 in which:
step (f) is carried out with a temperature controlled metal heat sink having a contact surface which is located in thermal exchange relationship with the surface of skin of said skin region.

10. The method of claim 7 in which:
step (f) is carried out with a heat sink configured as a conformal container of liquid having a said contact surface located against skin at said skin region.

11. The method of claim 7 in which:
step (f) is further carried out by locating a heat transferring substance intermediate the surface of skin at said skin region and the contact surface of the container.

12. The method of claim 10 in which:
step (f) is further carried out by effecting an agitation of liquid within said container adjacent skin at said skin region.

13. The method of claim 10 in which:
step (f) is carried out with liquid within said container at a temperature between about 22° C. and about 30° C.

14. The method of claim 10 in which:
step (g) is carried out to effect a controlled shrinkage of dermis or a component of dermis of skin; and
step (f) is carried out with a conformal container having a transparency effective to permit viewing of skin surface at said skin region.

15. The method of claim 14 further comprising the steps:
(j) providing a pattern of visible indicia at said skin region prior to steps (e), (f), and (g), and providing a corresponding pattern of visible indicia adjacent said container contact surface; and
(k) monitoring the extent of skin shrinkage during step (g) by comparing said pattern of visible indicia at said skin region with said pattern of visible indicia at said container contact surface.

16. The method of claim 1 in which:
step (g) is carried out to effect a controlled shrinkage of dermis or a component of dermis of skin; and
further comprising the step:
(i) administering an adjuvant generally to dermis at said skin region effective to lower the thermal transition temperature for carrying out the shrinkage of dermis or a component of dermis.

17. The method of claim 16 in which:
step (i) administers said adjuvant topically at said skin region.

18. The method of claim 16 which:
step (b) provides one or more implants as carrying said adjuvant at a location for dispersion within dermis from the heating channel.

19. The method of claim 1 further comprising the step:
(j) precooling said next adjacent subcutaneous tissue through the surface of skin at said skin region prior to steps (d) through (g).

20. The method of claim 1 in which:
step (f) is continued subsequent to step (g) for an interval effective to alter the temperature of heated dermis toward human body temperature.

21. The method of claim 1 in which:
step (b) provides one or more implants each having a polymeric electrically insulative circuit support assembly along the support surface with an outwardly disposed thermal exchange surface covering the heater segments, and one or more metal thermal spreaders mounted upon said circuit support assembly thermal exchange surface in heat exchange relationship with a corresponding heater segment.

22. The method of claim 21 in which:
step (b) provides one or more implants having thermal spreaders formed with copper having a thickness of between about 0.005 and about 0.020 inch.

23. The method of claim 1 in which:
step (b) provides two or more implants wherein said thermally insulative generally flat support exhibits a lengthwise dimension between said leading and trailing ends which is a fixed, consistent value, and said circuit has a fixed consistent number of electrical resistance heater segments having a common length which may vary among given implants.

24. The method of claim 23 in which:
step (b) provides said two or more implants as exhibiting a lengthwise dimension of about 7.5 inches.

25. The method for effecting a controlled heating of tissue within the region of the dermis of skin, comprising the steps:
(a) determining a skin region for treatment;
(b) providing one or more heater implants each comprising a thermally insulative generally flat support having a support surface and an oppositely disposed insulative surface, the support having a length extending between leading and trailing ends, a circuit supported from said support surface having one or more electrical resistance heater segments along with leads extending to the trailing end;
(c) determining one or more heating channel locations at said skin region, each having a channel entrance location;
(d) forming an entrance incision at each channel entrance location;
(e) locating a heater implant within each heating channel location by insertion of the leading end through an entrance incision and positioning it generally at the interface between dermis and next adjacent subcutaneous tissue in an implant orientation wherein the heater segments are positioned for conduction heat transfer with adjacent dermis and in thermally insulating relationship with next adjacent subcutaneous tissue;
(f) applying tamponade over at least a portion of said skin region to an extent effective to maintain substantially continuous conduction heat transfer between the one or more heater segments of each implant and adjacent dermis;
(g) effecting an energization of said one or more heater segments substantially to derive a setpoint temperature for a thermal dosage interval; and
(h) simultaneously with step (f) controlling the temperature of the surface of skin within said skin region by heat sinking to an extent effective to protect the skin surface from thermal injury while permitting the derivation of effective treatment temperature at the region of dermis.

26. The method of claim 25 in which:
step (g) is carried out to effect a controlled shrinkage of dermis or a component of dermis of skin.

27. The method of claim 25 in which:
step (g) is carried out to effect a therapeutic treatment of a capillary malformation.

28. The method on 27 in which:
step (g) is carried out to effect an irreversible vascular coagulation with a setpoint temperature atraumatic to dermis.

29. The method of claim 25 in which:
step (h) controls the temperature of the skin within said region within a range of from about 37° C. to about 40° C.

30. The method of claim 26 further comprising the step:
(i) during and/or after step (h) determining the extent of collagen shrinkage.

31. The method of claim 30 in which:
step (i) provides a pattern of visible indicia at said skin region prior to step (j) and visually determines the extent of relative movement of said indicia.

32. The method of claim 25 in which:
step (h) is continued subsequent to the termination of step (g) for an interval effective to alter the temperature of heated tissue within the region of dermis toward human body temperature.

33. The method of claim 25 further comprising the step:
(j) precooling said next adjacent subcutaneous tissue through the surface of skin at said skin region prior to steps (d) through (g).

34. The method of claim 25 in which:
step (h) is carried out with a liquid containing conformal container having a contact surface located against skin at said skin region.

35. The method of claim 34 in which:
step (h) is carried out with liquid within said container at a temperature between about 20° C. and about 26° C.

36. The method of claim 34 in which:
step (g) is carried out to effect a controlled shrinkage of dermis or a component of dermis of skin; and
step (h) is carried out with a conformal container having a transparency effective to permit viewing of skin surface at said skin region.

37. The method of claim 36 further comprising the steps:
(k) providing a pattern of visible indicia at said skin region prior to step (d), and providing a corresponding pattern of visible indicia adjacent said container contact surface; and
(l) monitoring the extent of skin shrinkage during step (g) by comparing said pattern of visible indicia at said skin region with said pattern of visible indicia at said container surface.

38. The method of claim 34 in which:
step (h) promotes a thermal exchange by agitation of said liquid adjacent said contact surface.

39. The method of claim 37 in which:
step (h) is further carried out by locating a heat transferring substance intermediate the surface of skin at said skin region and said contact surface.

40. The method of claim 26 in which:
step (h) is carried out with a temperature controlled metal heat sink having a contact surface which is located in thermal exchange relationship with the surface of skin at said skin region.

41. The method of claim 26 in which:
step (g) is carried out after having generally predetermined a therapy interval with respect to a desired extent of collagen shrinkage and target temperature.

42. The method of claim 26 further comprising the step:
(m) administering an adjuvant generally to dermis at said skin region effective to lower the thermal transition temperature for carrying out the shrinkage of dermis or a component of dermis.

43. The method of claim 42 in which:
step (m) administers said adjuvant topically at said skin region.

44. The method of claim 42 in which:
step (b) provides one or more implants as carrying said adjuvant at a location for dispersion within dermis from the heating channel.

45. The method of claim 25 in which:
step (h) is carried out with a heat sink assemblage having a contact surface in thermal exchange contact with the surface of skin at the skin region.

46. The method of claim 43 in which:
step (f) is carried out by applying pressure to said skin region from said heat sink contact surface.

47. The method of claim 25 in which:
step (b) provides one or more implants each having a polymeric electrically insulative circuit support assembly along the support surface with an outwardly disposed thermal exchange surface covering the heater segments, and one or more metal thermal spreaders mounted upon said circuit support assembly thermal exchange surface in heat exchange relationship with a corresponding heater segment.

48. The method of claim 47 in which:
step (b) provides one or more implants having thermal spreaders formed with copper having a thickness of between about 0.005 and about 0.020 inch.

49. The method of claim 25 in which:
step (b) provides two or more implants wherein said thermally insulative generally flat support exhibits a lengthwise dimension between said leading and trailing ends which is a fixed, consistent value, and said circuit has a fixed consistent number of electrical resistance heater segments having a common length which may vary among given implants.

50. The method of claim 49 in which:
step (b) provides said two or more implants as exhibiting a lengthwise dimension of about 7.5 inches.

51. The method for treating a capillary malformation within a skin region comprising the steps:
(a) determining the degree of vascular ectasia at said region;
(b) providing one or more heater implants each comprising a thermally insulative generally flat support having a support surface and an oppositely disposed insulative surface, the support extending between leading and trailing ends, a circuit located adjacent said support surface having one or more electrical resistance heater segments with leads extending to the trailing end;
(c) determining one or more heating channel locations within said region, each having an entrance location;
(d) locating each heater implant along a heating channel at the interface between dermis and next adjacent subcutaneous tissue in an orientation wherein said one or more heater segments are positioned for thermal exchange relationship with adjacent tissue in the region of dermis and in thermally insulative relationship with said next adjacent subcutaneous tissue;
(e) applying tamponade over at least a portion of said skin region to an extent effective to maintain substantially continuous conduction heat transfer between tissue within the region of dermis and said one or more heater segments;
(f) simultaneously with step (e) controlling the temperature of the surface of skin in at least a portion of said skin region to an extent effective to protect the skin surface from thermal injury while permitting the derivation of effective therapeutic temperature at said tissue within the region of dermis;
(g) effecting an energization of said one or more heater segments substantially to attain a setpoint temperature atraumatic to dermis while effecting an irreversible vascular coagulation of tissue within the region of dermis.

52. The method of claim 51 in which:
step (g) effects the energization of said heater segments to attain a setpoint temperature within a range of between about 45° C. and about 60° C.

53. The method of claim 51 further comprising the step:
(h) monitoring the temperature of each said electrical resistance heater segments during step (g).

54. The method of claim 53 in which:
step (b) provides one or more heater implants with leads defining a 4-point configuration for determining the electrical resistance of each segment and for electrically heating each segment; and step (h) is carried out by intermittently determining said electrical resistance and comparing that resistance with a resistance value corresponding with setpoint temperature.

55. The method of claim 51 in which:

step (f) is carried out with a heat sink assemblage having a contact surface in thermal exchange contact with the surface of skin at the skin region.

56. The method of claim 55 in which:

step (e) is carried out by applying pressure to said skin region from said heat sink contact surface.

57. The method of claim 55 in which:

step (f) is carried out with a heat sink configured as a conformal container of liquid having a said contact surface located against skin at said skin region.

58. The method of claim 51 further comprising the steps:

(i) subsequent the step (g) removing said one or more implants from each heating channel;

(j) waiting a clearance interval at least effective for the resorption of tissue at said skin region which has undergone irreversible vascular coagulation; and (k) then repeating step (a).

59. The method of claim 58 in which:

(l) where step (k) determines that any remaining capillary malformation is equivalent to a type 1 lesion, treating the remaining capillary malformation using laser-based therapy.

\* \* \* \* \*